(12) United States Patent
Chang et al.

(10) Patent No.: US 7,393,928 B2
(45) Date of Patent: *Jul. 1, 2008

(54) RECOMBINANT GELATINS

(75) Inventors: Robert C. Chang, Burlingame, CA (US); Kari I. Kivirikko, Oulu (FI); Thomas B. Neff, Atherton, CA (US); David R. Olsen, Menlo Park, CA (US); James W. Polarek, Sausalito, CA (US)

(73) Assignee: FibroGen, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/139,377

(22) Filed: May 27, 2005

(65) Prior Publication Data

US 2005/0229264 A1 Oct. 13, 2005

Related U.S. Application Data

(63) Continuation of application No. 09/710,239, filed on Nov. 10, 2000, now Pat. No. 6,992,172.

(60) Provisional application No. 60/204,437, filed on May 15, 2000, provisional application No. 60/165,114, filed on Nov. 12, 1999.

(51) Int. Cl.
*A61K 38/17* (2006.01)
*C09H 3/00* (2006.01)

(52) U.S. Cl. .................. 530/354; 530/350; 536/23.1; 435/69.1; 435/320.1; 435/325

(58) Field of Classification Search .................. 530/354, 530/350; 536/23.1; 435/320.1, 69.1, 325
See application file for complete search history.

(56) References Cited

U.S. PATENT DOCUMENTS

| | | | | |
|---|---|---|---|---|
| 5,821,089 A | * | 10/1998 | Gruskin et al. | 435/71.1 |
| 6,413,742 B1 | * | 7/2002 | Olsen et al. | 435/69.1 |
| 6,428,978 B1 | * | 8/2002 | Olsen et al. | 435/69.1 |
| 6,992,172 B1 | * | 1/2006 | Chang et al. | 530/354 |
| 2004/0005663 A1 | * | 1/2004 | Bell et al. | 435/69.1 |

OTHER PUBLICATIONS

Werten et al., Yeast 15, 1087-1096 (Aug. 1999).*

* cited by examiner

*Primary Examiner*—Chih-Min Kam
(74) *Attorney, Agent, or Firm*—James E. Nesbitt

(57) ABSTRACT

The present invention relates to recombinant gelatins and compositions thereof, and methods of producing and using the same.

24 Claims, 12 Drawing Sheets

LACTALBUMIN

SOYTONE rh-collagen TYPE I rh-collagen TYPE III

α1(I)   α1(I)      α2(I)   α2(I)
        +CNBr              +CNBr

FULL LENGTH α2(I) — α2(I) CB3+5

FRAGMENT OF α2(I) — α2(I) CB4 rhcI   α1(I)   α1(I)      α2(I)   α2(I)
               +CNBr               +CNBr

RECOMBINANT GELATINS

This application is a continuation of U.S. application Ser. No. 09/710,239, filed on 10 Nov. 2000, now U.S. Pat. No. 6,992,172, which claims the benefit of U.S. Provisional Application Nos. 60/204,437, filed 15 May 2000, and 60/165,114, filed 12 Nov. 1999, the specifications of which are incorporated herein by reference in their entireties.

FIELD OF THE INVENTION

This invention relates to recombinant gelatins and to compositions and agents comprising recombinant gelatins, to methods of producing recombinant gelatins, and to the use of these gelatins in various applications.

BACKGROUND OF THE INVENTION

Gelatin is a derivative of collagen, a principal structural and connective protein in animals. Gelatin is derived from denaturation of collagen and contains polypeptide sequences having Gly-X-Y repeats, where X and Y are most often proline and hydroxyproline residues. These sequences contribute to triple helical structure and affect the gelling ability of gelatin polypeptides. Currently available gelatin is extracted through processing of animal hides and bones, typically from bovine and porcine sources. The biophysical properties of gelatin make it a versatile material, widely used in a variety of applications and industries. Gelatin is used, for example, in numerous pharmaceutical and medical, photographic, industrial, cosmetic, and food and beverage products and processes of manufacture. Gelatin is thus a commercially valuable and versatile product.

Manufacture of Gelatin

Gelatin is typically manufactured from naturally occurring collagen in bovine and porcine sources, in particular, from hides and bones. In some instances, gelatin can be extracted from, for example, piscine, chicken, or equine sources. Raw materials of typical gelatin production, such as bovine hides and bones, originate from animals subject to government-certified inspection and passed fit for human consumption. There is concern over the infectivity of this raw material, due to the presence of contaminating agents such as transmissible spongiform encephalopathies (TSEs), particularly bovine spongiform encephalopathy (BSE), and scrapie, etc. (See, e.g., Rohwer, R. G. (1996), Dev Biol Stand 88:247-256.) Such issues are especially critical to gelatin used in pharmaceutical and medical applications.

Recently, concern about the safety of these materials, a significant portion of which are derived from bovine sources, has increased, causing various gelatin-containing products to become the focus of several regulatory measures to reduce the potential risk of transmission of bovine spongiform encephalopathy (BSE), linked to new variant Creutzfeldt-Jakob disease (nvCJD), a fatal neurological disease in humans. There is concern that purification steps currently used in the processing of extracting gelatin from animal tissues and bones may not be sufficient to remove the likelihood of infectivity due to contaminating SE-carrying tissue (i.e., brain tissue, etc.). U.S. and European manufacturers specify that raw material for gelatin to be included in animal or human food products or in pharmaceutical, medical, or cosmetic applications must not be obtained from a growing number of BSE countries. In addition, regulations specify that certain materials, e.g., bovine brain tissue, are not used in the production of gelatin.

Current production processes involve several purification and cleansing steps, and can require harsh and lengthy modes of extraction. The animal hides and bones are treated in a rendering process, and the extracted material is subjected to various chemical treatments, including prolonged exposure to highly acidic or alkaline solutions. Numerous purification steps can involve washing and filtration and various heat treatments. Acid demineralization and lime treatments are used to remove impurities such as non-collagenous proteins. Bones must be degreased. Additional washing and filtration steps, ion exchanges, and other chemical and sterilizing treatments are added to the process to further purify the material. Furthermore, contaminants and impurities can still remain after processing, and the resultant gelatin product must thus typically be clarified, purified, and often further concentrated before being ready for use.

Commercial gelatin is generally classified as type A or type B. These classifications reflect the pre-treatment extraction sources receive as part of the extraction process. Type A is generally derived from acid-processed materials, usually porcine hides, and type B is generally derived from alkaline- or lime-processed materials, usually bovine bones (ossein) and hides.

In extracting type A gelatin, the process generally involves subjecting fresh or frozen porcine hides to successive washings with water and treatments with dilute acids. The acid-treated skins are washed again and are then subject to repeated extraction steps in which they are treated with hot water, partially hydrolyzing the collagen present. The resultant extracts, dilute solutions of gelatin, are filtered and evaporated, and the resultant concentrates are allowed to cool or chilled to a gel. The gel is subsequently treated in drying tunnels, or by continuous dryers or other drying devices.

In the limed process, type B gelatin is derived from donor hides and skin trimmings washed and then treated with lime. The lime treatment can take as long as from one to three months, and is usually around sixty days. The limed hides are washed and treated with dilute acids. The hides are then hydrolyzed with hot water and the resulting extracts are processed as described above for the acid-treatment process.

Type B gelatin can also be processed from ossein sources. The hard bones are washed, degreased, and leached with successive treatments of dilute acids, such as hydrochloric acid. The acid treatment reacts with the mineral contents of bone, which are removed along with the acidic solution, leaving ossein, or demineralized bones. This organic bone matter, washed free of residual acid, is dried for storage or immediately limed. After liming, ossein is subsequently treated as described above for the production of gelatin from bovine hides. In all cases, after final filtering, demineralization, concentration, and drying steps, the resultant gelatin product is divided into batches, subjected to various physical, chemical, and bacteriological tests to determine grade and purity, and ground and blended according to commercial requirements. In both type A and B extraction processes, the resultant gelatin product typically comprises a mixture of gelatin molecules, in sizes of from a few thousand up to several hundred thousand Daltons.

Fish gelatin, classified as gelling or non-gelling types, and typically processed as Type A gelatin, is also used in certain commercial applications. Gelling types are usually derived from the skins of warm water fish, while non-gelling types are typically derived from cold water fish. Fish gelatins have widely varying amino acid compositions, and differ from animal gelatins in having typically lower proportions of proline and hydroxyproline residues. In contrast to animal gelatins, fish gelatins typically remain liquid at much lower temperatures, even at comparable average molecular weights. As with other animal gelatins, fish gelatin is extracted by treatment and subsequent hydrolyzation of fish skin. Again, as with animal extraction processes, the process of extracting fish gelatin results in a product that lacks homogeneity.

SUMMARY

Gelatin is an essential product used in wide-ranging applications. The diverse uses of gelatin rely on different characteristics and properties of this ubiquitous mixture of proteins. Current methods of extraction result in a gelatin product that is a heterogeneous mixture of proteins, containing polypeptides with molecular weight distributions of varying ranges. It is sometimes necessary to blend various lots of product in order to obtain a gelatin mixture with the physical properties appropriate for use in a desired application.

A more homogeneous product, and one produced by more reproducible means, would be desirable. The availability of a homogeneous material with reproducible physical characteristics would be desirable, for example, in various products and processes, where the availability of gelatin with specific characteristics, such as a fixed range of molecular weight, would allow for a reproducible and controlled performance. There is thus a need for a reliable and reproducible means of gelatin production that provides a homogeneous product with controlled characteristics.

In addition, in the pharmaceutical, cosmetic, and food and beverage industries, especially, there is a need for a source of gelatin other than that obtained through extraction from animal sources, e.g., bovine and porcine bones and tissues. Further, as currently available gelatin is manufactured from animal sources such as bones and tissues, there are concerns relating to the undesirable immunogenicity and infectivity of gelatin-containing products. (See, e.g., Sakaguchi, M. et al. (1999) J. Aller. Clin. Immunol. 104:695-699; Miyazawa et al. (1999) Vaccine 17:2176-2180; Sakaguchi et al. (1999) Immunology 96:286-290; Kelso (1999) J Aller. Clin Immunol. 103:200-202; Asher (1999) Dev Biol Stand 99:41-44; and Verdrager (1999) Lancet 354:1304-1305.) In addition, the availability of a substitute material that does not undergo extraction from animal sources, e.g., tissues and bones, will address various ethical, religious, and social dictates. A recombinant material that does not require extraction from animal sources, such as tissues and bones, could be used, for example, in the manufacture of foods and other ingested products, including encapsulated medicines, that are appropriate for use by people with dietary restrictions, for example, those who follow Kosher and Halal law.

While gelatin producers and end-users have searched for and tested a number of natural and synthetic substitutes for the animal-source gelatin currently available, a universal substitute has not yet been found. Alternatives have been identified for a few applications, such as the use of cellulosic raw materials in VCAPS capsules (CAPSUGEL; Morris Plains, N.J.), or the proposed use of non-natural gelatin-like proteins from mouse and rat collagen sequences in photographic emulsions. (See, e.g., Werten, M. W. et al. (1999) Yeast 15:1087-1096; and De Wolf, Anton et al., European Application No. EP1014176A2.) However, for most gelatin-based processes and products, the performance characteristics of this key material have not been duplicated, and substitutes have not been adopted. Thus, there is a need for a means of producing gelatin in a synthetic and reproducible manner wherein the resultant product can serve as a rational substitute with the desired performance characteristics.

In summary, there is a need for a universal replacement material that can provide performance characteristics of gelatin while allowing for a more reproducible and controlled source of product. There is a need for methods of producing gelatin that do not require harsh and lengthy processing, and for methods of manufacturing gelatin that result in a more uniform product and that are capable of stably producing significant amounts and different types of gelatin appropriate for diverse applications. There is a need for a versatile gelatin product that is readily adaptable for different uses and that answers existing health and other concerns.

The present invention solves these and other needs by providing a universal replacement material, obtained recombinantly, appropriate for use in the extraordinarily diverse spectrum of applications in which gelatin is currently used. The present materials can be designed to possess the properties and characteristics desired for particular applications, and can thus provide new properties and uses previously unavailable.

SUMMARY OF THE INVENTION

The present invention is directed to recombinant gelatins, to compositions and agents comprising recombinant gelatin, and to methods of producing and using recombinant gelatins.

In one aspect, the present invention provides a composition comprising recombinant gelatin. In one embodiment, the recombinant gelatin has a molecular weight selected from the group consisting of about 5 kDa, 8 kDa, 9 kDa, 14 kDa, 16 kDa, 22 kDa, 23 kDa, 36 kDa, 44 kDa, and 65 kDa. In another embodiment, the recombinant gelatin has a molecular weight range selected from the group consisting of about 0 to 50 kDa, about 10 to 30 kDa, about 30 to 50 kDa, about 10 to 70 kDa, about 50 kDa to 70 kDa about 50 to 100 kDa, about 100 to 150 kDa, about 150 to 200 kDa, about 200 to 250 kDa, about 250 to 300 kDa, and about 300 to 350 kDa. In one aspect, the recombinant gelatin has a molecular weight greater than 300 kDa.

In another aspect, the invention encompasses a recombinant gelatin having a Bloom strength selected from the group consisting of 50, 100, 150, 200, 250, and 300. In further embodiment, the Bloom strength is between 0 and 100.

In certain embodiments, the present invention provides a composition comprising recombinant gelatin wherein the recombinant gelatin is non-hydroxylated, fully hydroxylated, or partially hydroxylated. In various aspects, the recombinant gelatin has a percentage hydroxylation selected from the group consisting of 20 to 80%, 30 to 80%, 40 to 80%, 60 to 80%, 20 to 60%, 30 to 60%, 40 to 60%, 20 to 30%, 20 to 40%, and 30 to 40%. In other embodiments, the recombinant gelatin is fully hydrolyzed, partially hydrolyzed, or non-hydrolyzed.

In one aspect, the present invention provides a composition comprising recombinant gelatin, wherein the recombinant gelatin comprises a homogeneous mixture of recombinant gelatin polypeptides. In another aspect, the recombinant gelatin comprises a heterogeneous mixture of recombinant gelatin polypeptides.

In one embodiment, the present invention provides a composition comprising recombinant gelatin wherein the recombinant gelatin is derived from one type of collagen free of any other collagen. In particular embodiments, the one type of collagen is selected from the group consisting of type I, type II, type III, type IV, type V, type VI, type VII, type VIII, type IX, type X, type XI, type XII, type XIII, type XIV, type XV, type XVI, type XVII, type XVIII, type XIX, and type XX collagen. Compositions of recombinant gelatin wherein the recombinant gelatin has endotoxin levels of below 1.000 EU/mg, below 0.500 EU/mg, below 0.050 EU/mg, and below 0.005 EU/mg are contemplated.

In specific embodiments, the recombinant gelatin of the present invention comprises an amino acid sequence selected from the group consisting of SEQ ID NOs:15, 16, 17, 18, 19, 20, 21, 22, 23, 24, 25, 30, 31, and 33. Polynucleotides encoding these amino acid sequences are also provided, as are expression vectors and host cells containing the polynucleotides. In certain aspects, the host cells of the present invention are prokaryotic or eukaryotic. In one embodiment, a eukaryotic host cell is selected from the group consisting of a yeast cell, an animal cell, an insect cell, a plant cell, and a fungal cell. The present invention further provides transgenic animals and transgenic plants comprising the polynucleotides. Recombinant gelatins comprising an amino acid sequence selected from the group consisting of SEQ ID NOs: 26, 27, 28, and 29 are also provided.

In one aspect, the present invention encompasses methods of producing the recombinant gelatins. One method comprises providing recombinant collagen or procollagen or fragments or variants thereof; and processing the recombinant collagen or procollagen or fragments or variants thereof to produce recombinant gelatin. In one aspect, the recombinant collagen processed to recombinant gelatin is recombinant human collagen. In a further aspect, the recombinant collagen is produced by co-expressing at least one polynucleotide encoding a collagen or procollagen and at least one polynucleotide encoding a collagen post-translational enzyme or subunit thereof. In a certain embodiment, the post-translational enzyme is prolyl hydroxylase.

In another method according to the present invention, recombinant gelatin is produced directly from an altered collagen construct. In a further embodiment, the recombinant gelatin is produced by co-expressing the altered collagen construct and at least one polynucleotide encoding a post-translational enzyme or subunit thereof. In one embodiment, the post-translational enzyme is prolyl hydroxylase.

Methods of producing recombinant gelatins having selected melting temperatures are also provided. In one embodiment, the method comprises conferring on the recombinant gelatin a percentage hydroxylation that corresponds to the selected melting temperature. In a further embodiment, the conferring step comprises producing recombinant gelatin from an altered collagen construct in the presence of prolyl hydroxylase. In other aspects, the conferring step comprises deriving recombinant gelatin from hydroxylated recombinant collagen, or comprises hydroxylating non-hydroxylated recombinant gelatin.

Various uses of the recombinant gelatins of the present invention are contemplated. In particular, the present invention comprises encapsulants, stabilizing agents, film-forming agents, moisturizing agents, emulsifiers, thickening agents, gelling agents, colloidal agents, adhesive agents, flocculating agents, and refining agents comprising recombinant gelatin.

The present invention provides in one embodiment a pharmaceutical composition comprising recombinant gelatin. In a further embodiment, the recombinant gelatin is human recombinant gelatin. In another embodiment, the recombinant gelatin is non-immunogenic. In specific embodiments, the present invention provides a hard gel capsule, a soft gel capsule, a tablet coating, a plasma expander, a colloidal volume replacement material, a graft coating, a medical sponge, a medical plug, a pharmaceutical stabilizer, and a microcarrier comprising recombinant gelatin. In one aspect, the present invention encompasses a kit comprising a composition comprising recombinant gelatin, and a device for delivering the composition to a subject.

An edible composition comprising recombinant gelatin is also contemplated, as are protein supplements, fat substitutes, nutritional supplements, edible coatings, and various microencapsulants comprising recombinant gelatin. Photographic compositions comprising recombinant gelatin are also contemplated, as are embodiments in which recombinant gelatin is partially or fully hydroxylated. The invention further provides a cosmetic composition comprising recombinant gelatin.

In other embodiments, the invention encompasses a cosmetic composition comprising recombinant gelatin, an industrial composition comprising recombinant gelatin, a cell culture composition comprising recombinant gelatin, and a composition for laboratory use comprising recombinant gelatin. Further embodiments, such as microarrays comprising the recombinant gelatins of the present invention or polynucleotides encoding these recombinant gelatins, are contemplated.

DESCRIPTION OF THE INVENTION

Figure 1:
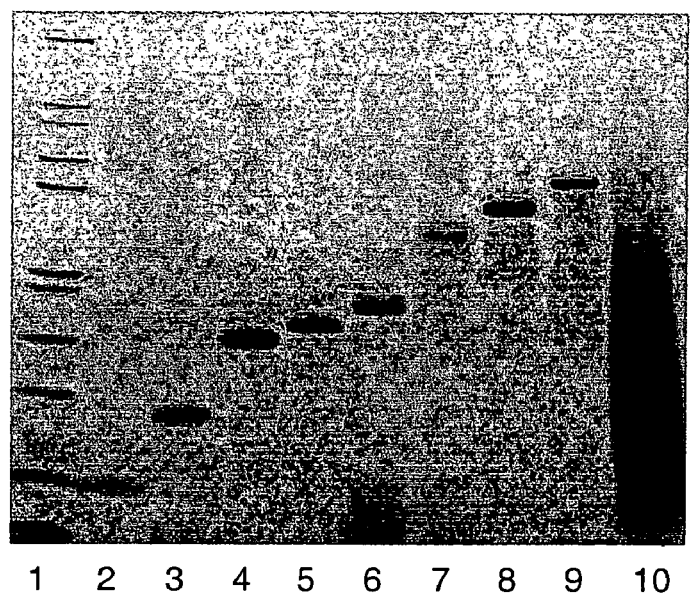
FIG. 1 sets forth results showing the expression of recombinant gelatins.

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention.

It must be noted that as used herein, and in the appended claims, the singular forms "a," "an," and "the" include plural reference unless the context clearly dictates otherwise. Thus, for example, reference to "a host cell" is reference to one or more of such host cells and equivalents thereof known to those skilled in the art, and reference to "an antibody" is a reference to one or more antibodies and equivalents thereof known to those skilled in the art, and so forth.

Unless defined otherwise, all technical and scientific terms used herein have the meanings as commonly understood by one of ordinary skill in the art to which the invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies, etc., which are reported in the publications which might be used in connection with the invention. Nothing herein is to be construed as an admission that the invention is not entitled to antedate such disclosure by virtue of prior invention. Each reference cited herein is incorporated herein by reference in its entirety.

The practice of the present invention will employ, unless otherwise indicated, conventional methods of chemistry, biochemistry, molecular biology, immunology and pharmacology, within the skill of the art. Such techniques are explained fully in the literature. See, e.g., Gennaro, A. R., ed. (1990) Remington's Pharmaceutical Sciences, $18^{th}$ ed., Mack Publishing Co.; Colowick, S. et al., eds., Methods In Enzymology, Academic Press, Inc.; Handbook of Experimental Immunology, Vols. I-IV (D. M. Weir and C. C. Blackwell, eds., 1986, Blackwell Scientific Publications); Maniatis, T. et al., eds. (1989) Molecular Cloning: A Laboratory Manual, $2^{nd}$ edition, Vols. I-III, Cold Spring Harbor Laboratory Press; Ausubel, F. M. et al., eds. (1999) Short Protocols in Molecular Biology, $4^{th}$ edition, John Wiley & Sons; Ream et al., eds. (1998) Molecular Biology Techniques: An Intensive Laboratory Course, Academic Press); PCR (Introduction to Biotechniques Series), 2nd ed. (Newton & Graham eds., 1997, Springer Verlag).

DEFINITIONS

The term "collagen" refers to any one of the known collagen types, including collagen types I through XX, as well as to any other collagens, whether natural, synthetic, semi-synthetic, or recombinant. The term also encompasses procollagens. The term collagen encompasses any single-chain polypeptide encoded by a single polynucleotide, as well as homotrimeric and heterotrimeric assemblies of collagen chains. The term "collagen" specifically encompasses variants and fragments thereof, and functional equivalents and derivatives thereof, which preferably retain at least one structural or functional characteristic of collagen, for example, a $(Gly-X-Y)_n$ domain.

The term "procollagen" refers to a procollagen corresponding to any one of the collagen types I through XX, as well as to a procollagen corresponding to any other collagens, whether natural, synthetic, semi-synthetic, or recombinant, that possesses additional C-terminal and/or N-terminal propeptides or telopeptides that assist in trimer assembly, solubility, purification, or any other function, and that then are subsequently cleaved by N-proteinase, C-proteinase, or other enzymes, e.g., proteolytic enzymes associated with collagen production. The term procollagen specifically encompasses variants and fragments thereof, and functional equivalents and derivatives thereof, which preferably retain at least one structural or functional characteristic of collagen, for example, a $(Gly-X-Y)_n$ domain.

"Gelatin" as used herein refers to any gelatin, whether extracted by traditional methods or recombinant or biosynthetic in origin, or to any molecule having at least one structural and/or functional characteristic of gelatin. Gelatin is currently obtained by extraction from collagen derived from animal (e.g., bovine, porcine, chicken, equine, piscine) sources, e.g., bones and tissues. The term gelatin encompasses both the composition of more than one polypeptide included in a gelatin product, as well as an individual polypeptide contributing to the gelatin material. Thus, the term recombinant gelatin as used in reference to the present invention encompasses both a recombinant gelatin material comprising the present gelatin polypeptides, as well as an individual gelatin polypeptide of the present invention.

Polypeptides from which gelatin can be derived are polypeptides such as collagens, procollagens, and other polypeptides having at least one structural and/or functional characteristic of collagen. Such a polypeptide could include a single collagen chain, or a collagen homotrimer or heterotrimer, or any fragments, derivatives, oligormers, polymers, or subunits thereof, containing at least one collagenous domain (a Gly-X-Y region). The term specifically contemplates engineered sequences not found in nature, such as altered collagen constructs, etc. An altered collagen construct is a polynucleotide comprising a sequence that is altered, through deletions, additions, substitutions, or other changes, from a naturally occurring collagen gene.

An "adjuvant" is any agent added to a drug or vaccine to increase, improve, or otherwise aid its effect. An adjuvant used in a vaccine formulation might be an immunological agent that improves the immune response by producing a non-specific stimulator of the immune response. Adjuvants are often used in non-living vaccines.

The terms "allele" or "allelic sequence" refer to alternative forms of genetic sequences. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" polynucleotide sequences include those with deletions, insertions, or substitutions of different nucleotides resulting in a polynucleotide that encodes the same or a functionally equivalent polypeptide. Included within this definition are sequences displaying polymorphisms that may or may not be readily detectable using particular oligonucleotide probes or through deletion of improper or unexpected hybridization to alleles, with a locus other than the normal chromosomal locus for the subject polynucleotide sequence.

"Altered" polypeptides may contain deletions, insertions, or substitutions of amino acid residues which produce a silent change and result in a functionally equivalent polypeptide. Deliberate amino acid substitutions may be made on the basis of similarity in polarity, charge, solubility, hydrophobicity, hydrophilicity, and/or the amphipathic nature of the residues as long as the biological or immunological activity of the encoded polypeptide is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid" or "polypeptide" sequences or "polypeptides," as these terms are used herein, refer to oligopeptide, peptide, polypeptide, or protein sequences, and fragments thereof, and to naturally occurring or synthetic molecules. Polypeptide or amino acid fragments are any portion of a polypeptide which retains at least one structural and/or functional characteristic of the polypeptide. In at least one embodiment of the present invention, polypeptide fragments are those retaining at least one $(Gly-X-Y)_n$ region.

The term "animal" as it is used in reference, for example, to "animal collagens" encompasses any collagens, derived from animal sources, whether natural, synthetic, semi-synthetic, or recombinant. Animal sources include, for example, mammalian sources, including, but not limited to, bovine, porcine, and ovine sources, and other animal sources, including, but not limited to, chicken and piscine, equine, rodent, and non-vertebrate sources.

"Antigenicity" relates to the ability of a substance to, when introduced into the body, stimulate the immune response and the production of an antibody. An agent displaying the property of antigenicity is referred to as being antigenic. Antigenic agents can include, but are not limited to, a variety of macromolecules such as, for example, proteins, lipoproteins, polysaccharides, nucleic acids, bacteria and bacterial components, and viruses and viral components.

The terms "complementary" or "complementarity," as used herein, refer to the natural binding of polynucleotides by base-pairing. For example, the sequence "A-G-T" binds to the complementary sequence "T-C-A." Complementarity between two single-stranded molecules may be "partial," when only some of the nucleic acids bind, or may be complete, when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands, and in the design and use, for example, of peptide nucleic acid (PNA) molecules.

A "deletion" is a change in an amino acid or nucleotide sequence that results in the absence of one or more amino acid residues or nucleotides.

The term "derivative," as applied to polynucleotides, refers to the chemical modification of a polynucleotide encoding a particular polypeptide or complementary to a polynucleotide encoding a particular polypeptide. Such modifications include, for example, replacement of hydrogen by an alkyl, acyl, or amino group. As used herein to refer to polypeptides, the term "derivative" refers to a polypeptide which is modified, for example, by hydroxylation, glycosylation, pegylation, or by any similar process. The term "derivatives" encompasses those molecules containing at least one structural and/or functional characteristic of the molecule from which it is derived.

A molecule is said to be a "chemical derivative" of another molecule when it contains additional chemical moieties not normally a part of the molecule. Such moieties can improve the molecule's solubility, absorption, biological half-life, and the like. The moieties can alternatively decrease the toxicity of the molecule, eliminate or attenuate any undesirable side effect of the molecule, and the like. Moieties capable of mediating such effects are generally available in the art and can be found for example, in *Remington's Pharmaceutical Sciences*, supra. Procedures for coupling such moieties to a molecule are well known in the art.

An "excipient" as the term is used herein is any inert substance used as a diluent or vehicle in the formulation of a drug, a vaccine, or other pharmaceutical composition, in order to confer a suitable consistency or form to the drug, vaccine, or pharmaceutical composition.

The term "functional equivalent" as it is used herein refers to a polypeptide or polynucleotide that possesses at least one functional and/or structural characteristic of a particular polypeptide or polynucleotide. A functional equivalent may contain modifications that enable the performance of a specific function. The term "functional equivalent" is intended to include fragments, mutants, hybrids, variants, analogs, or chemical derivatives of a molecule.

A "fusion protein" is a protein in which peptide sequences from different proteins are operably linked.

The term "hybridization" refers to the process by which a nucleic acid sequence binds to a complementary sequence through base pairing. Hybridization conditions can be defined by, for example, the concentrations of salt or formamide in the prehybridization and hybridization solutions, or by the hybridization temperature, and are well known in the art. Hybridization can occur under conditions of various stringency.

In particular, stringency can be increased by reducing the concentration of salt, increasing the concentration of formamide, or raising the hybridization temperature. For example, for purposes of the present invention, hybridization under high stringency conditions occurs in about 50% formamide at about 37° C. to 42° C., and under reduced stringency conditions in about 35% to 25% formamide at about 30° C. to 35° C. In particular, hybridization occurs in conditions of highest stringency at 42° C. in 50% formamide, 5×SSPE, 0.3% SDS, and 200 µg/ml sheared and denatured salmon sperm DNA.

The temperature range corresponding to a particular level of stringency can be further narrowed by methods known in the art, for example, by calculating the purine to pyrimidine ratio of the nucleic acid of interest and adjusting the temperature accordingly. To remove nonspecific signals, blots can be sequentially washed, for example, at room temperature under increasingly stringent conditions of up to 0.1×SSC and 0.5% SDS. Variations on the above ranges and conditions are well known in the art.

"Immunogenicity" relates to the ability to evoke an immune response within an organism. An agent displaying the property of immunogenicity is referred to as being immunogenic. Agents can include, but are not limited to, a variety of macromolecules such as, for example, proteins, lipoproteins, polysaccharides, nucleic acids, bacteria and bacterial components, and viruses and viral components. Immunogenic agents often have a fairly high molecular weight (usually greater than 10 kDa).

"Infectivity" refers to the ability to be infective or the ability to produce infection, referring to the invasion and multiplication of microorganisms, such as bacteria or viruses within the body.

The terms "insertion" or "addition" refer to a change in a polypeptide or polynucleotide sequence resulting in the addition of one or more amino acid residues or nucleotides, respectively, as compared to the naturally occurring molecule.

The term "isolated" as used herein refers to a molecule separated not only from proteins, etc., that are present in the natural source of the protein, but also from other components in general, and preferably refers to a molecule found in the presence of, if anything, only a solvent, buffer, ion, or other component normally present in a solution of the same. As used herein, the terms "isolated" and "purified" do not encompass molecules present in their natural source.

The term "microarray" refers to any arrangement of nucleic acids, amino acids, antibodies, etc., on a substrate. The substrate can be any suitable support, e.g., beads, glass, paper, nitrocellulose, nylon, or any appropriate membrane, etc. A substrate can be any rigid or semi-rigid support including, but not limited to, membranes, filters, wafers, chips, slides, fibers, beads, including magnetic or nonmagnetic beads, gels, tubing, plates, polymers, microparticles, capillaries, etc. The substrate can provide a surface for coating and/or can have a variety of surface forms, such as wells, pins, trenches, channels, and pores, to which the nucleic acids, amino acids, etc., may be bound.

The term "microorganism" can include, but is not limited to, viruses, bacteria, Chlamydia, rickettsias, mycoplasmas, ureaplasmas, fungi, and parasites, including infectious parasites such as protozoans.

The terms "nucleic acid" or "polynucleotide" sequences or "polynucleotides" refer to oligonucleotides, nucleotides, or polynucleotides, or any fragments thereof, and to DNA or RNA of natural or synthetic origin which may be single- or double-stranded and may represent the sense or antisense strand, to peptide nucleic acid (PNA), or to any DNA-like or RNA-like material, natural or synthetic in origin. Polynucleotide fragments are any portion of a polynucleotide sequence that retains at least one structural or functional characteristic of the polynucleotide. In one embodiment of the present invention, polynucleotide fragments are those that encode at least one $(Gly-X-Y)_n$ region. Polynucleotide fragments can be of variable length, for example, greater than 60 nucleotides in length, at least 100 nucleotides in length, at least 1000 nucleotides in length, or at least 10,000 nucleotides in length.

The phrase "percent similarity" (% similarity) refers to the percentage of sequence similarity found in a comparison of two or more polypeptide or polynucleotide sequences. Percent similarity can be determined by methods well-known in the art. For example, percent similarity between amino acid sequences can be calculated using the clustal method. (See, e.g., Higgins, D. G. and P. M. Sharp (1988) Gene 73:237-244.) The algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no homology between the two amino acid sequences are not included in determining percentage similarity. Percent similarity can be calculated by other methods known in the art, for example, by varying hybridization conditions, and can be calculated electronically using programs such as the MEGALIGN program (DNASTAR Inc., Madison, Wis.).

As used herein, the term "plant" includes reference to one or more plants, i.e., any eukaryotic autotrophic organisms such as angiosperms and gymnosperms, monotyledons and dicotyledons, including, but not limited to, soybean, cotton, alfalfa, flax, tomato, sugar, beet, sunflower, potato, tobacco, maize, wheat, rice, lettuce, banana, cassava, safflower, oilseed, rape, mustard, canola, hemp, algae, kelp, etc. The term "plant" also encompasses one or more plant cells. The term "plant cells" includes, but is not limited to, vegetative tissues and organs such as seeds, suspension cultures, embryos, meristematic regions, callus tissue, leaves, roots, shoots, gametophytes, sporophytes, pollen, tubers, corms, bulbs, flowers, fruits, cones, microspores, etc.

The term "post-translational enzyme" refers to any enzyme that catalyzes post-translational modification of, for example, any collagen or procollagen. The term encompasses, but is not limited to, for example, prolyl hydroxylase, peptidyl prolyl isomerase, collagen galactosyl hydroxylysyl glucosyl transferase, hydroxylysyl galactosyl transferase, C-proteinase, N-proteinase, lysyl hydroxylase, and lysyl oxidase.

As used herein, the term "promoter" generally refers to a regulatory region of nucleic acid sequence capable of initiating, directing, and mediating the transcription of a polynucleotide sequence. Promoters may additionally comprise recognition sequences, such as upstream or downstream promoter elements, which may influence the transcription rate.

The term "non-constitutive promoters" refers to promoters that induce transcription via a specific tissue, or may be otherwise under environmental or developmental controls, and includes repressible and inducible promoters such as tissue-preferred, tissue-specific, and cell type-specific promoters. Such promoters include, but are not limited to, the AdH1 promoter, inducible by hypoxia or cold stress, the Hsp70 promoter, inducible by heat stress, and the PPDK promoter, inducible by light.

Promoters which are "tissue-preferred" are promoters that preferentially initiate transcription in certain tissues. Promoters which are "tissue-specific" are promoters that initiate transcription only in certain tissues. "Cell type-specific" promoters are promoters which primarily drive expression in certain cell types in at least one organ, for example, vascular cells.

"Inducible" or "repressible" promoters are those under control of the environment, such that transcription is effected, for example, by an environmental condition such as anaerobic conditions, the presence of light, biotic stresses, etc., or in response to internal, chemical, or biological signals, e.g., glyceraldehyde phosphate dehydrogenase, AOX1 and AOX2 methanol-inducible promoters, or to physical damage.

As used herein, the term "constitutive promoters" refers to promoters that initiate, direct, or mediate transcription, and are active under most environmental conditions and states of development or cell differentiation. Examples of constitutive promoters, include, but are not limited to, the cauliflower mosaic virus (CaMv) 35S, the 1'- or 2'-promoter derived from T-DNA of *Agrobacteriuam tumefaciens*, the ubiquitin 1 promoter, the Smas promoter, the cinnamyl alcohol dehydrogenase promoter, glyceraldehyde dehydrogenase promoter, and the Nos promoter, etc.

The term "purified" as it is used herein denotes that the indicated molecule is present in the substantial absence of other biological macromolecules, e.g., polynucleotides, proteins, and the like. The term preferably contemplates that the molecule of interest is present in a solution or composition at least 80% by weight; preferably, at least 85% by weight; more preferably, at least 95% by weight; and, most preferably, at least 99.8% by weight. Water, buffers, and other small molecules, especially molecules having a molecular weight of less than about one kDa, can be present.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution" is the replacement of one or more amino acids or nucleotides by different amino acids or nucleotides, respectively.

The term "transfection" as used herein refers to the process of introducing an expression vector into a cell. Various transfection techniques are known in the art, for example, microinjection, lipofection, or the use of a gene gun.

"Transformation", as defined herein, describes a process by which exogenous nucleic acid sequences, e.g., DNA, enters and changes a recipient cell. Transformation may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome, and also include cells which transiently express the inserted nucleic acid for limited periods of time.

As used herein, the term "vaccine" refers to a preparation of killed or modified microorganisms, living attenuated organisms, or living fully virulent organisms, or any other agents, including, but not limited to peptides, proteins, biological macromolecules, or nucleic acids, natural, synthetic, or semi-synthetic, administered to produce or artificially increase immunity to a particular disease, in order to prevent future infection with a similar entity. Vaccines can contain live, or inactive microorganisms, or other agents, including viruses and bacteria, as well as subunit, synthetic, semi-synthetic, or recombinant DNA-based.

Vaccines can be monovalent (a single strain/microorganism/disease vaccine) consisting of one microorganism or agent (e.g., poliovirus vaccine) or the antigens of one microorganism or agent. Vaccines can also be multivalent, e.g., divalent, trivalent, etc. (a combined vaccine), consisting of more than one microorganism or agent (e.g., a measles-mumps-rubella (MMR) vaccine) or the antigens of more than one microorganism or agent.

Live vaccines are prepared from living microorganisms. Attenuated vaccines are live vaccines prepared from microorganisms which have undergone physical alteration (such as radiation or temperature conditioning) or serial passage in laboratory animal hosts or infected tissue/cell cultures, such treatments producing avirulent strains or strains of reduced virulence, but maintaining the capability of inducing protective immunity. Examples of live attenuated vaccines include measles, mumps, rubella, and canine distemper. Inactivated vaccines are vaccines in which the infectious microbial components have been destroyed, e.g., by chemical or physical treatment (such as formalin, beta-propiolactone, or gamma radiation), without affecting the antigenicity or immunogenicity of the viral coat or bacterial outer membrane proteins. Examples of inactivated or subunit vaccines include influenza, Hepatitis A, and poliomyelitis (IPV) vaccines.

Subunit vaccines are composed of key macromolecules from, e.g., the viral, bacterial, or other agent responsible for eliciting an immune response. These components can be obtained in a number of ways, for example, through purification from microorganisms, generation using recombinant DNA technology, etc. Subunit vaccines can contain synthetic mimics of any infective agent. Subunit vaccines can include macromolecules such as bacterial protein toxins (e.g., tetanus, diphtheria), viral proteins (e.g., from influenza virus), polysaccharides from encapsulated bacteria (e.g., from *Haemophilus influenzae* and *Streptococcus pneumonia*), and viruslike particles produced by recombinant DNA technology (e.g., hepatitis B surface antigen), etc.

Synthetic vaccines are vaccines made up of small synthetic peptides that mimic the surface antigens of pathogens and are immunogenic, or may be vaccines manufactured with the aid of recombinant DNA techniques, including whole viruses whose nucleic acids have been modified.

Semi-synthetic vaccines, or conjugate vaccines, consist of polysaccharide antigens from microorganisms attached to protein carrier molecules.

DNA vaccines contain recombinant DNA vectors encoding antigens, which, upon expression of the encoded antigen in host cells having taken up the DNA, induce humoral and cellular immune responses against the encoded antigens.

Vaccines have been developed for a variety of infectious agents. The present invention is directed to recombinant gelatins that can be used in vaccine formulations regardless of the agent involved, and are thus not limited to use in the vaccines specifically described herein by way of example. Vaccines include, but are not limited to, vaccines for vacinnia virus (small pox), polio virus (Salk and Sabin), mumps, measles, rubella, diphtheria, tetanus, Varicella-Zoster (chicken pox/shingles), pertussis (whopping cough), Bacille Calmette-Guerin (BCG, tuberculosis), *haemophilus influenzae* meningitis, rabies, cholera, Japanese encephalitis virus, *salmonella typhi, shigella,* hepatitis A, hepatitis B, adenovirus, yellow fever, foot-and-mouth disease, herpes simplex virus, respiratory syncytial virus, rotavirus, Dengue, West Nile virus, Turkey herpes virus (Marek's Disease), influenza, and anthrax. The term vaccine as used herein includes reference to vaccines to various infectious and autoimmune diseases and cancers that have been or that will be developed, for example, vaccines to various infectious and autoimmune diseases and cancers, e.g., vaccines to HIV, HCV, malaria, and vaccines to breast, lung, colon, renal, bladder, and ovarian cancers.

A polypeptide or amino acid "variant" is an amino acid sequence that is altered by one or more amino acids from a particular amino acid sequence. A polypeptide variant may have conservative changes, wherein a substituted amino acid has similar structural or chemical properties to the amino acid replaced, e.g., replacement of leucine with isoleucine. A variant may also have nonconservative changes, in which the substituted amino acid has physical properties different from those of the replaced amino acid, e.g., replacement of a glycine with a tryptophan. Analogous minor variations may also include amino acid deletions or insertions, or both. Preferably, amino acid variants retain certain structural or functional characteristics of a particular polypeptide. Guidance in determining which amino acid residues may be substituted, inserted, or deleted may be found, for example, using computer programs well known in the art, such as LASERGENE software (DNASTAR Inc., Madison, Wis.).

A polynucleotide variant is a variant of a particular polynucleotide sequence that preferably has at least about 80%, more preferably at least about 90%, and most preferably at least about 95% polynucleotide sequence similarity to the particular polynucleotide sequence. It will be appreciated by those skilled in the art that as a result of the degeneracy of the genetic code, a multitude of variant polynucleotide sequences encoding a particular protein, some bearing minimal homology to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard codon triplet genetic code, and all such variations are to be considered as being specifically disclosed.

INVENTION

The present invention provides recombinant gelatins and methods for producing these gelatins. The recombinant gelatins of the present invention provide consistent and improved performance, and are able to address various health and other concerns. Using the present methods, gelatin can be directly manufactured, rather than extracted from animal sources through lengthy and harsh processes. The recombinant gelatin of the present invention is free of pathogens, for example, pathogenic bacteria, transmissible spongiform encephalopathies (TSEs), etc. The present methods minimize variability and allow for a degree of reproducibility unattainable in current extraction methods.

Safety issues, such as concern over potential immunogenic, e.g., antigenic and allergenic, responses, have arisen regarding the use of animal-derived products. The inability to completely characterize, purify, or reproduce animal-source gelatin mixtures used currently is of ongoing concern in the pharmaceutical and medical communities. Additional safety concerns exist with respect to bacterial contamination and endotoxin loads resulting from the extraction and purification processes.

The recombinant gelatins of the present invention address these concerns as they are virtually free of bacterial contamination or endotoxins. Furthermore, the recombinant human gelatins of the present invention will offer distinct advantages over animal-derived counterparts currently in use, as the use of gelatins derived from native human sequence can eliminate the risk of immune response due to the use of non-human, animal-derived proteins.

In addition, the present gelatins can be produced as various and distinct materials, with characteristics optimized for particular applications. The resultant products are internally more consistent and uniform than are currently available gelatins derived from animal sources.

In one embodiment, the present invention provides a recombinant gelatin. The gelatin can be produced using sequences from various species including, but not limited to, human, bovine, porcine, equine, rodent, chicken, ovine, and piscine species, or from non-vertebrate species. The gelatin of the present invention has increased purity as compared to the gelatin products of current methods of manufacture, and has a reduced protein load and reduced levels of endotoxins and other contaminants, including nucleic acids, polysaccharides, prions, etc. The present gelatin is thus safer to use than gelatin manufactured by current methods, and can be administered to or ingested by humans and animals at a higher dosage while minimizing the risk of negative side effects.

The gelatins of the present invention have increased activity and workability compared to commercial gelatins, as the present gelatin can be produced directly with characteristics optimized for specific uses, improving one's ability to use and formulate the gelatin. While gelatins currently extracted from animal sources are heterogeneous products with a wide range in molecular weights throughout a given batch or sample, the gelatins of the present invention include consistent, homogeneous, and reproducible products.

The recombinant gelatins of the present invention can be produced using a variety of methods. In one method, the recombinant gelatin is produced through processing of recombinant collagen. (See, e.g., Examples 9, 10, and 11.) In another method, the recombinant gelatin is produced directly from the expression of altered collagen constructs, i.e., constructs containing a polynucleotide encoding at least one collagenous domain, but not encoding naturally occurring collagen. (See, e.g., Examples 1, 4, and 6.) In another aspect, the recombinant gelatin is derived from polypeptides which are not full-length naturally occurring collagen or procollagen, but which contain at least one collagenous domain. (See, e.g., SEQ ID NOs:15 through 25, 30, 31, and 33.) Recombinant gelatins can also comprise sequences containing additional N-terminal or C-terminal propeptides. (See, e.g., SEQ ID NOs:26 through 29.)

In one aspect, the recombinant gelatin of the present invention is derived from recombinant collagens or procollagens. Collagen molecules generally result from trimeric assembly of polypeptide chains containing (Gly-X-Y-)$_n$ repeats which allow for the formation of triple helical domains under normal biological conditions. (See, e.g., van der Rest et al., (1991), FASEB J. 5:2814-2823.) At present, about twenty distinct collagen types have been identified in vertebrates, including bovine, ovine, porcine, chicken and human collagens. A detailed description of structure and biological functions of the various types of naturally occurring collagens can be found, among other places, in Ayad et al., The Extracellular Matrix Facts Book, Academic Press, San Diego, Calif.; Burgeson, R. E., and Nimmi (1992) "Collagen types: Molecular Structure and Tissue Distribution," Clin. Orthop. 282:250-272; Kielty, C. M. et al. (1993) "The Collagen Family: Structure, Assembly And Organization In The Extracellular Matrix," in Connective Tissue And Its Heritable Disorders, Molecular Genetics, And Medical Aspects, Royce, P. M. and Steinmann, B., Eds., Wiley-Liss, NY, pp. 103-147; and Prockop and Kivirikko (1995) "Collagens: Molecular biology, diseases, and potentials for therapy", Annu Rev Biochem 64:403-434.

Type I collagen is the major fibrillar collagen of bone and skin, comprising approximately 80-90% of an organism's total collagen. Type I collagen is the major structural macromolecule present in the extracellular matrix of multicellular organisms and comprises approximately 20% of total protein mass. Type I collagen is a heterotrimeric molecule comprising two α1(I) chains and one α2(I) chain, which are encoded by the COL1A1 and COL1A2 genes, respectively. Other collagen types are less abundant than type I collagen and exhibit different distribution patterns. For example, type II collagen is the predominant collagen in cartilage and vitreous humor, while type III collagen is found at high levels in blood vessels and to a lesser extent in skin.

Type III collagen is a major fibrillar collagen found in skin and vascular tissues. Type III collagen is a homotrimeric collagen comprising three identical α1(III) chains encoded by the COL3A1 gene. Methods for purifying various collagens from tissues can be found, for example, in, Byers et al. (1974) Biochemistry 13:5243-5248; and Miller and Rhodes (1982) Methods in Enzymology 82:33-64.

Post-translational enzymes are important to the biosynthesis of procollagens and collagens. For example, prolyl 4-hydroxylase is a post-translational enzyme necessary for the synthesis of procollagen or collagen by cells. This enzyme hydroxylates prolyl residues in the Y-position of repeating Gly-X-Y sequences to 4-hydroxyproline. (See, e.g., Prockop et al. (1984) N. Engl. J. Med. 311:376-386.) Unless an appropriate number of Y-position prolyl residues are hydroxylated to 4-hydroxyproline by prolyl 4-hydroxylase, the newly synthesized chains cannot maintain a stable triple-helical conformation. Moreover, if no hydroxylation or under-hydroxylation occurs, the polypeptides are not secreted properly and may be degenerated.

Vertebrate prolyl 4-hydroxylase is an $\alpha_2\beta_2$ tetramer. (See, e.g. Berg and Prockop (1973) J. Biol. Chem. 248:1175-1192; and Tuderman et al. (1975) Eur. J. Biochem. 52:9-16.) The $\alpha$ subunits contain the catalytic sites involved in the hydroxylation of prolyl residues, but are insoluble in the absence of $\beta$ subunits. The $\beta$ subunits, protein disulfide isomerases, catalyze thiol/disulfide interchanges, leading to formation of disulfide bonds essential to establishing a stable protein. The $\beta$ subunits retain 50% of protein disulfide isomerase activity when part of the prolyl 4-hydroxylase tetramer. (See, e.g., Pihlajaniemi et al. (1987) Embo J. 6:643-649; Parkkonen et al. (1988) Biochem. J. 256:1005-1011; and Koivu et al. (1987) J. Biol. Chem. 262:6447-6449.)

Active recombinant human prolyl 4-hydroxylase has been produced in, e.g., Sf9 insect cells and in yeast cells, by simultaneously expressing the $\alpha$ and $\beta$ subunits. (See, e.g., Vuori et al. (1992) Proc. Natl. Acad. Sci. USA 89:7467-7470; U.S. Pat. No. 5,593,859.) In addition to prolyl 4-hydroxylase, other collagen post-translational enzymes have been identified and reported in the literature, including C-proteinase, N-proteinase, lysyl oxidase, lysyl hydroxylase, etc. (See, e.g., Olsen et al. (1991) *Cell Biology of Extracellular Matrix, 2nd* ed., Hay editor, Plenum Press, New York.)

The present invention specifically contemplates the use of any compound, biological or chemical, that confers hydroxylation, e.g., proline hydroxylation and/or lysyl hydroxylation, etc., as desired, to the present recombinant gelatins. This includes, for example, prolyl 4-hydroxylase from any species, endogenously or exogenously supplied, including various isoforms of prolyl 4-hydroxylase and any variants or fragments or subunits of prolyl 4-hydroxylase having the desired activity, whether native, synthetic, or semi-synthetic, and other hydroxylases such as prolyl 3-hydroxylase, etc. (See, e.g., U.S. Pat. No. 5,928,922, incorporated by reference herein in its entirety.) In one embodiment, the prolyl hydroxylase activity is conferred by a prolyl hydroxylase derived from the same species as the polynucleotide encoding recombinant gelatin or encoding a polypeptide from which recombinant gelatin can be derived. In a further embodiment, the prolyl 4-hydroxylase is human and the encoding polynucleotide is derived from human sequence.

The present invention provides methods for manipulating the thermoplasticity of gelatin in order to produce a material with the desired physical characteristics. In one method, the encoding polynucleotides are expressed in a host system having endogenous prolyl hydroxylase or alternate hydroxylases, such as certain mammalian or insect cells, or transgenic animals, or plants or plant cells. In such a system, the present invention provides methods for producing a mixture of recombinant gelatins having a range of percentages of hydroxylation, i.e., non-hydroxylated, partially hydroxylated, and fully hydroxylated portions. For example, in one method of producing recombinant gelatins with varying percentages of hydroxylation, the hydroxylation is conferred by endogenous prolyl hydroxylase in, e.g., a transgenic animal, and the distribution of percentage hydroxylation ranges from non-hydroxylated to fully-hydroxylated, and the melting temperatures of the material produced range from 28° C. to 36° C., with a median $T_m$ value of around 30° C. to 32° C. If desired, different fractions of the material can be isolated along a temperature gradient, as might be necessary if downstream uses require selecting, for example, the more fully hydroxylated materials, such as those sufficiently hydroxylated to retain triple helical structure at, e.g., body temperature (37° C.).

In another embodiment, recombinant gelatins are produced in a system, e.g., a transgenic animal, in which hydroxylation is supplemented with exogenous prolyl hydroxylase. In one aspect, such a method of producing recombinant gelatins provides recombinant gelatins ranging from non-hydroxylated to fully-hydroxylated. The fraction of recombinant gelatins more fully hydroxylated will be substantially larger in recombinant material produced in the presence of exogenous prolyl hydroxylase than in recombinant material produced only in the presence of endogenous prolyl hydroxylase. Therefore, the melting temperatures of the material produced can range from, for example, 28° C. to 40° C., having a median $T_m$ value of around 34° C. to 36° C. Such a gelatin mixture could be appropriate for use in a variety of applications, such as gel capsule manufacture, without requiring any fractionation or separation of differently hydroxylated portions.

The above methods provide for production of recombinant materials with a range of melting temperatures, that can be easily divided, for example, using a temperature gradient to separate materials solid at a particular temperature, e.g., 36° C., from those liquid at a particular temperature. Furthermore, the present invention provide for cost-effective methods of producing a material which, without separation, is suitable for use in bulk applications. For example, the manufacture of gel capsules could involve the use of recombinant gelatin produced by the above methods, wherein the recombinant material, having a range of melting temperatures, had a desirable melting temperature of around 33° C., such gelatin melting at body temperatures, and thus being suitable for swallowing and digestion. In the present methods, the recombinant gelatin can be produced directly in the desired system, e.g., a transgenic animal, or can be derived, for example, through hydrolysis, e.g., acid, thermal, or enzymatic, from recombinant collagens produced in the desired system.

In one embodiment, the present invention provides a method of producing recombinant gelatin comprising producing recombinant collagen and deriving recombinant gelatin from the recombinant collagen. In one aspect, the method comprises the expression of at least one polynucleotide sequence encoding a collagen or procollagen, or fragment or variant thereof, and at least one polynucleotide encoding a collagen post-translational enzyme or a subunit thereof. (See, e.g., U.S. Pat. No. 5,593,859, incorporated by reference herein in its entirety.) The present recombinant gelatins can be derived from recombinant collagens using procedures known in the art. (See, e.g., Veis (1965) Int Rev Connect Tissue Res, 3:113-200.) For example, a common feature of all collagen-to-gelatin extraction processes is the loss of the secondary structure of the collagen protein, and in the majority of instances, an alteration in collagen structure. The collagens used in producing the gelatins of the present invention can be processed using different procedures depending on the type of gelatin desired.

Gelatin of the present invention can be derived from recombinantly produced collagen, or procollagens or other collagenous polypeptides, or from cell cultures, e.g., vertebrate cell cultures, by a variety of methods known in the art. For example, gelatin may be derived directly from the cell mass or the culture medium by taking advantage of gelatin's solubility at elevated temperatures and its stability under conditions of low or high pH, low or high salt concentrations, and high temperatures. Methods, processes, and techniques of producing gelatin compositions from collagen include digestion with proteolytic enzymes at elevated temperatures, denaturing the triple helical structure of the collagen utilizing detergents, heat, or various denaturing agents well known in the art, etc. In addition, various steps involved in the extraction of gelatin from animal or slaughterhouse sources, including treatment with lime or acids, heat extraction in aqueous solution, ion exchange chromatography, cross-flow filtration, and various methods of drying can be used to derive the gelatin of the present invention from recombinant collagen.

In one aspect, the gelatin of the present invention is comprised of denatured triple helices, and comprises at least one collagen subunit, collagen chain, or fragment thereof. The Gly-X-Y units within a particular collagen chain, subunit, or fragment thereof may be the same or different. Preferably, X and Y are either proline or hydroxyproline, and glycine appears in about every third residue position of the component chain. The amino acids of X and Y are proline or hydroxyproline, and each Gly-X-Y unit is the same or different. In another embodiment, the recombinant gelatin of the present invention comprises an amino acid sequence of $(Gly-X-Y)_n$, wherein X and Y are any amino acid.

In one embodiment, the present gelatin is derived from a recombinant collagen of one type that is substantially free from collagen of any other collagen type. In one aspect, the recombinant collagen is type I collagen. In another aspect, the recombinant collagen is type III collagen. In another embodiment of the present invention, the recombinant collagen is human recombinant collagen. Further embodiments of the invention, in which the recombinant collagen is of any one collagen type, such as any one of collagen types I through XX, inclusively, or any other collagen, natural, synthetic, or semi-synthetic, are specifically contemplated. Embodiments in which the recombinant gelatin is derived from specified mixtures of any one or more of any of collagen types I through XX, inclusively, or any other collagen, natural, synthetic, or semi-synthetic, are specifically contemplated.

The present methods of producing recombinant gelatin have a number of advantages over traditional methods of gelatin extraction. Most importantly, the present methods provide a reliable non-tissue source of gelatin containing native collagen sequence. In addition, current methods of extraction do not allow for any natural source of human gelatin, such as might be advantageous for use in various medical applications. The present invention specifically provides recombinant gelatins derived from human sequences, compositions comprising recombinant human gelatins, and methods of producing these gelatins. The recombinant human gelatin is non-immunogenic as applied in pharmaceutical and medical processes, and various uses thereof are also contemplated.

In another aspect, the present invention provides for the production of the present gelatin from engineered constructs capable of expressing gelatin in various forms. This invention specifically contemplates methods of producing gelatin using recombinant prolyl hydroxylase and various synthetic constructs, including non-native collagen constructs. Further, the present invention provides recombinant gelatins that can be designed to possess the specific characteristics needed for a particular application. Methods for producing these gelatins are also contemplated. Using the current methods, one could produce a gelatin with the desired gel strength, viscosity, melting characteristics, isoelectric profile, pH, degree of hydroxylation, amino-acid composition, odor, color, etc. In one method according to the present invention, non-hydrolyzed gelatin is produced, and can be subsequently hydrolyzed fully or partially, if desired.

Properties of Gelatin

The various physical properties of gelatin define its usefulness in particular applications. Gelatin provides unique performance based on, for example, its amphoteric nature, its ability to form thermo-reversible gels, its protective colloidal and surface active properties, and its contribution to viscosity and stability. In a number of applications, gelatin is used, for example, as an emulsifier, thickener, or stabilizer; as an agent for film or coating formation; as a binding agent; as an adhesive or glue; or as a flocculating agent.

Raw materials, types of pre-treatment, and extraction processes all effect the composition of gelatin polypeptides obtained during conventional manufacture. Currently available animal products are thus heterogeneous protein mixtures of polypeptide chains. Gelatin molecules can be fairly large, with the molecular weight within a particular sample ranging from a few to several hundred kDa. The molecular weight distribution of gelatin in a particular lot can be critical, as weight distribution can influence, for example, the viscosity and/or gel strength of a gelatin sample.

In general, the viscosity of a gelatin solution increases with increasing concentration and with decreasing temperature. A higher viscosity solution would be preferred, for example, for gelatin used as a stabilizer or thickener. In some applications, liquid gelatins are preferred, such as in various emulsifying fluids, etc. Viscosity of a gelatin solution increases with increasing molecular weight of the gelatin components. A high-viscosity gelatin solution could consist, therefore, of a high concentration of low molecular weight gelatins, or of a lower concentration of high molecular weight gelatins. Viscosity also affects gel properties including setting and melting point. High-viscosity gelatin solutions provide gels with higher melting and setting rates than do lower viscosity gelatin solutions.

The thermoreversibility and thermoplasticity of gelatin are properties exploited in a number of applications, for example, in the manufacture of gel capsules and tablets. Gelatin can be heated, molded or shaped as appropriate, and cooled to form a capsule or tablet coating that has unique properties at homeostatic temperatures. The gelatin will begin to melt at mouth temperature, easing swallowing, and become liquid at body temperatures.

Gelatins of various gel strengths are suitable for use in different applications. The firmness or strength of the set gel is typically measured by calculating the Bloom value, which can be determined using international standards and methodology. Briefly, the Bloom strength is a measurement of the strength of a gel formed by a 6.67% solution of gelatin in a constant temperature bath over 18 hours. A standard Texture Analyzer is used to measure the weight in grams required to depress a standard AOAC (Association of Official Agricultural Chemists) plunger 4 millimeters into the gel. If the weight in grams required for depression of the plunger is 200 grams, the particular gelatin has a Bloom value of 200. (See, e.g., United States Pharmacopoeia and Official Methods of Analysis of AOAC International, $17^{th}$ edition, Volume II.)

Commercial gelatins can thus be graded and sold on Bloom strength. Different ranges of Bloom values are appropriate for different uses of gelatin; for example, gelatins for use in various industrial applications, e.g., concrete stabilization, sand casting, molds, glues, coatings, etc., will be selected from a wide range of varying Bloom strengths, depending on the performance characteristics desired. Gelatins with varying Bloom strengths are also desired in the manufacture of various pharmaceutical products. For example, soft gel capsules are typically manufactured using ossein or skin gelatin with a Bloom value of about 150 to 175 and/or porcine-derived gelatin with a Bloom value of about 190 to 210, or blends thereof, while hard gel capsules might use a gelatin with a Bloom value of about 220 to 260. In food applications, gelatin used, for example, as a thickener in marshmallows or other confectionary products might have a Bloom strength of around 250. Various applications, including certain emulsifying fluids in photographic applications, and various industrial coatings, involve the use of non-gelling gelatins.

The present invention provides for the production of recombinant gelatins with different Bloom strengths. In one aspect, the present invention provides, for example, for the manufacture of gelatins with Bloom strengths of around 50, 100, 150, 200, 250, and 300. In one embodiment, the present invention provides for the production of a recombinant gelatin having a Bloom strength of around 400. Such a gelatin can be used, for example, in the manufacture of gel capsules, and could allow for the manufacture of a lighter and thinner capsule, as less material would need to be used to provide a gel of sufficient strength. Recombinant gelatins with Bloom strengths of under 100, and from 0 to 100, inclusively, are also contemplated.

The present invention provides methods for designing recombinant gelatins with the physical properties desired for particular applications. In one embodiment, the present invention provides recombinant gelatins comprising uniform molecules of a specified molecular weight or range of molecular weights, and methods for producing these recombinant gelatins. Such homogeneous and uniform materials are advantageous in that they provide a reliable source of product with predictable performance, minimizing variability in product performance and in manufacturing parameters. Currently, gelatin from different lots must sometimes be blended in order to produce a mixture with the desired physical characteristics, such as the viscosity or gel strength, etc., provided by a particular molecular weight or molecular weight range.

In applications in which a specific molecular weight range of recombinant gelatin would be preferred to a recombinant gelatin with a specific molecular weight, the present invention provides such materials. Using the recombinant gelatins of the present invention, a manufacturer could, for example, mix recombinant gelatins from lots with specified molecular weights, in certain percentages, in order to achieve a mixture with the desired molecular weight range. Additionally, the present recombinant gelatins are inherently more uniform and of greater consistency than currently available commercial products. In one method of the present invention, recombinant collagen is processed, such as by acid or heat hydrolysis, to produce recombinant gelatin of a molecular weight range narrower than that of currently available gelatin products. Using suitable and controllable hydrolysis conditions, the present methods produced recombinant human gelatins with molecular weight distributions similar to those of commercially available gelatins, as well as recombinant gelatins with ranges narrower than those of the molecular weight ranges of currently available products. (See Examples 9 and 10.)

The present invention provides recombinant gelatins of uniform molecular weight or specified ranges of molecular weights, removing variability and unpredictability, and allowing for fine-tuning of processes and predictable behavior. The present methods allow for the production of recombinant gelatins of any desired molecular weight or range of molecular weights. For example, in one embodiment, the recombinant gelatin has a molecular weight greater than 300 kDa. In another embodiment, the recombinant gelatin has a molecular weight range of from about 150 to 250 kDa, or of from about 250 to 350 kDa. Other molecular weight ranges are specifically contemplated, including, but not limited to, the following molecular weight ranges: about 0 to 50 kDa, about 50 to 100 kDa, about 100 to 150 kDa, about 150 to 200 kDa, about 200 to 250 kDa, about 250 to 300 kDa, and about 300 to 350 kDa.

In another aspect, recombinant gelatin with a molecular weight similar to that of some commercially available gelatins, of from about 10 to 70 kDa, could be produced. In preferred embodiments, the present invention provides recombinant gelatins narrower molecular weight ranges, not currently available in commercial products, such as from about 10 to 30 kDa, about 30 to 50 kDa, and about 50 to 70 kDa. In a particular embodiment, a recombinant gelatin with a chain length conferring specific properties appropriate to the intended application is provided. In various embodiments of the present invention, recombinant gelatins with uniform molecular weights of approximately 1 kDa, 5 kDa, 8 kDa, 9 kDa, 14 kDa, 16 kDa, 22 kDa, 23 kDa, 44 kDa, and 65 kDa are contemplated. (See, e.g., Table 2.)

In particular, in one method of the present invention, gelatin is produced from shortened collagen sequences, for example, the sequences identified in Table 2. These sequences represent specific collagenous domains and encode short forms of gelatin.

The present gelatins are capable of retaining valuable physical characteristics of gelatin, for example, film-forming abilities, while possessing average molecular weights lower or higher than those of conventionally derived animal gelatin. Various modifications of collagen sequences, including, for example, denaturing of the collagen, collagen chain, subunit, or fragments thereof, or varying degrees of hydroxylation, can be made that will produce gelatin with specific physical properties, i.e., a higher or lower melting point than conventional gelatin, different amino acid compositions, specific molecular weights or ranges of molecular weights, etc., and such variations are specifically contemplated herein.

The molecular weight of a typical fibril-forming collagen molecule, such as type I collagen, is 300 kDa. In some applications, such as those in which high molecular weight gelatins are used, it might be desirable to produce a gelatin with a greater molecular weight than that of currently available extracted gelatin. Therefore, in one embodiment of the present invention, gelatin can be produced containing molecules larger than the collagen from which commercial gelatin is currently extracted. The resultant higher molecular weight gelatin product can be used directly in various applications in which its physical properties would be desirable, or can be divided and subsequently treated to produce molecules of a smaller sizes.

In one embodiment, gelatin can be produced using collagens larger than those available in conventional animal sources. For example, the present methods of production could be adapted to produce the acid-soluble cuticle collagens derived from the body walls of vestimentiferan tube worm *Riftia pachyptila* (molecular weight~2600 kDa) and annelid *Alvinella pompejana* (molecular weight~1700 kDa). These collagens could be adapted to the present methods of production to produce larger molecules than those from which currently available gelatin is extracted, and the resultant product could be treated to produce gelatins as desired.

It is specifically contemplated that gelatins of various molecular weights can be produce by a variety of methods according to the present invention. For example, characteristics of the present recombinant gelatins, e.g., percentage hydroxylation, degrees of cross-linking, etc., can be varied to produce recombinant gelatins with the desired molecular weights. In one aspect, for example, the present invention provides a method for producing large molecular weight recombinant gelatins by using cross-linking agents known in the art to cross-link gelatin polypeptides. (See discussion, infra.)

In another aspect of the present invention, polypeptides from which gelatins could be derived are expressed from engineered constructs containing multiple copies of all or fragments of native collagen sequence. For example, in one embodiment, the present invention provides an altered collagen construct comprising multiple copies of the collagenous domain of type I collagen. In another embodiment, the construct comprises multiple copies of the collagenous domain of type III collagen. In a further embodiment, the construct comprises copies of type I and type III collagenous domains. The present invention provides for the use of single or multiple copies of all or portions of sequences encoding any collagen, including collagens type I through XX, inclusive. It is specifically contemplated that the present methods allow for the production of gelatins derived from more than one type of collagen. In one embodiment, recombinant gelatins derived from more than one type of collagen are co-expressed in an expression system, e.g., a host cell, transgenic animal, etc., such that a mixture of gelatins is produced.

In another embodiment, the present invention provides a method for producing gelatin without derivation from a collagen or procollagen triple helical stage. In one aspect, this involves production of recombinant gelatin by expression of various constructs in a high-temperature expression system, such as one relying on thermophilic organisms, that does not allow the formation of triple helical structures, but permits the activity of prolyl hydroxylase. The present gelatin could also be derived from collagen constructs containing mutations, additions, or deletions that prevent triple helical formation. In another aspect, this involves production of gelatin from shortened constructs that do not allow for formation of triple helices at regular temperatures, i.e., 37° C. Alternatively, gelatin can be produced in the presence of inhibitors of triple helix formation, for example, polyanions, that are co-expressed with the biosynthetic collagen constructs. Additionally, the biosynthetic gelatin of the present invention could be derived from recombinantly produced collagen chains that do not form triple helices.

In another embodiment, the invention provides a method of deriving gelatin from non-hydroxylated collagen or collagen in which there is partial rather than full hydroxylation of proline residues. In one aspect, this method comprises deriving gelatin from collagen expressed in the absence of prolyl hydroxylase, for example, in an insect expression system without prolyl hydroxylase. (See, e.g., Myllyharju et al. (1997) J. Biol. Chem. 272, 21824-21830.) In one method according to the present invention, gelatin is derived from the partially hydroxylated or non-hydroxylated collagen. Hydroxylation can be conferred, for example, by in vitro administration of hydroxylases. In one method, a low degree of substitution of hydroxyproline for proline can be forced by providing hydroxyproline to, e.g., bacterial or yeast host cells.

The present invention comprises fully-hydroxylated, partially-hydroxylated, and non-hydroxylated recombinant gelatins. In another embodiment, the method of the present invention comprises producing a gelatin or gelatin precursor having a specific degree of hydroxylation. In a further aspect, the invention relates to a method of producing gelatin having from 20 to 80 percent hydroxylation, preferably, from about 30 to 60 percent hydroxylation, and, most preferably, about 40 percent hydroxylation. (See Examples 4 and 5.) The partially-hydroxylated recombinant gelatins of the present invention can be obtained through mixing specified percentages of recombinant gelatins with different degrees of hydroxylation, or can be obtained directly. (See Examples 4 and 5.) Further, the invention provides methods for achieving partial hydroxylation of recombinant gelatins by administering prolyl hydroxylase to non-hydroxylated recombinant gelatins in vitro, and controlling the length of the reaction.

There are limits to the extent to which the thermal characteristics of currently available animal-source gelatins can be altered. The present invention specifically provides for methods of producing recombinant gelatin, wherein the recombinant gelatin has the specific thermal characteristics desired for a particular application. Using the methods of the present invention, for example, the melting point and/or gel strength of the recombinant gelatin can be manipulated in a variety of ways. The temperature stability and/or gel strength of recombinant gelatin can be measured by a variety of techniques well-known in the art.

Generally, the melting point of gelatin increases as the degree of hydroxylation increases. Using the methods of the present invention, it is possible to produce high molecular weight gelatins that, due to manipulation of hydroxylation and/or cross-linking, etc., have a lower gel strength and/or lower melting point than those of currently available animal-source gelatins. Therefore, the present invention provides a recombinant gelatin with properties unattainable in various commercial products, suitable for use in applications where a higher molecular weight gelatin is desired, in order to provide increased film strength, etc., but a non-gelling or low strength gel product is desired. In one embodiment, the present invention provides recombinant gelatin that has lower temperature stability due to incomplete hydroxylation of proline residues.

Such a recombinant gelatin could be useful in a variety of applications. In gelatin produced by current extraction methods, only fish gelatin provides a high average molecular weight film-forming protein that is non-gelling. The non-gelling and cold water-solubility characteristics offered by non-gelling fish gelatin can be matched by currently available hydrolyzed bovine and porcine gelatins, but with corresponding loss of film strength and flexibility, as the hydrolyzed gelatins are of lower average molecular weight. Therefore, in one embodiment, the present invention provides a partially-hydroxylated recombinant gelatin with lower gel strength and higher molecular weight than that provided by currently available animal-source materials.

A higher molecular weight, lower gel strength recombinant gelatin could also be useful in various pharmaceutical applications, in which stability is desired, but non- or low-gelling properties are desired in order to maintain the malleability and integrity of the pharmaceutical product. Such a recombinant gelatin could be used, for example, as a plasma expander, as its molecular weight could provide stability, increasing the residence time in circulation, and the altered setting point would prevent the material from gelling at room temperature, allowing the expander to be administered without warming. In one embodiment, the present invention provides a partially-hydroxylated recombinant gelatin suitable for use in pharmaceutical applications, for example, as a plasma expander.

In another aspect, partially-hydroxylated recombinant gelatin is obtained through expression of recombinant gelatin, or expression of polypeptides from which the present recombinant gelatin can be derived, in the absence of prolyl hydroxylase, for example, in an insect expression system without prolyl hydroxylase. (See, e.g., Myllyharju et al. (1997) J. Biol. Chem. 272, 21824-21830.) Hydroxylation can occur at the time of production or can be subsequently imposed through, e.g., in vitro biological or chemical modification. In one method of the present invention, recombinant gelatins are derived from partially-hydroxylated or from fully hydroxylated collagen.

Gelatins derived from natural sources by currently available methods are greatly strengthened by the existence of covalent cross-links between lysine residues of the constituent collagen molecules. Cross-linking occurs naturally in the extracellular space following collagen secretion and fibril formation, as prior to secretion, certain lysine residues are hydroxylated by the enzyme lysyl hydroxylase. The extracellular enzyme lysyl oxidase subsequently deamidates certain lysine and hydroxylysine residues in the collagen molecules, yielding highly reactive aldehyde groups that react spontaneously to form covalent bonds. The resulting cross-linked collagens yield gelatins of increased gel strength and increased viscosity. Specifically, a higher degree of cross-linking results in gelatins with higher melting temperatures and greater gel strength.

In one aspect, the present invention provides recombinant gelatins that are cross-linked, resulting in higher molecular weight gelatins. (See Example 7.) Cross-linking can be imposed by different methods, such as by biological or chemical modification. For example, in one embodiment, recombinant gelatin or a polypeptide from which gelatin can be derived is expressed in the presence of lysyl hydroxylase and lysyl oxidase. In another embodiment, the polypeptide is modified by cross-linking after expression. In a further aspect, the present invention provides for imposition of cross-linking by chemical means, such as by reactive chemical cross-linkers, for example 1-ethyl-3-(dimethylaminopropyl) carbodiimide hydrochloride (EDC). (See Example 7.) Other chemical cross-linking agents, such as bis(sulfosuccinimidyl) suberate ($BS^3$), 3,3'-dithiobis(sulfosuccinimidyl) propionate (DTSSP), and Tris-sulfosuccinimidyl aminotriacetate (Sulfo-TSAT) may also be used, as can various agents known in the art. Additionally, the present invention provides methods of producing recombinant gelatins with varying degrees of cross-linking, useful for obtaining recombinant gelatins of desired melting points, gel strength, and viscosity.

The present invention provides methods to manipulate the molecular weight, the level of hydroxylation, and the degree of cross-linking of the recombinant gelatins to allow for creation of recombinant gelatins of different and specific Bloom strengths, as well as recombinant gelatins of different and specific levels of viscosity.

Proline hydroxylation plays central role in natural collagen formation. Hydroxylation of specific lysyl residues in the sequence X-Lys-Gly also performs an important function in collagen synthesis and fibril formation. The hydroxyl groups on modified lysine residues function as both attachment sites for carbohydrates and as essential sites for the formation of stable intermolecular cross-links. These modifications require the expression of specific enzymes, lysyl hydroxylase and lysyl oxidase.

Therefore, in one aspect of the invention, the co-expression of these enzymes with the polypeptides of the present invention is contemplated. The gene encoding lysyl hydroxylase (Hautala et al. (1992) Genomics 13:62-69) is expressed in a host cell, which is then further modified by the introduction of a sequence encoding a gelatin or polypeptide from which gelatin can be derived, as described in the present invention. The recombinant gelatins of the present invention can therefore be post-translationally modified by the activity of endogenously expressed lysyl hydroxylase and lysyl oxidase. The recombinant gelatins of the present invention can also be modified by the expression of exogenous lysyl hydroxylase and lysyl oxidase. In one embodiment, recombinant gelatins produced are non-hydroxylated, and subsequently altered by imposing the desired degree of hydroxylation of lysine residues by the enzymatic activity of lysyl hydroxylase. The ability to alter the degree of lysyl hydroxylation is desirable in producing gelatins, and polypeptides from which gelatin can be derived, with various degrees of cross-linking that lead to the desired gel strengths and viscosities.

In further embodiments, a polypeptide containing hydroxylysine residues can also be expressed in, for example, a yeast cell, in which hydroxyproline is produced by the activity of prolyl hydroxylase. (See Examples 1 and 4.) In some embodiments, the modified recombinant gelatin or polypeptide from which gelatin can be derived can be formulated and administered to an animal or human, thus serving as a substrate for the activities of endogenous enzymes, such as lysyl oxidase, thus allowing the collagenous polypeptide to be incorporated into tissues in a stabilized cross-linked form. Therefore, one aspect of the present invention provides for the production of recombinant gelatins of desirable gel strengths and viscosity for commercial use, without the need for lysyl hydroxylase or lysyl oxidase activities.

The invention also provides for the production of gelatin having a particular gelling point. In one embodiment, the present methods provide for the production of gelatin having a setting or gelling point of from 15 to 35° C. In further embodiments, the recombinant gelatin has a setting point of from 15 to 25° C., from 25 to 35° C., and from 20 to 30° C.

In various aspects, the present invention provides recombinant gelatin that is non-hydrolyzed, fully hydrolyzed, or hydrolyzed to varying degrees, such as gelatins that are a mixture of hydrolyzed and non-hydrolyzed products. Additionally, the present invention provides methods of producing recombinant gelatins with varying degrees of hydrolysis. (See Examples 9 and 10.) Gelatin hydrosylates are typically cold water-soluble and are used in a variety of applications, particularly in the pharmaceutical and food industries, in which a gelatin with non-gelling properties is desirable. Gelatin hydrolysates are used in the pharmaceutical industry in film-forming agents, microencapsulation processes, arthritis and joint relief formulas, tabletting, and various nutritional formulas. In the cosmetics industry, gelatin hydrolysates are used in shampoos and conditioners, lotions and other formulations, including lipsticks, and in fingernail formulas, etc. Gelatin hydrolysates appear as nutritional supplements in protein and energy drinks and foods; are used as fining agents in wine, beer, and juice clarification; and are used in the microencapsulation of additives such as food flavorings and colors. Gelatin hydrosylates are used in industrial applications for their film-forming characteristics, such as in coatings of elements in semiconductor manufacture, etc.

In one embodiment of the present invention, gelatin is produced from collagen sequences in which particular native domains have been deleted or have been added in order to alter the behavior of the expressed product. The invention further contemplates methods of producing recombinant gelatin wherein the gelatin is produced directly from an altered collagen construct, without production of an intact triple helical collagen. In particular, the present invention contemplates methods of producing recombinant gelatin comprising the expression of various engineered constructs that do not encode standard triple helical collagen. For example, specific deletions can eliminate collagenase-responsive regions, and various regions eliciting immunogenic, e.g., antigenic and allergenic, responses.

Specific domains of various collagens have been associated with specific activities. (See, e.g., Shahan et al. (1999) Con. Tiss. Res. 40:221-232; Raff et al. (2000) Human Genet 106:19-28, both of which references are incorporated by reference herein in their entireties.) In particular, the present invention specifically provides for methods of producing recombinant gelatins derived from collagen constructs altered to eliminate or to reduce or increase specific regions of a collagen gene associated with a specific activity. Specifically, such regions could be deleted in full or in part to produce a gelatin lacking or with reduced specific activity, or additional copies of the specific region could be added to produce a gelatin with enhanced activity. For example, sequences in types I and III collagen recognized by the α2β1 integrin receptor on the platelet cell surface have been identified. (Knight et al. (1998) J. Biol. Chem. 273:33287-33294; and Morton et al. (1997) J. Biol. Chem. 272:11044-11048, which references are incorporated by reference herein in their entirety.)

In one aspect of the present invention, it is desirable to create a homogeneous gelatin composed of fragments synthesized from collagen constructs lacking platelet activation regions. Such gelatin could be included, for example, in products associated with anastomosis and vascular grafting, etc., including coatings for stent and graft devices. Such products can be associated with deleterious side effects, for example, thrombosis, that can develop in association with the use of such products as a result of the platelet-aggregating regions present in the collagenous product. In one aspect, the present invention provides for a method of producing a recombinant gelatin which can provide support for cell attachment when used in a stent or similar device, but which does not include platelet-reactive regions, thus minimizing the risk of platelet aggregation. (See Example 2.) Therefore, the present invention provides in one embodiment for a stent coating comprising recombinant gelatin. In a preferred embodiment, the recombinant gelatin is recombinant human gelatin. In some instances, such as various wound care applications, it could be desirable to provide recombinant gelatin comprising domains capable of inducing specific aggregating activities.

A gelatin of the present invention could be expressed from collagen constructs that did not encode the regions recognized by the α2β1 receptor, or from constructs with one or with multiple copies of such regions, thus providing a homogeneous and consistent gelatin product without or with reduced platelet aggregation and activation. In one aspect, the present invention provides for the production of recombinant gelatin, either through direct expression of gelatin or through processing of gelatin from collagenous polypeptides, through the use of highly efficient recombinant expression. The present production methods, as opposed to current methods of extraction, offer extreme flexibility, as any one of a number of expression systems can be used. The production material is accessible, for example, in yeast or plant biomass. Secretion in certain production systems can be optimized, for example, by dictating the uniform size of particular gelatin molecules to be produced according to the present methods. In various embodiments, the present gelatins or the polypeptides from which these gelatins are derived, are produced in expression systems including, but not limited to, prokaryotic expression systems, such as bacterial expression systems, and eukaryotic expression systems, including yeast, animal, plant, and insect expression systems. Expression systems such as transgenic animals and transgenic plants are contemplated.

The present invention provides for expression of at least one polynucleotide encoding a gelatin or a polypeptide, from which gelatin can be derived in a cell. In one embodiment, the present invention provides for the expression of more than one polynucleotide encoding a gelatin or a polypeptide from which gelatin can be derived in a cell, such that recombinant gelatin that has containing homogeneous or heterogeneous polypeptides is produced. The present invention further provides for expression of a polynucleotide encoding a collagen processing or post-translational enzyme or subunit thereof in a cell. Different post-translational modifications, and different post-translational enzymes, e.g., prolyl hydroxylase, lysyl hydroxylase, etc., can effect, for example, Bloom strength and other physical characteristics of the present gelatins.

The recombinant gelatins of the present invention are derived from collagenous sequences. The sequences from which the encoding polynucleotides of the invention are derived can be selected from human or from non-human sequences, depending on the characteristics desired for the intended use of the ultimate gelatin product. For pharmaceutical and medical uses, recombinant human gelatin is preferred. Non-human sources include non-human mammalian sources, such as bovine, porcine, and equine sources, and other animal sources, such as chicken and piscine sources. Non-native sequences are specifically contemplated.

Nucleic acid sequences encoding collagens have been generally described in the art. (See, e.g., Fuller and Boedtker (1981) Biochemistry 20:996-1006; Sandell et al. (1984) J Biol Chem 259:7826-34; Kohno et al. (1984) J Biol Chem 259:13668-13673; French et al. (1985) Gene 39:311-312; Metsaranta et al. (1991) J Biol Chem 266:16862-16869; Metsaranta et al. (1991) Biochim Biophys Acta 1089:241-243; Wood et al. (1987) Gene 61:225-230; Glumoff et al. (1994) Biochim Biophys Acta 1217:41-48; Shirai et al. (1998) Matrix Biology 17:85-88; Tromp et al. (1988) Biochem J 253:919-912; Kuivaniemi et al. (1988) Biochem J 252:633-640; and Ala-Kokko et al. (1989) Biochem J 260:509-516.) See also co-pending, commonly-owned application U.S. patent application Ser. No. 09/709,700, entitled "Animal Collagens and Gelatins," filed 10 Nov. 2000, incorporated herein by reference in its entirety.)

The nucleic acid sequences of the invention may be engineered in order to alter the coding sequences used to produce recombinant gelatin, or polypeptides from which the recombinant gelatin can be derived, for a variety of ends including, but not limited to, alterations which modify processing and expression of the gene product. For example, alternative secretory signals may be substituted for any native secretory signals. Mutations may be introduced using techniques well known in the art, e.g., site-directed mutagenesis, PCR-directed mutagenesis, cassette mutagenesis, and other techniques well-known in the art to insert new restriction sites, or to alter glycosylation patterns, phosphorylation, proteolytic turnover/breakdown, etc. Additionally, when producing gelatin in an expression system using particular host cells, the polynucleotides of the invention may be modified in the silent position of any triplet amino acid codon so as to better conform to the codon preference of a particular host organism.

Altered polynucleotide sequences which may be used in accordance with the invention include sequences containing deletions, additions, or substitutions of nucleotide residues in native collagen sequences. Such polynucleotides can encode the same or a functionally equivalent gene product. The gene product itself may contain deletions, additions or substitutions of amino acid residues within a collagen sequence.

The polynucleotide sequences of the invention are further directed to sequences which encode variants of the encoded polypeptides. The encoded amino acid variants may be prepared by various methods known in the art for introducing appropriate nucleotide changes for encoding variant polypeptides. Two important variables in the construction of amino acid sequence variants are the location of the mutation and the nature of the mutation. The amino acid sequence variants of the gelatins of the present invention, or of the polypeptides from which the present gelatins are derived, are preferably constructed by mutating the polynucleotide to give an amino acid sequence that does not occur in nature. These amino acid alterations can be made at sites that differ in, for example, collagens from different species (variable positions), or in highly conserved regions (constant regions). Sites at such locations will typically be modified in series, e.g., by substituting first with conservative choices (e.g., hydrophobic amino acid to a different hydrophobic amino acid) and then with more distant choices (e.g., hydrophobic amino acid to a charged amino acid), and then deletions or insertions may be made at the target site.

Due to the inherent degeneracy of the genetic code, other nucleic acid sequences which encode substantially the same or a functionally equivalent amino acid sequence or polypeptide, natural, synthetic, semi-synthetic, or recombinant in origin, may be used in the practice of the claimed invention. Degenerate variants are specifically contemplated by the present invention, including codon-optimized sequences. In addition, the present invention specifically provides for polynucleotides which are capable of hybridizing to a particular sequence under stringent conditions.

Expression

The present methods are suitably applied to the range of expression systems available to those of skill in the art. While a number of these expression systems are described below, it is to be understood that application of the present methods not limited to the specific embodiments set forth below.

A variety of expression systems may be utilized to contain and express sequences encoding the recombinant gelatins of the present inventions or encoding polypeptides from which these gelatins can be derived. These include, but are not limited to, microorganisms such as bacteria transformed with recombinant bacteriophage, plasmid, or cosmid nucleic acid expression vectors; yeast transformed with yeast expression vectors; insect cell systems infected with virus expression vectors (e.g., baculovirus); filamentous fungi transformed with fungal vectors; plant cell systems transformed with virus expression vectors (e.g., cauliflower mosaic virus, CaMV; tobacco mosaic virus, TMV) or with bacterial expression vectors (e.g., pET or pBR322 plasmids); or animal cell systems.

Control elements or regulatory sequences suitable for use in expressing the polynucleotides of the present invention are those non-translated regions of the vector, including enhancers, promoters, and 5' and 3' untranslated regions, which interact with host cellular proteins to carry out transcription and translation. Such elements may vary in strength and specificity. Depending on the vector system and host utilized, any number of suitable transcription and translation elements may be used.

Promoters are untranslated sequences located upstream from the start codon of the structural gene that control the transcription of the nucleic acid under its control. Inducible promoters are promoters that alter their level of transcription initiation in response to a change in culture conditions, e.g., the presence or absence of a nutrient. One of skill in the art would know of a large number of promoters that would be recognized in host cells suitable for use in the methods of the present invention.

Promoter, enhancer, and other control elements can be selected as suitable by one skilled in the art. For example, when cloning in bacterial systems, inducible promoters such as the hybrid lacZ promoter of the BLUESCRIPT phagemid (Stratagene, La Jolla, Calif.) or pSPORT1 plasmid (GIBCO BRL) and the like may be used. In insect cells, the baculovirus polyhedrin promoter may be used. In plant systems, promoters or enhancers derived from the genomes of plant cells (e.g., heat shock promoter, the promoter for the small subunit of RUBISCO; the promoter for the chlorophyll a/b binding protein; promoters for various storage protein genes, etc.) or from plant viruses (e.g., viral promoters or leader sequences, the 35S RNA promoter of CaMV, the coat protein promoter of TMV, etc.) may be cloned into the vector. In mammalian cell systems, promoters from mammalian genes (e.g., metallothionein promoter, α-actin promoter, etc.) or from mammalian viruses (e.g., the adenovirus late promoter, CMV, SV40, LTR, TK, and the vaccinia virus 7.5 K promoters, etc.) are preferable. If it is necessary to generate a cell line that contains multiple copies of the sequence encoding the desired polypeptide, vectors based on SV40 or EBV may be used with an appropriate selectable marker.

Such promoters can be are operably linked to the polynucleotides encoding the gelatin or gelatin precursors of the present invention, such as by removing the promoter from its native gene and placing the encoding polynucleotide at the 3' end of the promoter sequence. Promoters useful in the present invention include, but are not limited to, prokaryotic promoters, including, for example, the lactose promoter, arabinose promoter, alkaline phosphatase promoter, tryptophan promoter, and hybrid promoters such as the tac promoter; yeast promoters, including, for example, the promoter for 3-phosphoglycerate kinase, other glycolytic enzyme promoters (hexokinase, pyruvate decarboxylase, phophofructosekinase, glucose-6-phosphate isomerase, etc.), the promoter for alcohol dehydrogenase, the alcohol oxidase (AOX) 1 or 2 promoters, the metallothionein promoter, the maltose promoter, and the galactose promoter; and eukaryotic promoters, including, for example, promoters from the viruses polyoma, fowlpox, adenovirus, bovine papilloma virus, avian sarcoma virus, cytomegalovirus, retroviruses, SV40, and promoters from the target eukaryote, for example, the glucoamylase promoter from *Aspergillus*, actin or ubiquitin promoters, an immunoglobin promoter from a mammal, and native collagen promoters. (See, e.g., de Boer et al. (1983) Proc. Natl. Acad. Sci. USA 80:21-25; Hitzeman et al. (1980) J. Biol. Chem. 255:2073); Fiers et al. (1978) Nature 273:113; Mulligan and Berg (1980) Science 209:1422-1427; Pavlakis et al. (1981) Proc. Natl. Acad. Sci. USA 78:7398-7402; Greenway et al. (1982) Gene 18:355-360; Gray et al. (1982) Nature 295:503-508; Reyes et al. (1982) Nature 297:598-601; Canaani and Berg (1982) Proc. Natl. Acad. Sci. USA 79:5166-5170; Gorman et al. (1982) Proc. Natl. Acad. Sci. USA 79:6777-6781; and Nunberg et al. (1984) Mol. and Cell. Biol. 11(4):2306-2315.)

The polynucleotide sequences encoding the gelatins and gelatin precursors of the present methods may be under the transcriptional control of a constitutive promoter, directing expression generally. Alternatively, the polynucleotides employed in the present methods are expressed in a specific tissue or cell type, or under more precise environmental conditions or developmental controls. Promoters directing expression in these instances are known as inducible promoters. In the case where a tissue-specific promoter is used, protein expression is particularly high in the tissue from which extraction of the protein is desired. In plants, for example, depending on the desired tissue, expression may be targeted to the endosperm, aleurone layer, embryo (or its parts as scutellum and cotyledons), pericarp, stem, leaves tubers, roots, etc. Examples of known tissue-specific promoters in plants include the tuber-directed class I patatin promoter, the promoters associated with potato tuber ADPGPP genes, the soybean promoter of β-conglycinin (7S protein), which drives seed-directed transcription, and seed-directed promoters from the zein genes of maize endosperm. (See, e.g., Bevan et al. (1986) Nucleic Acids Res. 14: 4625-4638; Muller et al. (1990) Mol. Gen. Genet. 224: 136-146; Bray (1987) Planta 172:364-370; and Pedersen et al. (1982) Cell 29:1015-1026.)

Transcription of the sequences encoding the gelatins or gelatin precursors of the present invention from the promoter is often increased by inserting an enhancer sequence in the vector. Enhancers are cis-acting elements, usually about from 10 to 300 bp, that act to increase the rate of transcription initiation at a promoter. Many enhancers are known for both eukaryotes and prokaryotes, and one of ordinary skill could select an appropriate enhancer for the host cell of interest. (See, e.g., Yaniv (1982) Nature 297:17-18.)

The gelatins and gelatin precursors of the present invention may be expressed as secreted proteins. When the engineered cells used for expression of the proteins are non-human host cells, it is often advantageous to replace the secretory signal peptide of the collagen protein with an alternative secretory signal peptide which is more efficiently recognized by the host cell's secretory targeting machinery. The appropriate secretory signal sequence is particularly important in obtaining optimal fungal expression of mammalian genes. (See, e.g., Brake et al. (1984) Proc. Natl. Acad. Sci. USA 81:4642.) Other signal sequences for prokaryotic, yeast, fungi, insect or mammalian cells are well known in the art, and one of ordinary skill could easily select a signal sequence appropriate for the host cell of choice.

The efficiency of expression may be enhanced by the inclusion of enhancers appropriate for the particular cell system which is used, such as those described in the literature. (See, e.g., Scharf, D. et al. (1994) Results Probl. Cell Differ. 20:125-162.) In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, prenylation, and acylation. Post-translational processing which cleaves a "prepro" form of the protein may also be used to facilitate correct insertion, folding, and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

In accordance with the invention, polynucleotide sequences encoding recombinant gelatins or polypeptides from which gelatins can be derived may be expressed in appropriate host cells. In preferred embodiments of the invention, the recombinant gelatin is human gelatin. In other preferred embodiments of the invention, the polynucleotide sequences are derived from type I collagen sequence, free of coding sequence for any other type of collagen, or from type II collagen, free of coding sequence for any other type of collagen, or from type III collagen, free of coding sequence for any other type of collagen. In another embodiment, the encoding polynucleotides are derived from type I and type III collagen in specified quantities, such that the gelatin produced by or derived from the encoded polypeptides comprises a mixture of type I and type III collagens in defined quantities.

In order to express the collagens from which the present gelatins are derived, or to express sequences other than natural collagen sequences leading to the production of the present gelatin, nucleotide sequences encoding the collagen, or a functional equivalent, or other sequence, for example, a shortened collagen sequence, such as those presented in Table 2, is inserted into an appropriate expression vector, i.e., a vector which contains the necessary elements for the transcription and translation of the inserted coding sequence, or in the case of an RNA viral vector, the necessary elements for replication and translation.

Methods well-known to those skilled in the art can be used to construct expression vectors containing the desired coding sequence and appropriate transcriptional/translational control signals. These methods include standard DNA cloning techniques, e.g., in vitro recombinant techniques, synthetic techniques, and in vivo recombination. See, for example, the techniques described in Maniatis et al., supra; Ausubel et al., supra; and Ausubel, F. M. (1997) *Short Protocols in Molecular Biology*, John Wiley and Sons, New York, N.Y.

Various expression vectors may be used to express the present polypeptides. For example, a typical expression vector contains elements coding for a replication origin; a cloning site for insertion of an exogenous nucleotide sequence; elements that control initiation of transcription of the exogenous gene, such as a promoter; and elements that control the processing of transcripts, such as a transcription/termination/polyadenylation sequence. An expression vector for use in the present invention can also contain such sequences as are needed for the eventual integration of the vector into the chromosome. In addition, a gene that codes for a selection marker which is functionally linked to promoters that control transcription initiation may also be within the expression vector, for example, an antibiotic resistance gene to provide for the growth and selection of the expression vector in the host.

The vectors of this invention may autonomously replicate in the host cell, or may integrate into the host chromosome. Suitable vectors with autonomously replicating sequences are well known for a variety of bacteria, yeast, and various viral replications sequences for both prokaryotes and eukaryotes. Vectors may integrate into the host cell genome when they have a DNA sequence that is homologous to a sequence found in host cell genomic DNA.

For long-term, high-yield production of recombinant proteins, stable expression is preferred. For example, cell lines which stably express the present polypeptides may be transformed using expression vectors containing viral origins of replication or appropriate expression elements (e.g., promoters, enhancers, transcription terminators, polyadenylation sites, etc.) and a selectable marker gene on the same or on a separate vector. Following the introduction of the vectors, cells may be allowed to grow for 1-2 days in enriched media, and are then switched to selective media. The selectable marker in the recombinant plasmid confers resistance to selection, allowing growth and recovery of cells that successfully express the introduced sequences. Resistant clones of stably transformed cells may be proliferated using tissue culture techniques appropriate to the cell type. This method may advantageously be used to produce cell lines which express a desired polypeptide.

Expression of the various sequences used in the methods of the present invention driven by, for example, the galactose promoters can be induced by growing the culture on a non-repressing, non-inducing sugar so that very rapid induction follows addition of galactose; by growing the culture in glucose medium and then removing the glucose by centrifugation and washing the cells before resuspension in galactose medium; and by growing the cells in medium containing both glucose and galactose so that the glucose is preferentially metabolized before galactose-induction can occur.

Any number of selection systems may be used to recover transformed cell lines. These include, but are not limited to, the herpes simplex virus thymidine kinase and adenine phosphoribosyl-transferase genes which can be employed in tk⁻ or aprt⁻ cells, respectively. (See, e.g., Wigler, M. et al. (1977) Cell 11:223-32; Lowy, I. et al. (1980) Cell 22:817-23.) Also, antimetabolite, antibiotic, or herbicide resistance can be used as the basis for selection. Therefore, the present invention contemplates the use of such selectable markers, for example: dhfr, which confers resistance to methotrexate; npt, which confers resistance to the aminoglycosides neomycin and G-418; and als or pat, which confer resistance to chlorsulfuron and to phosphinotricin acetyltransferase, respectively. (See, e.g., Wigler, M. et al. (1980) Proc. Natl. Acad. Sci. 77:3567-3570; and Colbere-Garapin, F. et al. (1981) J. Mol. Biol. 150:1-14.)

Additional selectable genes have been described, for example, trpB, which allows cells to utilize indole in place of tryptophan, or hisD, which allows cells to utilize histinol in place of histidine. (See, e.g., Hartman, S. C. and R. C. Mulligan (1988) Proc. Natl. Acad. Sci. 85:8047-51.) Recently, the use of visible markers has gained popularity with such markers as anthocyanins, β-glucuronidase and its substrate GUS, and luciferase and its substrate luciferin, now widely used not only to identify transformants, but also to quantify the amount of transient or stable protein expression attributable to a specific vector system. (See, e.g., Rhodes, C. A. et al. (1995) Methods Mol. Biol. 55:121-131.)

As noted above, the expression vectors for use in the present methods of production can typically comprise a marker gene that confers a selectable phenotype on cells. Usually, the selectable marker gene will encode antibiotic resistance, with suitable genes including at least one set of genes coding for resistance to the antibiotic spectinomycin, the streptomycin phophotransferase (SPT) gene coding for streptomycin resistance, the neomycin phophotransferase (NPTH) gene encoding kanamycin or geneticin resistance, the hygromycin resistance gene, genes coding for resistance to herbicides which act to inhibit the action of acetolactate synthase (ALS), in particular, the sulfonylurea-type herbicides (e.g., the S4 and/or Hra mutations), genes coding for resistance to herbicides which act to inhibit action of glutamine synthase, such as phophinothricin or basta (e.g. the bar gene), or other similar genes known in the art. The bar gene encodes resistance to the herbicide basta, the nptII gene encodes resistance to the antibiotics kanamycin and geneticin, and the ALS gene encodes resistance to the herbicide chlorsulfuron.

Other methods for determining which host cells, subsequent to transformation, contain the polynucleotides of interest include a variety of procedures known to those of skill in the art. These procedures include, but are not limited to, nucleic acid hybridizations, including DNA-DNA or DNA-RNA hybridizations, and various protein bioassay or immunoassay techniques including membrane-, solution-, or chip-based technologies for the detection and/or quantification of polynucleotides or polypeptides.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells that possess the cellular machinery for proper processing of the primary transcript, including various modifications such as protein folding, disulfide bond formation, glycosylation, and phosphorylation of the gene product may be used. Such mammalian host cells include, but are not limited to, CHO, VERO, BHK, HeLa, COS, MDCK, 293, WI38, etc.

Specific initiation signals may also be used to achieve more efficient translation of the polynucleotides of the present invention. Such signals include the ATG initiation codon and adjacent sequences. In cases where sequences encoding the present polypeptides, along with any initiation or upstream sequences required for translation, etc., are inserted into the appropriate expression vector, no additional transcriptional or translational control signals may be needed. However, in cases where only coding sequences, or portions thereof, are inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. (See, e.g., Bittner et al. (1987) Meth. in Enzymol. 153:516-544.)

A host cell of the present invention can be infected, transfected, or transformed with at least one polynucleotide encoding a post-translational enzyme, in addition to at least one polynucleotide encoding a gelatin of the present invention or a polypeptide from which the gelatin can be derived. Such polynucleotides include those encoding collagen post-translational enzymes, such as prolyl 4-hydroxylase, collagen glycosyl transferase, C-proteinase, N-proteinase, lysyl oxidase, or lysyl hydroxylase, and can be inserted into cells that do not naturally produce post-translational enzymes, for example, into yeast cells, or cells that may not naturally produce sufficient amounts of post-translational enzymes, for example, various insect and mammalian cells, such that exogenous enzyme may be required to produce certain post-translational effects. In one embodiment of the present invention, the post-translational enzyme is prolyl 4-hydroxylase, and the polynucleotide encodes the α or the β subunit of prolyl hydroxylase. In a preferred embodiment, polynucleotides encoding the α subunit and the β subunit of prolyl 4-hydroxylase are inserted into a cell to produce a biologically active prolyl 4-hydroxylase enzyme, co-expressed with a polynucleotide encoding a gelatin or a polypeptide from which gelatin can be derived.

The polynucleotides encoding post-translational enzymes may be derived from any source, whether natural, synthetic, or recombinant. In a preferred embodiment, the post-translational enzyme is derived from the same species as is the recombinant gelatin to be produced. In one embodiment, the recombinant gelatin to be produced is human recombinant gelatin, and the post translational enzyme is human prolyl 4-hydroxylase.

The expressed gelatins or gelatin precursors of the present invention are preferably secreted into culture media and can be purified to homogeneity by methods known in the art, for example, by chromatography. In one embodiment, the recombinant gelatin or gelatin precursors are purified by size exclusion chromatography. However, other purification techniques known in the art can also be used, including, but not limited to, ion exchange chromatography, hydrophobic interaction chromatography (HIC), and reverse-phase chromatography. (See, e.g., Maniatis et al., supra; Ausubel et al., supra; and Scopes (1994) *Protein Purification: Principles and Practice*, Springer-Verlag New York, Inc., NY.)

Prokaryotic

In prokaryotic systems, such as bacterial systems, any one of a number of expression vectors may be selected, depending upon the use intended for the polypeptides to be expressed. For example, when large quantities of the recombinant gelatins of the present invention, or polypeptides from which these recombinant gelatins can be derived, are needed, vectors which direct high-level expression of fusion proteins that can be readily purified may be used. Such vectors include, but are not limited to, multifunctional *E. coli* cloning and expression vectors such as BLUESCRIPT (Stratagene), in which the encoding sequence may be ligated into the vector in frame with sequences for the amino-terminal Met and the subsequent seven residues of β-galactosidase so that a hybrid protein is produced; pIN vectors (Van Heeke, G. and S. M. Schuster (1989) J. Biol. Chem. 264:5503-5509); and the like. pGEX (Promega, Madison, Wis.) and pET (Invitrogen) vectors may also be used to express foreign polypeptides as fusion proteins with glutathione S-transferase (GST). In general, such fusion proteins are soluble and can easily be purified from lysed cells by a variety of methods known in the art, for example, by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety.

Yeast

In preferred embodiments, the present invention provides methods of producing recombinant gelatin using a yeast expression system. In preferred embodiments, gelatin is produced directly from altered collagen constructs or derived from processing of collagenous polypeptides. A number of vectors containing constitutive, non-consitutive, or inducible promoters may be used in yeast systems. (See, e.g., Ausubel et al., supra, Chapter 13.) In some aspects, vectors containing sequences which direct DNA integration into the chromosome are used for expression in *S. cerevisiea*.

In one embodiment, the recombinant gelatins of the invention, or the polypeptides from which these gelatins can be derived, are expressed using host cells from the yeast *Saccharomyces cerevisiae*. *Saccharomyces cerevisiae* can be used with any of a large number of expression vectors available in the art, including a number of vectors containing constitutive or inducible promoters such as a factor, AOX, GAL1-10, and PGH. (See, e.g., Ausubel et al., supra, and Grant et al. (1987) Methods Enzymol. 153:516-544.) Commonly employed expression vectors are shuttle vectors containing the 2μ origin of replication for propagation both in yeast and the ColE1 origin for *E. coli*, including a yeast promoter and terminator for efficient transcription of the foreign gene. Vectors incorporating 2μ plasmids include, but are not limited to, pWYG4 and pYES2, which have the 2μ ORI-STB elements, the GAL1-10, etc. In one method of the present invention, in which a hydroxylated product is desired, involves the co-expression of a collagen post-translational enzyme, for example, prolyl 4-hydroxylase. In one such method, using the pWYG4 vector, the NcoI cloning site is used to insert the gene for either the α or β subunit of prolyl 4-hydroxylase, and to provide the ATG start codon for either the α or β subunit. In one method, expression plasmids are used which direct integration into the chromosome of the host.

The expression vector pWYG7L, which has intact 2α ORI, STB, REP1 and REP2, the GAL7 promoter, and the FLP terminator, can also be used. When the co-expression of a post-translational enzyme, for example, prolyl 4-hydroxylase, is desired, the gene for either the α or β subunit of prolyl 4-hydroxylase is inserted in the polylinker with its 5' ends at a BamHI or NcoI site. The vector containing the prolyl 4-hydroxylase gene is transformed into *S. cerevisiae* either before or after removal of the cell wall to produce spheroplasts that take up DNA on treatment with calcium and polyethylene glycol or by treatment of intact cells with lithium ions. Alternatively, DNA can be introduced by electroporation. Transformants can be selected by using host yeast cells that are auxotrophic for leucine, tryptophane, uracil or histidine together with selectable marker genes such as LEU2, TRP1, URA3, HIS3 or LEU2-D.

In another preferred embodiment, the methods of producing recombinant gelatin according to the present invention use host cells from the yeast *Pichia pastoris*, or from other species of non-*Saccharomyces* yeast, that possess advantages in producing high yields of recombinant protein in scaled-up procedures. *Pichia* expression systems include advantages of both prokaryotic (e.g., *E. coli*) expression systems—high-level expression, easy scale-up, and inexpensive growth—and eukaryotic expression systems—protein processing, folding, and post-translational modifications. Such expression systems can be constructed using various methods and kits available to those skilled in the art, for example, the *PICHIA* EXPRESSION kits available from Invitrogen Corporation (San Diego, Calif.).

There are a number of methanol responsive genes in methylotrophic yeasts such as *Pichia pastoris*, or *Pichia methanolica*, etc., the expression of each being controlled by methanol responsive regulatory regions (also referred to as promoters). Any of such methanol responsive promoters are suitable for use in the practice of the present invention. Examples of specific regulatory regions include the promoter for the primary alcohol oxidase gene from *Pichia pastoris* AOX1, the promoter for the secondary alcohol oxidase gene from *Pichia pastoris* AOX2, the FLD1 promoter, the promoter for the dihydroxyacetone synthase gene from *Pichia pastoris* (DAS), the promoter for the P40 gene, etc. Typically, expression in *Pichia pastoris* is obtained by the promoter from the tightly regulated AOX1 gene. (See, e.g., Ellis et al. (1985) Mol. Cell. Biol. 5:1111; and U.S. Pat. No. 4,855,231.) Constitutive expression can also be achieved using, e.g., the GPH promoter.

Another yeast expression system preferred for use in the methods of the present invention makes use of the methylotrophic yeast *Hansenula polymorpha*. This system can be used, for example, in a method of production of the present invention where high yield is desirable. Growth on methanol results in the induction of enzymes key in, such as MOX (methanol oxidase), DAS (dihydroxyacetone synthase), and FMHD (formate dehydrogenase). These enzymes can constitute up to 30-40% of the total cell protein. The genes encoding MOX, DAS, and FMDH production are controlled by strong promoters induced by growth on methanol and repressed by growth on glucose. Any or all three of these promoters may be used to obtain high level expression of heterologous sequences in *H. polymorpha*, according to methods known in the art.

In one method of the present invention, the encoding polynucleotides are cloned into an expression vector under the control of an inducible *H. polymorpha* promoter. If secretion of the product is desired, a polynucleotide encoding a signal sequence for secretion in yeast, such as MFα1, is fused in frame with the coding sequence for the polypeptides of the invention. The expression vector preferably contains an auxotrophic marker gene, such as URA3 or LEU2, or any other marker known in the art, which may be used to complement the deficiency of an auxotrophic host. Alternatively, dominant selectable markers such as zeocin or blastacin may be used.

The expression vector is then used to transform *H. polymorpha* host cells using techniques known to those of skill in the art. An interesting and useful feature of *H. polymorpha* transformation is the spontaneous integration of up to 100 copies of the expression vector into the genome. In most cases, the integrated sequences form multimers exhibiting a head-to-tail arrangement. The integrated foreign DNA has been shown to be mitotically stable in several recombinant strains, even under non-selective conditions. This phenomenon of high copy integration further adds to the productivity potential of the system.

Plant

The present invention also contemplates the production of the recombinant gelatin of the present invention, or polypeptides from which the recombinant gelatin can be derived, in plant expression systems, including plant host cells and transgenic plants. (See, e.g., Transgenic Plants: A Production System for Industrial and Pharmaceutical Proteins, Owen and Pen, eds., John Wiley & Sons, 1996; Transgenic Plants, Galun and Breiman, eds., Imperial College Press, 1997; and Applied Plant Biotechnology, Chopra et al. eds., Science Publishers, Inc., 1999.) In cases where plant expression vectors are used, the expression of sequences may be driven by any of a number of promoters. For example, viral promoters such as the 35S and 19S promoters of CaMV may be used alone or in combination with the omega leader sequence from TMV. (See, e.g., Brisson et al. (1984) Nature 310:511-514; and Takamatsu, N. (1987) EMBO J. 6:307-311.) Plant expression vectors and reporter genes are generally known in the art. (See, e.g., Gruber et al. (1993) in Methods of Plant Molecular Biology and Biotechnology, CRC Press.)

Alternatively, plant promoters such as the small subunit of RUBISCO or heat shock promoters e.g., soybean hsp17.5-E or hsp17.3-B may be used. (See, e.g., Coruzzi, G. et al. (1984) EMBO J. 3:1671-1680; Broglie, R. et al. (1984) Science 224:838-843; Winter, J. et al. (1991) Results Probl. Cell Differ. 17:85-105; and Gurley et al. (1986) Mol. Cell. Biol. 6:559-565.) These constructs can be introduced into plant cells using Ti plasmids, Ri plasmids, plant virus vectors, direct DNA transformation, microinjection, electroporation, pathogen-mediated transfection, particle bombardment, or any other means known in the art, such as are described in a number of generally available reviews. (See, e.g., Hobbs, S. or Murry, L. E. in McGraw Hill Yearbook of Science and Technology (1992) McGraw Hill, New York, N.Y., pp. 191-196; Weissbach and Weissbach (1988) Methods for Plant Molecular Biology, Academic Press, NY, Section VIII, pp. 421-463; and Grierson and Corey, Plant Molecular Biology, 2d Ed., Blackie, London, Ch. 7-9.)

In various embodiments, the recombinant gelatin of the present invention, or polypeptides from which the present recombinant gelatin can be derived, is produced from seed by way of available seed-based production techniques using, for example, canola, corn, soybeans, rice, and barley seed. In such embodiments, the protein is recovered during seed germination/molting. In other embodiments, the protein is expressed directly into the endosperm or into other parts of the plant so that the gelatin is non-extracted, and the plant itself can serve as, for example, a dietary supplement such as a source of protein.

Promoters that may be used to direct the expression of the polynucleotides may be heterologous or non-heterologous. These promoters can also be used to drive expression of antisense nucleic acids to reduce, increase, or alter expression as desired. Other modifications may be made to increase and/or maximize transcription of sequences in a plant or plant cell are standard and known to those in the art. For example, the polynucleotide sequences operably linked to a promoter may further comprise at least one factor that modifies the transcription rate of the encoded polypeptides, such as, for example, peptide export signal sequence, codon usage, introns, polyadenylation signals, and transcription termination sites. Methods of modifying nucleic acid constructs to increase expression levels in plants are generally known in the art. (See, e.g. Rogers et al. (1985) J. Biol. Chem. 260:3731; Cornejo et al. (1993) Plant Mol Biol 23:567-568.) In engineering a plant system that affects the rate of transcription of the polynucleotides, various factors known in the art, including regulatory sequences such as positively or negatively acting sequences, enhancers and silencers, chromatin structure, etc., can be used.

Typical vectors useful for expression of foreign genes in plants are well known in the art, including, but not limited to, vectors derived from the tumor-inducing (Ti) plasmid of *Agrobacterium tumefaciens*. These vectors are plant integrating vectors, that upon transformation, integrate a portion of the DNA into the genome of the host plant. (See, e.g., Rogers et al. (1987) Meth. In Enzymol. 153:253-277; Schardl et al. (1987) Gene 61:1-11; and Berger et al. (1989) Proc. Natl. Acad. Sci. U.S.A. 86:8402-8406.)

Procedures for transforming plant cells are available in the art, including, for example, direct gene transfer, in vitro protoplast transformation, plant virus-mediated transformation, liposome-mediated transformation, microinjection, electroporation, *Agrobacterium*-mediated transformation, and ballistic particle acceleration. (See, e.g., Paszkowski et al. (1984) EMBO J. 3:2717-2722; U.S. Pat. No. 4,684,611; European Application No. 0 67 553; U.S. Pat. Nos. 4,407, 956; 4,536,475; Crossway et al. (1986) Biotechniques 4:320-334; Riggs et al. (1986) Proc. Natl. Acad. Sci USA 83:5602-5606; Hinchee et al. (1988) Biotechnology 6:915-921; and U.S. Pat. No. 4,945,050.) Standard methods for the transformation of rice, wheat, corn, sorghum, and barley are described in the art. (See, e.g., Christou et al. (1992) Trends in Biotechnology 10:239; Casas et al. (1993) Proc. Nat'l. Acad. Sci. USA 90:11212; Wan et al. (1994) Plant Physiol. 104:37; and Lee et al. (1991) Proc. Nat'l Acad. Sci. USA 88: 6389.) Wheat can be transformed by techniques similar to those employed for transforming corn or rice. (See, e.g., Fromm et al. (1990) Bio/Technology 8:833; and Gordon-Kamm et al., supra.)

Additional methods that may be used to generate plants or plant cells that can express the present recombinant gelatins, or polypeptides from which these recombinant gelatins can be derived, are well-established in the art. (See, e.g., U.S. Pat. Nos. 5,959,091; 5,859,347; 5,763,241; 5,659,122; 5,593,874; 5,495,071; 5,424,412; 5,362,865; and 5,229,112.)

The present invention further provides a method of producing polypeptides by providing a biomass from plants or plant cells which are comprised of at least one polynucleotide sequence encoding a recombinant gelatin, or a polypeptide from which recombinant gelatin can be derived, wherein such polynucleotide sequence is operably linked to a promoter to effect the expression of the polypeptide. In a further embodiment, the method additionally comprises co-expression of at least one polynucleotide sequence encoding an enzyme that catalyzes a post-translational modification, or subunit thereof, wherein such polynucleotide sequence is operably linked to a promoter. In these methods, the recombinant gelatins or collagenous polypeptides are extracted from the biomass.

Fungi

Filamentous fungi may also be used to produce the polypeptides of the instant invention. Vectors for expressing and/or secreting recombinant proteins in filamentous fungi are well known in the art, and one of skill in the art could, using methods and products available in the art, use these vectors in the presently recited methods. (See, e.g., U.S. Pat. No. 5,834,191.)

Insect

Insect cell systems allow for the polypeptides of the present invention to be produced in large quantities. In one such system, *Autographa californica* nuclear polyhedrosis virus (AcNPV) is used as a vector to express foreign genes in, for example, *Spodoptera frugiperda* cells or in *Trichoplusia* larvae. Sequences encoding the gelatins or gelatin precursors of the present invention may be cloned into non-essential regions of the virus, for example, the polyhedron gene, and placed under control of an AcNPV promoter, for example, the polyhedron promoter. Successful insertion of a coding sequence will result in inactivation of the polyhedron gene and production of non-occluded recombinant virus (i.e., virus lacking the proteinaceous coat encoded by the polyhedron gene). These recombinant viruses are then used to infect *Spodoptera frugiperda* cells or *Trichoplusia* larvae in which polynucleotides encoding the gelatins or gelatin precursors are expressed. (See, e.g., Engelhard, E. K. et al. (1994) Proc. Nat. Acad. Sci. 91:3224-3227; Smith et al. (1983) J. Virol. 46:584; and U.S. Pat. No. 4,215,051). Further examples of this expression system may be found in, e.g. Ausubel et al. (1995), supra.

Recombinant production of the polypeptides of the present invention can be achieved in insect cells, for example, by infection of baculovirus vectors containing the appropriate polynucleotide sequences, including those encoding any post-translational enzymes that might be necessary. Baculoviruses are very efficient expression vectors for the large-scale production of various recombinant proteins in insect cells. Various methods known in the art can be employed to construct expression vectors containing a sequence encoding a gelatin or gelatin precursor of the present invention and the appropriate transcriptional/translational control signals. (See, e.g., Luckow et al. (1989) Virology 170:31-39; and Gruenwald, S. and J. Heitz (1993) Baculovirus Expression Vector System: Procedures & Methods Manual, Pharmingen, San Diego, Calif.)

Animal

The present invention provides methods of expressing the recombinant gelatins of the present invention, or polypeptides from which the recombinant gelatins of the present invention can be derived, in animal systems. Such systems include mammalian and non-vertebrate host cells and transgenic animals. In mammalian host cells, a number of expression systems may be utilized. In cases where an adenovirus is used as an expression vector, sequences encoding the polypeptides of the present invention may be ligated into an adenovirus transcription/translation complex consisting of the late promoter and tripartite leader sequence. This chimeric gene may then be inserted in the adenovirus genome by in vitro or in vivo recombination. Insertion into a non-essential E1 or E3 region of the viral genome may be used to obtain a viable virus which is capable of expressing the polypeptides of the present invention in infected host cells. (See, e.g., Logan, J. and Shenk, T. (1984) Proc. Natl. Acad. Sci. 81:3655-3659.) Alternatively, the vaccinia 7.5 K promoter may be used. (See, e.g., Mackett et al. (1982) Proc. Natl. Acad. Sci. USA 79:7415-7419 (1982); Mackett et al. (1984), J. Virol. 49:857-864; and Panicali et al., (1982) Proc. Natl. Acad. Sci. USA 79:4927-4931.) In addition, various transcription enhancers known in the art, such as the Rous sarcoma virus (RSV) enhancer, may be used to increase expression in, for example, mammalian host cells.

Semliki Forest virus is a preferred expression system as the virus has a broad host range such that infection of mammalian cell lines will be possible. Infection of mammalian host cells, for example, baby hamster kidney (BHK) cells and Chinese hamster ovary (CHO) cells, using such a viral vector can yield very high recombinant expression levels. More specifically, it is contemplated that Semliki Forest virus can be used in a wide range of hosts, as the system is not based on chromosomal integration, and therefore will be a quick way of obtaining modifications of the recombinant gelatins in studies aimed at identifying structure-function relationships and testing the effects of various hybrid molecules. Methods for constructing Semliki Forest virus vectors for expression of exogenous proteins in mammalian host cells are known in the art and are described in, for example, Olkkonen et al. (1994) Methods Cell Biol 43:43-53.

Additionally, CHO cells deficient in dihydrofolate reductase (dhfr) can be transfected with an expression plasmid containing a dhfr gene and the desired polynucleotide. Selection of CHO cells resistant to increasing concentrations of methotrexate will undergo gene amplification, providing higher expression levels of the desired recombinant protein, as known in the art.

Transgenic animal systems may also be used to express the recombinant gelatins of the present invention or the polypeptides from which these recombinant gelatins can be derived. Such systems can be constructed, for example, in mammals by operably linking an encoding polypeptide to a promoter and other required or optional regulatory sequences capable of effecting expression in mammary glands. Likewise, required or optional post-translational enzymes that effect post-translational modifications, may be produced simultaneously in the target cells employing suitable expression systems. Methods of using transgenic animals to recombinantly produce proteins are known in the art. (See, e.g., U.S. Pat. Nos. 4,736,866; 5,824,838; 5,487,992; and 5,614,396; and co-pending U.S. application Ser. No. 08/987,292.)

Uses of Gelatin

Gelatin appears in the manufacture or as a component of various pharmaceutical and medical products and devices. It is estimated that about 85% of pharmaceutical products contain bovine-derived materials in some form, including the bovine gelatin currently used in various products, for example, pharmaceutical stabilizers, plasma extenders, sponges, hard and soft gelatin capsules, suppositories, etc. Gelatin's film-forming capabilities are employed in various film coating systems designed specifically for pharmaceutical oral solid dosage forms, including controlled release capsules and tablets, and other numerous pharmaceutical products in which gelatin serves as a coating intended to improve ease of administration and delivery, etc. Gelatin appears as a stabilizer in various forms, for example, in the pharmaceutical industry, e.g., in drugs and vaccines, in food and beverage products and processes, in industrial applications, e.g., concrete stabilization, and as a stabilizer in various laboratory solutions, e.g., various cell preparations.

Gelatin in various edible forms has long been used in the food and beverage industries. Gelatin is used widely in various confectionery and dessert products, particularly in puddings, frostings, cream fillings, and dairy and frozen products. Gelatin serves as an emulsifier and thickener in various whipped toppings, as well as in soups and sauces. Gelatin is used as a flocculating agent in clarifying and fining various beverages, including wines and fruit juices. Gelatin is used in various low and reduced fat products, such as mayonnaise and salad dressings, as a thickener and stabilizer, and appears elsewhere as a fat substitute. Gelatin is also widely used in microencapsulation of flavorings, colors, and vitamins. Gelatin can also be used as a protein supplement in various high energy and nutritional beverages and foods, such as those prevalent in the weight-loss and athletic industries. As a film-former, gelatin is used in coating fruits, meats, deli items, and in various confectionery products, including candies and gum, etc.

In the cosmetics industry, gelatin appears in a variety of hair care and skin care products. Gelatin is used as a thickener and bodying agent in a number of shampoos, mousses, creams, lotions, face masks, lipsticks, manicuring solutions and products, and other cosmetic devices and applications. Gelatin is also used in the cosmetics industry in microencapsulation and packaging of various products.

Gelatin is used in a wide range of industrial applications. For example, gelatin is widely used as a glue and adhesive in various manufacturing processes. Gelatin can be used in various adhesive and gluing formulations, such as in the manufacture of remoistenable gummed paper packaging tapes, wood gluing, paper bonding of various grades of box boards and papers, and in various applications which provide adhesive surfaces which can be reactivated by remoistening.

Gelatin serves as a light-sensitive coating in various electronic devices and is used as a photoresist base in various photolithographic processes, for example, in color television and video camera manufacturing. In semiconductor manufacturing, gelatin is used in constructing lead frames and in the coating of various semiconductor elements. Gelatin is used in various printing processes and in the manufacturing of special quality papers, such as that used in bond and stock certificates, etc.

Use of gelatin in photographic applications is long-established. Gelatin is used as a carrier for various active components in photographic solutions, including solutions used in X-ray and photographic film development. Gelatin, long used in various photoengraving techniques, is also included as a component of various types of film, and is heavily used in silver halide chemistry in various layers of film and paper products. Silver gelatin film appears in the form of microfiche film and in other forms of information storage. Gelatin is used as a self-sealing element of various films, etc.

Gelatin has also been a valuable substance for use in various laboratory applications. For example, gelatin can be used in various cell culture applications, providing a suitable surface for cell attachment and growth, e.g., as a coating for plates, flasks, microbeads, or other substrates, or providing a suitable protein source in growth media. Hydrolyzed or low gel strength gelatin is used as a biological buffer in various processes, for example, in coating and blocking solutions used in assays such as enzyme-linked immunosorbent assays (ELISAs) and other immunoassays. Gelatin is also a component in various gels used for biochemical and electrophoretic analysis, including enzymography gels.

Pharmaceutical

The present invention also contemplates the use of recombinant gelatin in various pharmaceutical and medical applications. In particular, in one embodiment, the present invention provides for a pharmaceutical composition comprising recombinant gelatin. In a preferred embodiment, the recombinant gelatin is derived from human sources. The present recombinant gelatins offer an advantage previously unavailable in the art: that of using gelatins derived from native human collagen sequence, thus reducing the risk of immunogenecity to the gelatin material. In addition, as the present gelatins are produced recombinantly in a controlled environment, risks of infectivity, from agents such as TSEs or from pathogens and endotoxins introduced during processing, are minimized.

Endotoxin levels of commercial materials typically range from about 1.0 to 1.5 EU/mg of gelatin. (See, e.g., Schagger, H. and G. von Jagow (1987) Anal. Biochem. 166:368-379; Friberger, P. et al. (1987) Prog. Clin. Biol. Res. 231:149-169.) In the methods of the present invention, the endotoxin levels can be reduced by two to three orders of magnitude. (See Example 8.) The present invention thus provides, in one embodiment, a recombinant gelatin derived from human sources that is virtually endotoxin-free.

In addition to providing a gelatin material without the immunogenecity and infectivity issues associated with animal-derived materials, the present invention allows for a reproducible source of consistent product. Specifically, the present gelatins can be presented as a homogeneous mixture of identical molecules. The physical characteristics desired in a particular medical application can be specifically introduced and achieved consistently. The present invention is thus able to provide a reliable and consistent product will minimize variability associated with the availability and use of current gelatin products.

In specific embodiments, the recombinant gelatin of the present invention can be used in the manufacture of capsules, including hard shell or hard capsules, typically produced from gelatin solutions, and soft shell or soft capsules, typically made from gelatin films. In specific embodiments of the present invention, a hard gel capsule comprising recombinant gelatin and a soft gel capsule comprising recombinant gelatin are provided, as are methods for manufacturing these capsules. The thermoreversibility of gelatin is a property exploited in a number of applications, for example, in the manufacture of such gel capsules and tablets. Gelatin can be heated, molded, or shaped as appropriate, and can be used to form a capsule or tablet coating that has unique properties at homeostatic temperatures. A selected gelatin can begin to melt at mouth temperature, easing swallowing, and become liquid at internal body temperature, such as within the stomach. In one embodiment, the present invention provides recombinant gelatins with the dissolution rates of commercially available capsules and coatings. In another embodiment, the present invention provides recombinant gelatins with improved resiliency, appropriate for use in capsules and tabletting.

In certain applications, such as the manufacture of gel capsules, the brittleness and hardness developed by gelatin over time is an important parameter that can limit the shelf-life and usefulness of currently available animal-source gelatins. The ability to maintain viscosity over time would be a valuable asset, especially for manufacturers of gelatin-containing products, who currently buy gelatin in sizable lots in order to maintain consistency of manufactured products. Furthermore, some manufacturing processes, such as the manufacture of hard gel capsules, currently require a blend of gelatin types, e.g., of type A and type B gelatins, in order to produce a material with the desired properties, as the use of type B gelatin alone results, for example, in a hard gel capsule that is too brittle for manufacture and use.

The recombinant gelatins of the present invention are of greater purity and are better characterized than currently available materials. Thus, the present gelatins can provide a stable material, and one more reproducible and predictable in its behavior. Furthermore, using the methods of the present invention, one could engineer a recombinant gelatin that possessed the structural features of both types of gelatin in a single molecule or in a well-characterized mixture of molecules.

The recombinant gelatin of the present invention can also be used as a stabilizer in various pharmaceutical products, for example, in drugs or vaccines. (See, e.g., co-pending, commonly-owned U.S. patent application Ser. No. 09/710,249, entitled "Recombinant Gelatins in Vaccines," filed 10 Nov. 2000, incorporated herein by reference in its entirety.) Therefore, in one embodiment, the present invention provides a stabilizing agent comprising recombinant gelatin, wherein the stabilizer is suitable for use in pharmaceutical applications. In a preferred embodiment, the recombinant gelatin is recombinant human gelatin.

Different regions of various collagens are associated with various activities, for example, various regions of type III collagen have been associated with active sites involved in the clotting cascade. Therefore, in one embodiment, the present invention contemplates the use of polynucleotides encoding recombinant gelatins that contain specific active regions of a particular collagen or of particular collagens. Such polynucleotides can be used in a variety of ways, for example, in microarrays. Such polynucleotides could thus be used as a diagnostic tool to identify altered links of mRNA polynucleotides corresponding to collagenous domains of interest in a sample. The encoded polypeptides could be used in various methods of screening for drugs or compounds that could inhibit or enhance the activity and/or expression associated with particular collagenous domains.

The present gelatin can also be used in encapsulation, including microencapsulation, and in tabletting, suppositories, and various medical emulsions. The present invention also contemplates the use of the recombinant gelatin provided herein in medical sponges, e.g., hemostatic sponges, etc., in wound treatment and in various surgical applications, e.g., as sponges used to prevent leakage after port removal in fetoscopy and other procedures. Therefore, in one aspect, the present invention comprises a sponge comprising recombinant gelatin, wherein the sponge is suitable for use in medical procedures. In a preferred embodiment, the recombinant gelatin is recombinant human gelatin.

The recombinant gelatins of the present invention can be designed to possess specific physical properties suitable for use in particular applications. The present invention provides methods for varying characteristics such as molecular weight, gel strength, and pH of the final gelatin formulation to produce gelatins with specific properties as desired, and to thus meet customer's specifications to a degree unattainable with currently available materials. Moreover, such formulations allow the customer to explore refinements of existing processes and formulations, as well as to develop new applications, for the present recombinant gelatins.

The molecular weight distributions of commercially available animal-derived soluble gelatins, such as those used in formulation of vaccines, range from about 0 to 30 kD and from about 0 to 60 kD. (See Examples 7 and 9.) The present invention provides for a method of producing recombinant human gelatins, under suitable hydrolysis conditions, that results in recombinant human gelatins with molecular weight distributions which correspond with the commercially available gelatins, and can be used for the same purposes. Additionally, the present invention provides methods for producing gelatins with a narrower molecular weight distribution, for example, about 10 to 30 kDa, or about 30 to 50 kDa, not available from commercial materials.

The recombinant gelatin of the present invention, and compositions thereof, can also be used in various surgical procedures, including in biodegradable conduits for directing and supporting nerve regeneration, in colloidal volume replacement in major surgeries, in gelatin sponge plugs used to seal various port sites, such as catheterization sites and other incisions or wounds, and in polyester grafts as an infection-resistant sealant. (See, e.g., Mligilche, N. L. et al. (1999) East Afr. Med. J. 76(7):400-406; Beyer et al. (1997) Br. J. Anaesth. 78(1):4-50; Luks et al. (1999) Am. J. Obstet. Gynecol. 181 (4):995-996; and Farooq et al. (1999) J. Surg. Res. 87(1):57-61.)

The present pharmaceutical compositions can be administered to a subject for treatment of various joint conditions, including arthritis, athrosis, and other conditions related to the degeneration of cartilage and joint flexibility. In a preferred embodiment, the recombinant gelatin contains a modified amino acid sequence which possesses higher concentrations of arginine, hydroxyproline, and hydroxylysine, and other amino acids related to the production of collagens and proteoglycans in cartilage. (See, e.g., Oesser et al. (1999) J. Nutr. 129(10):1891-1895.) Microspheres synthesized with the gelatins of the present invention are also contemplated. Such microencapsulated particles can be used, for example, in directed delivery of therapeutic proteins or small molecules, providing a noninflammatory and biocompatible delivery system. (See, e.g., Brown et al., (1998) Arthritis Rheum, 41:2185-2195.). In another aspect, the present invention contemplates oral administration of the recombinant gelatins of the present invention to alleviate disease activity in rheumatoid arthritis. (Arborelius et al. (1999) Rheumatol Int 18:129-135.) In ingested pharmaceutical products, it might be desirable to provide recombinant gelatin having stability against degradation in the acidic environment of the stomach, gut, etc.

Techniques for encapsulation, and various formulations and drug delivery systems, are available in the art and are described in numerous sources. (See, e.g., Gennaro, A. R., ed. (1990) *Remington's Pharmaceutical Sciences*, 18$^{th}$ ed., Mack Publishing Co., Easton Pa.) The most effective and convenient route of administration and the most appropriate formulation for a particular situation can be readily determined by methods known in the art.

Suitable routes of administration may, for example, include oral, rectal, transmucosal, or intestinal administration and parenteral delivery, including intramuscular, subcutaneous, intramedullary injections, as well as intrathecal, direct intraventricular, intravenous, intraperitoneal, intranasal, or intraocular injections. Vaccines, for example, can be delivered intravenous, nasal, or oral, and can take the form of live attenuated, subunit, monovalent, divalent, trivalent vaccines, etc. Formulations for enteric release, etc., are also contemplated. The composition may be administered in a local rather than a systemic manner. The present invention also provides a pharmaceutical composition comprising recombinant gelatin wherein the composition is suitable for delivery as a spray, for lingual or nasal delivery.

Food

In the food industry, gelatin's physical properties and pure protein composition make it suitable for use in a variety of ways, including as a component of various edible products and nutritional supplements. Gelatin can be a food product in its own right, providing a carbohydrate-free, pure protein source. In addition, gelatin's physical and structural characteristics are useful in various food preparation and packaging applications. For example, gelatin is used as a gelling and thickening agent; as an emulsifier and foaming agent; to prevent curdling or protein-liquid separation; for "feel," or to improve consistency and texture; to retain moisture; and in adhesion and packaging, for example, as an edible film.

Edible gelatin can serve as a particularly valuable source of pure protein. Therefore, in one aspect, the present invention provides a protein supplement comprising recombinant gelatin. The gelatin of the present invention can be produced with, for example, specific and desired amounts of essential amino acids. The present invention provides for the production of various edible gelatins, whether in gel, leaf, or powder form, with characteristics optimal for a particular application or end product.

The present invention provides for recombinant gelatin products comprising different ratios of amino acid residues. Typically, gelatin contains most of the amino acids essential for humans, including for example, lysine, arginine, leucine, and isoleucine. In one embodiment, the present invention provides recombinant gelatin comprising the specific ratios of amino acids desired. For example, gelatin used in foods intended to supplement an athlete's diet might comprise higher levels of residues such as lysine, which is beneficial to muscle growth, and arginine, which, as a precursor to creatine, is involved in the energy metabolism of muscle cells. Gelatin can serve to enhance the nutritional value of foods in general by completing and increasing the amino acid composition of other protein sources, for example, meats and dairy products.

Gelatin has minimal or bland taste, and can thus serve as a palatable and nutritional food supplement. Hydrolyzed gelatin, for example, is used as a substitute for more concentrated solutions of carbohydrates in desserts and candies and in other caloric foods, reducing the caloric content. Gelatin can also serve as a source of protein in foods with high nutritional value, for example, low-calorie foods produced in the diet industry or high-energy foods. In addition to serving as a protein source, gelatin can serve as a carbohydrate-free carrier or filler substance in, for example, spray or dried instant food products and flavorings, or as a clarifying and fining agent in, for example, wines and juices.

The ability of gelatin to impart desirable characteristics, including, for example, texture, color, and clarity, is highly valued. The texture of such products depends to a large degree on the types of ingredients used, formulation variables, and how the products are processed and handled. In confectionery applications, for example, gelatin appears in a variety of gelled products, such as pastilles and popular gummy products. Gelatin is used as a gelling agent, providing textures ranging from soft and elastic to short and hard. The texture and mouth-feel of the finished product is dependent on the bloom strength, concentration, and formulation of gelatin used. In addition, gelatin's colloidal properties provide a substrate for colors and dyes, allowing the desired opacity or clarity, as well as color, of the end product. Therefore, in one aspect, the present invention allows for the use of a gelatin that provides the desired textural properties, brilliance, and clarity, in the manufacture of gelled confectionery products.

In another aspect, an appropriate gelatin is selected which has a relatively low viscosity, as high viscosity can produce undesirable 'tailing' of the depositing syrup during manufacture, causing defective products. Generally speaking, the higher the bloom value of the gelatin, the harder the product becomes, so that by increasing the gelatin content, the product becomes harder and chewier in texture.

A property of gelatin widely exploited in, for example, the production of aerated confectionary products, is its ability to produce and support a foam, and to promote rapid setting at the air/liquid interface by forming a film around entrapped air bubbles. Aerated products constitute a large family of confectionery products, including marshmallows, frostings, nougats, and cookie and wafer fillings. The degree of aeration and setting time required for a particular product depends on the type and grade of gelatin used, together with the concentration of gelatin in the final product. Altering the type and proportion of gelatin used can vary the texture of aerated products. For example, gelatins with high bloom values, or gel strength, produce a shorter chew, whereas gelatins with lower bloom values provide a more elastic texture.

Gelatin serves a number of functions in the manufacture of fruit chews, and other sugar-pulled confectionery product types, such as toffees and caramels, which contain fats and are slightly aerated. For example, gelatin assists in the emulsification of fats, improving dispersion and stability; provides desirable texture and chewiness, as well as foaming ability; and contributes to the shelf-life of the final product, such as by controlling sucrose crystallization. Gelatins with a Bloom of about 150 to 200 to are typically used in these products at usage levels of 0.5-1.5% w/w. Therefore, in one aspect, the present invention contemplates a recombinant gelatin with a Bloom of about 150 to 200 for use in edible products.

Gelatin provides cohesive texture in cream pastes, which contain both solid and liquid phases consisting of powdered sugar and fats dispersed in a sugar syrup. Gelatin acts as a binder to prevent a crumbly texture and to inhibit cracking. Gelatin's binding properties are also utilized in lozenges and compressed tablets. In products such as licorice, gelatin, often combined with an agent such as wheat flour, acts as a binder, greatly improving moisture retention, and preventing cracking and crumbling during manufacture. Gelatin also helps prevent confectionary products, such as, for example, licorice, from drying out in storage, improving product shelf life. The present invention thus provides, in one embodiment, a binding agent comprising recombinant gelatin, which binding agent can be a component of edible products. The present invention further provides a moisturizing agent comprising recombinant gelatin, which moisturizing agent is suitable for use in edible products.

Gelled products are available in various forms, including ready-to-eat products, dry blended powdered mixtures, or tablets in which the sugars, gelatin, acids, flavoring, and coloring have been dissolved and gelled. Gelatin's ability to form elastic-textured thermo-reversible gels with melting points around 25-35° C. is exploited in such uses. The final texture, rigidity, and setting rate of these gelling products are controlled by the concentration and physical properties of the gelatin, most particularly, bloom strength and viscosity levels. In the production of gelatin desserts, the use of a lower concentration of a higher-grade gelatin to produce a gelled product of a particular rigidity would provide advantages, including economic advantage, as well as improved clarity and color development, compared to the use of a higher concentration of a lower strength gelatin. Therefore, in one embodiment, the present invention provides a gelling agent comprising recombinant gelatin, wherein the gelling agent is suitable for use in an edible product.

Gelatin is often used in the manufacture of various dairy products, such as ice cream, yogurt, and puddings, in which a particular texture and mouth feel is desired; in particular, gelatin provides a smooth, even-textured consistency and creamy mouth feel. Gelatin is used in combination with other hydrocolloids as a thickener and stabilizer in low fat mayonnaise and salad dressings.

With the expansive growth in the number and desirability of low- and no-fat dairy products, gelatin can make an outstanding contribution to the product texture, body, and mouth feel of a finished product. With its fat-like melting characteristics, a gelatin having a melting point of around 25-35° C. provides the desirable sensory properties, or 'melt-in-the-mouth' characteristics, thus simulating the texture of the full-fat product.

In a health-conscious society, gelatin is well-suited for use as a stabilizer in low or reduced fat and non-fat yogurt products, adding to the body and mouth-feel, and creating a smooth, delicate, and creamy texture in the absence of fat. Additionally, gelatin stabilizes these products by preventing syneresis, or the separation of whey proteins. In this regard, gelatin products function to form a gel network which binds water, preventing exudation and separation of the whey proteins, thus helping product shelf-life. Gelatin is also used in the manufacture of thickened creams, in which the gelling and emulsifying properties of gelatin are used to increase cream viscosity. Gelatin also has widespread use in sour cream, soft cheese products, and acidic milk desserts, such as cheesecakes, and in flavored milk-based desserts, such as mousses, chiffons and souffles. The cream viscosity can be varied as desired by altering the concentration and gelling properties of the gelatin used. Typical gelatin levels for such uses range from 0.2-0.8% w/w, although higher or lower gel strengths could be desired in various products. The present invention provides a stabilizing agent comprising recombinant gelatin.

There is increasing demand in the food and health industries for reduced fat or fat-free products. Gelatin's dietetic properties, including its ability to provide protein in the absence of fat, make it useful in the weight-loss industry, as well as in products designed for patients, convalescents, and individuals with special dietary sensitivities or needs. Gelatin's protein content adds carbohydrate-free nutritional value. In addition to its nutritional value, gelatin is highly digestible and can thus be administered in liquid foods that are easily absorbed. Pure gelatin contains no fats, sugars, purines, or cholesterols. Gelatin's physical properties, protein content, and lack of strong taste make it a preferable fat substitute in many products. Gelatin is widely used as an emulsion stabilizer in, for example, products such as low-fat butters and margarines. As a thickening and binding agent, gelatin can replace in whole or in part the fat content in various food products. For example, gelatin can replace highly caloric binders such as cream, butter, and other dairy fats; egg yolks; and other starchy products. In addition, gelatin's moisture retaining qualities are helpful in binding large amounts of water, allowing for greater post-prandial satisfaction and fullness.

The sensory or mouth feel of gelatin is critical, as many fat-free or reduced fat products seek to mimic as closely as possible the mouth feel, as well as the taste, of fats. By using gelatin in a low-fat formulation, it is possible to achieve a texture comparable to a full-fat product, thereby achieving a lower calorie content while preserving a preferred texture and mouth-feel. The amount of gelatin used is dependent on the percentage of fat, if any, contained in the finished product. For instance, at a fat content of 60%, 0.5% w/w gelatin is used, while at lower fat levels of 25%, approximately 3.5% w/w gelatin is used to maintain product integrity and sensory appeal. Gelatin produced according to the present invention can possess a melting-point similar to that of the food products in which it is included or, preferably, the body or mouth temperature of humans, resulting in melting of gelatin at eating temperatures and a correspondingly rich mouth-feel. In addition, gelatin's bland taste will not interfere with the flavorings of a particular food product. Finally, gelatin is highly digestible.

Using gelatin as a fat substitute thus allows for a reduction in calories without a corresponding reduction in texture and richness, and without corresponding negative effects on taste and digestibility. The present invention, in one aspect, provides a fat substitute comprising recombinant gelatin, wherein the fat substitute is intended for use in edible products. In a preferred embodiment, the recombinant gelatin has a melting point of from about 25 to about 35° C.

Gelatin improves the appearance and slicing characteristics of various canned and preserved foods, including meats such as cooked ham, by penetrating and filling any cavities in the tissue. In canned meat products, gelatin serves to absorb the juices that are released during the retorting process, improving the slicing properties and giving a pleasing appearance to the product. In these instances, a gelatin should be selected that has a low calcium content as precipitation of calcium phosphate from the phosphates in the meat juices can occur. In canning applications, such as canned seafood, a gelatin with a high gel strength is used to withstand the thermal treatment applied during the sterilization process. Depending on the extent of sterilization and the get strength selected, gelatin levels usually range from 0.5-5.0% w/w. Gelatin also serves as a binder and a gelling agent in canned seafoods and meats and in a variety of jelled (aspic) products.

Gelatin finds application for sausage coatings, where it is used as an adhesive agent in binding spices to the surface of products such as salamis. The sausage is dip-coated in a concentration solution of gelatin that typically has a high bloom and high viscosity giving the gelatin time to set and inhibiting run-off from the product surface. Such coatings are also used, for example, in the manufacture of soybean and other substitute meat products, and in the coating of various fruits, meats, and delicatessen items. In one aspect, the present invention provides an edible coating comprising recombinant gelatin.

Gelatin is also used in microencapsulation of various flavors, colors, and other additives, and of vitamins.

Specifically contemplated are various recombinant gelatins that can be used as stabilizing agents, thickening agents, film-forming agents, binding agents, edible coatings, gelling agents, protein supplements, emulsifying agents, microencapsulants for colors, flavors, and vitamins, etc., and can be used in various food supplements, including nutritional and diet supplements, and fat substitutes. In one embodiment, the gelatin of the present invention is used in the processing or packaging of, or as a component in, foods prepared for consumers with Kosher, Halal, vegetarian, or other diets that restrict the ingestion of food containing specific animal-source products.

In addition to being used in edible products intended for human consumption, gelatins are used as binding agents in the manufacture of bars and pellets in pet foods, snacks, and chewables. In addition to the structural advantages gelatin offers in these products, gelatin's high protein content can contribute positive effects such alleviating symptoms of degenerative diseases of the animal skeletal system, as well as improving pelt growth and texture.

Photographic

In another aspect, the present invention comprises a photographic composition comprising recombinant gelatin. Preferably, the recombinant gelatin is partially hydroxylated. Gelatin is a key component of various photographic processes and products, including, for example, films and paper. Gelatin is used as a binder in light-sensitive products, where its gel-setting and film-forming properties make for clear, uniform, and durable coatings which can involve multiple coatings in a single application. Gelatin as a binding agent creates and provides the uniform consistency, solidification, or cohesion desired. Gelatin also stabilizes coupler and dye emulsions in color photographic products.

Gelatin is indispensable in photographic coatings including silver halide emulsion layers, top coat or surface layers, inter-layers, and back-coats. The chemical and colloidal properties of gelatin enable precise precipitation and chemical ripening of photographic silver halide emulsions. Some emulsifying fluids use non-gelling fish gelatins, which may remain liquid in solutions at concentrations as high as 40%, and at temperatures as low as 20° C.

In one embodiment, the recombinant gelatin has a low molecular weight and a low setting temperature. In another embodiment, the recombinant gelatin has a low setting point, but a higher molecular weight than available in current non-gelling piscine-derived gelatins or in animal-derived gelatin hydrolysates.

The recombinant gelatin of the present invention can be used in various photographic applications, for example, for the support of silver halides on both film and paper. In one embodiment, the recombinant gelatin has a setting temperature of between 15° and 25° C. The recombinant gelatin can be spray-dried and offered as a low density, cold water soluble powder or film, and is thus advantageous for use in various technical applications, for example, photoresist systems. The present gelatin can also be used in gelatin filters. The present invention contemplates photographic gelatin products custom-designed to meet the exacting properties of each particular need, as well as methods for making such gelatins.

Other

The recombinant gelatins of the present invention offer various technical advantages over commercially available gelatin due to its more particular and integrated chemical make-up, and the corresponding consistency in its physical properties. The recombinant gelatin of the present invention can thus be used in technical applications which currently involve extracted gelatin. For example, the present gelatin can be used in a variety of industrial processes, including, but not limited to, paper sizing and photogravure, collotype, screen printing processes, microencapsulated dyes, copy transfer papers and other papers and boards coated with gelatin through the formation of a coacervate complex with gum arabic. Gelatins of the present invention can also be used in electroplating to ensure smooth deposition and as a protective colloid in some polymerization reactions, and as a coating or film-forming agent in semiconductor manufacture.

In another embodiment, the present gelatin is used as a binder for special quality papers, including stock certificates, bank notes, etc. The present gelatin further serves as a bonding agent for use in match paste, providing a lower density and more even combustion for matches, as well as fastening of abrasive particles on a canvas or paper backing to produce abrasive papers.

The distinctive properties of gelatin, including its ability to serve as a protective colloid, and to alter its electrical charge with changes in pH, combine to make gelatin a material suitable for use in microencapsulation. Gelatin and its derivatives can thus be used in a variety of microencapsulation devices and techniques, for example, in the microencapsulation of inks for carbon-free paper; fragrances for advertising and sample manufacture; chemicals used in multi-component adhesives; and vitamins and nutritional supplements. The microencapsulation capabilities of gelatin and its derivatives are also useful in the manufacture of packaging materials, including packaging allowing minimal permeability for oxygen, aromas, and water vapor. Gelatin is thus widely used in flexible packaging, such as packaging for food, pharmaceuticals, and other sensitive products.

The adhesive effect and reduction of surface tension provided by gelatins render them useful in leaf fertilizers. Due to the stability and slow degradation of the amino acids of gelatin, the precisely adjusted nitrogen concentration provided by the fertilizer is thus maintained and made available of a longer period of time. Gelatins are also useful as a biologically degradable binding agent in the manufacture of fertilizer pellets.

Due to its amino acid composition, gelatins can serve as complex sources of nitrogen, useful, for example, in the synthesis of penicillin by *Penicillium chrysogenum*, as well as, for example, in the manufacture of various starter cultures and antibiotics. (See, e.g., Leonhartsberger, et al. (1993) J Biotechnol 30:299-313.)

The recombinant gelatins of the present invention can be used in various laboratory applications, in which the reproducibility and uniformity of the recombinant gelatins of the present invention will be greatly valued, minimizing unwanted variability in laboratory processes and compositions. For example, the present recombinant gelatins can be used in various tissue culture applications, providing a suitable protein source in growth media, and, in some applications, providing a cell growth matrix or scaffolding, or other surface for cell attachment and growth. The present invention also provides a cell preservation formulation comprising recombinant gelatin. Such formulation could, for example, be used to preserve a preparation of platelet cells, protecting the solution until administration and use. The present invention contemplates biological buffers comprising hydrolyzed or low gel strength recombinant gelatins, such as various blocking and coating solutions. In further embodiments, the present invention provides reproducible recombinant gelatins for use in various gels used for biochemical and electrophoretic analysis, including enzymography gels.

The present invention also encompasses microcarrier beads coated with recombinant gelatin. Such microcarriers, used, e.g., in mammalian cell culture, provide a growth surface for attachment-dependent cells. Polysaccharide and polystyrene beads, for example, can be coated with the recombinant gelatins of the present invention to provide a suitable surface for cell attachment and growth. In one embodiment, the microcarrier beads of the present invention are coated with specific recombinant gelatins containing active collagenous domains capable of inducing differentiation and growth of particular cells.

Different regions of various collagens are associated with various activities, for example, various regions of type III collagen have been associated with active sites involved in the clotting cascade. Therefore, in one embodiment, the present invention contemplates the use of polynucleotides encoding recombinant gelatins that contain specific active regions of a particular collagen or of particular collagens. Such polynucleotides can be used in a variety of ways, for example, in microarrays.

Recombinant gelatins, polypeptides, and polynucleotides encoding the recombinant gelatins of the present invention can be used in novel microarray technologies and screening methodologies. Collagen fibrils and immobilized collagen bind strongly to platelets, as platelets have multiple binding sites for collagen that encompass several collagen molecules polymerized to each other. The interaction of platelets with collagen through their collagen receptors results in activation of the platelets and subsequent formation of platelet aggregates.

Recombinant gelatins consisting of biologically active regions of collagen type III, for example, can be prepared as microfibers that consist of a uniformity, purity, and reproducibility unattainable with current collagen and gelatin sources. Microfibers derived from the present recombinant gelatins can be presented on substrates, e.g., arrays or chips, used to screen for compounds that prevent platelet aggregation through interaction with, e.g., type III collagen, or any other fibril-forming collagen. Chemical compounds, small molecules, peptides, or other biological molecules (such as antibodies) can be screened for their ability to prevent, reduce, or slow the process of clot formation or platelet aggregation, mediated by platelet interactions with specific regions within a collagen fiber, such as, for example, RGD sequences. Additionally, microarrays would also be useful for examination of the interaction of different types of integrins with various regions of collagens and gelatin micro-fibers. Microfibers produced from recombinant gelatins from any of the fibril-forming collagens, e.g., collagen type I, type II, type III, type V, or type XI, could be used in screening for collagen-induced platelet aggregation antagonists.

Also contemplated are microarrays of polynucleotides encoding recombinant gelatins or fragments thereof. Such microarrays are useful in screening for and isolation of variants of collagen- or gelatin-encoding polynucleotides, e.g. DNA or RNA, and in determining differential levels of expression in, for example, normal vs. diseased tissue.

In another embodiment, the present invention provides purified recombinant human gelatins for use in the differentiation of progenitor cells, for tissue regeneration therapies, and for tissue engineering. Components of the extracellular matrix are involved in the regulation of cell proliferation and differentiation. The use of gelatin microspheres implanted with basic fibroblast growth factor accelerated fibroblast proliferation and capillary formation in an artificial dermis model. (Kawai et al. (2000) Biomaterials, 21:489-499.) Collagen type IV inhibited cell proliferation and glial cell differentiation, while promoting the differentiation of neuronal progenitors. (Ali et al. (1998) Brain Res Dev Brain Res 110: 31-38.) Additionally, collagen type I induced the osteogenic differentiation of bone marrow stromal cells, while collagen types II, III, and V did not. (Mizuno and Kuboki (1995) Biochem Biophys Res Commun 211:1091-1098; and Mizuno et al. (1997) Bone 20:101-107.)

In general, the use of gelatins in cell culture lead to higher cell density and increased and prolonged cell viability in hematopoietic stem cells and other progenitor cells. (Tun et al. (2000) ASAIO J 46:522-526.) Gelatins used as a carrier matrix or delivery vehicle have supported osteochondrial differentiation in the delivery of bone marrow-derived mesenchymal progenitor cells and for mesenchymal cell based cartilage regeneration therapies. (Angele et al. (1999) Tissue Eng 5:545-554; Ponticiello et al. (2000), J Biomed Mater Res 52:246-255; and Young et al. (1998) J Orthop Res 16:406-413.) The present invention provides recombinant gelatins for use in cell culture, such as, for example, in promoting cell attachment, cell proliferation, and cell differentiation. In certain embodiments, the present invention provides methods for producing specific recombinant gelatins designed to provide the desired cell attachment, cell proliferation, or cell differentiation activities. For example, if promoting the differentiation of neuronal progenitor cells was desired, a recombinant gelatin could be produced containing the specific regions of collagen type IV responsible for this activity.

The present invention provides a cosmetic composition comprising recombinant gelatin. This composition can be administered to a subject to improve and repair rough and broken nails and to improve the texture of hair. Gelatin's hypoallergenic and hydrating properties, and its ability to provide texture, color, and clarity, and to form films, make it an essential ingredient in various cosmetics and toiletries. For example, gelatins are valuable components of hair care products, such as shampoos and conditioners. In one embodiment, the present invention provides a moisturizing agent comprising recombinant gelatin, which moisturizing agent is appropriate for use in cosmetic applications. The film forming properties of gelatin can improve the gloss and handling of hair, especially in damaged hair previously treated with chemical preparations. Gelatin is also used in various cosmetic processes, including hair treatment procedures such as permanent waving and bleaching, in which proteins such as gelatin are used to protect hair structure. The use of recombinant gelatin in lotions, masks, creams, lipsticks, and other cosmetic products is also contemplated, as the film-forming properties of gelatin contributes to skin smoothness and softness. In one aspect, the present invention contemplates a cosmetic composition comprising recombinant gelatin, which is administered to treat roughened or weak nails, etc.

The distinctive properties of gelatin, including its ability to serve as a protective colloid, and to alter its electrical charge with changes in pH, combine to make gelatin a material suitable for use in microencapsulation. Gelatin and its derivatives can thus be used in a variety of microencapsulation devices and techniques, for example, in the microencapsulation of fragrances for advertising and sample manufacture.

The following examples explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

EXAMPLES

Unless otherwise stated, the following materials and methods were used in the examples of the present invention.

Example 1

Direct Expression of Recombinant Gelatins

Specific fragments of the α1(I) cDNA from human type I collagen were amplified by PCR and cloned into the plasmid pPICZαA or pPIC9K (Invitrogen Corp., Carlsbad, Calif.).

The specific PCR primers used in cloning are set forth in Table 1 below. Specific recombinant gelatins are identified in Table 2 as SEQ ID NOs: 15 through 25, and 30, 31, and 33. These recombinant gelatins are additionally identified by reference to human prepro-α1(I) collagen. (Genbank Accession No. CAA98968.) The expression plasmids used contained α1(I) cDNA sequences of different sizes fused to the yeast mating factor alpha prepro secretion sequence. Other signal sequences known in the art can also be used, for example, the yeast invertase (SUC2), the yeast acid phosphatase (PHO) sequences, the native pro-collagen signal sequence, and the signal sequence for human serum albumin. A signal sequence that provides the optimal level of expression for a specific gelatin fragment in a specific expression system should be chosen.

TABLE 1

| SEQ ID NO: | SEQUENCE |
|---|---|
| 1 | GTATCTCTCGAGAAGAGAGAGGCTGAAGCTGGTCTGCCTGGTGCCAAGGGT |
| 2 | TAGACTATTATCTCTCGCCAGCGGGACCAGCAGG |
| 3 | GTATCTCTCGAGAAGAGAGAGGCTGAGGCTGGAGCTCAGGGACCCCCTGGC |
| 4 | ATGCTCTAGATTATTACTTGTCACCAGGGGCACCAGCAGG |
| 5 | GTATCTCTCGAGAAGAGAGAGGCTGAAGCTGGCCCCATGGGTCCCTCTGGTCCT |
| 6 | TGCTCTAGATCATTAAGCATCTCCCTTGGCACCATCCAA |
| 7 | TGCTCTAGACTATTAAGGCGCGCCAGCATCACCCTTAGCACCATC |
| 8 | TGCTCTAGATCATTAAGGCGCGCCAGGTTCACCGCTGTTACCCTTGGG |
| 9 | TGCTCTAGATCATTATCTCTCGCCTCTTGCTCCAGAGGG |
| 10 | GTGCCCGTGGTCAGGCTGGTGTGATGGGATTCCCTGGACCTAAAGGTGCTGCTTAAT |
| 11 | CTAGATTAAGCAGCACCTTTAGGTCCAGGGAATCCCATCACACCAGCCTGACCACGGGCACCAG |
| 12 | ATGCTCTAGATTATTAAGGAGAACCGTCTCGTCCAGGGGA |
| 13 | CTAGTCTAGATTATCTTGCTCCAGAGGGGCCAGGGGC |
| 14 | CTAGTCTAGATTAGCGAGCACCTTTGGCTCCAGGAGC |
| 32 | AGCTTCTAGATTATTAGGGAGGACCAGGGGACCAGGAGGTCC |

TABLE 2

| SEQ ID NO: | PCR PRIMERS USED | AMINO ACID SEQUENCE | MOLECULAR WEIGHT |
|---|---|---|---|
| 15 | SEQ ID NO:5 and SEQ ID NO:6 | residue 179 to residue 280 | 9,447 Da |
| 16 | SEQ ID NO:5 and SEQ ID NO:8 | residue 179 to residue 439 | 23,276 Da |
| 17 | SEQ ID NO:5 and SEQ ID NO:9 | residue 179 to residue 679 | 44,737 Da |
| 18 | SEQ ID NO:10 and SEQ ID NO:11 | residue 531 to residue 589 | 5,250 Da |
| 19 | SEQ ID NO:1 and SEQ ID NO:2 | residue 531 to residue 631 | 8,947 Da |
| 20 | SEQ ID NO:1 and SEQ ID NO:7 | residue 531 to residue 715 | 16,483 Da |
| 21 | SEQ ID NO:1 and SEQ ID NO:4 | residue 531 to residue 781 | 22,373 Da |
| 22 | SEQ ID NO:1 and SEQ ID NO:12 | residue 531 to residue 1030 | 44,216 Da |
| 23 | SEQ ID NO:3 and SEQ ID NO:7 | residue 615 to residue 715 | 8,213 Da |
| 24 | SEQ ID NO:3 and SEQ ID NO:4 | residue 615 to residue 781 | 14,943 Da |
| 25 | SEQ ID NO:3 and SEQ ID NO:12 | residue 615 to residue 1030 | 36,785 Da |
| 30 | SEQ ID NO:3 and SEQ ID NO:13 | residue 615 to residue 676 | 5,517 Da |
| 31 | SEQ ID NO:3 and SEQ ID NO:14 | residue 615 to residue 865 | 22,126 Da |
| 33 | SEQ ID NO:1 and SEQ ID NO:32 | residue 531 to residue 1192 | ~65 kDa |

The expression plasmids were introduced into *Pichia pastoris* cells by electroporation, and transformants were selected by complementation of a his4 auxotrophy (pPIC9K vectors) or by resistance to zeocin (pPICZαA vectors). Recombinant protein expression was regulated by the methanol-inducible alcohol oxidase promoter ($P_{AOX1}$). The *Pichia pastoris* host cells contained integrated copies of the α and β subunits of human prolyl 4-hydroxylase (P4H), the enzyme responsible for the post-translational synthesis of hydroxyproline in collagen, and have been previously described. (See, e.g., Vuorela, M. et al. (1997) EMBO J 16:6702-6712.)

The yeast strains were grown in buffered minimal glycerol media, and recombinant protein expression was induced using the same media with methanol (0.5%) substituted for glycerol as the carbon source, as described in the Invitrogen *Pichia* Expression Manual. Gelatin-producing strains were identified by 10-20% Tricine SDS-PAGE analysis of conditioned media and prolyl 4-hydroxylase activity in extracts from shake flask cultures. Co-expression of prolyl 4-hydroxylase and the collagen fragments resulted in the expression of recombinant gelatins with native human sequences.

The fragments were expressed and secreted into the media. Recombinant gelatin was recovered and purified from the media by acetone precipitation, anion or cation exchange chromatography, or any combination thereof. Acetone precipitation was performed at 4° C. by addition of acetone to cell-free culture supernatants to a final concentration of 40%. The resulting precipitate, consisting primarily of endogenous yeast proteins, was collected by centrifugation. Acetone was then added to this supernatant to a final concentration of 80%, causing the gelatin to precipitate, which was then collected by centrifugation, dialyzed overnight against water, and lyophilized. High purity gelatin was obtained by a combination of anion and cation exchange chromatography. Chromatographic purifications were performed at room temperature.

Estimation of the sizes of collagenous proteins by electrophoresis, compared to calculation of molecular weight based on amino acid composition, is known in the art (Butkowski et al. (1982) Methods Enzymol 82:410-423) N-terminal sequence analysis of the recombinant gelatins demonstrated correct processing of the prepro sequence which was fused to the gelatin fragments in order to direct the protein to the yeast secretory pathway. The gelatins produced in this system contained only sequences derived from human collagen. Additionally, the recombinant gelatins represented the major component of the conditioned media, as *Pichia pastoris* cells secrete very few proteins.

The expressed recombinant gelatins were of discrete sizes, ranging from about 5 kDa to about 65 kDa as measured on SDS-PAGE, corresponding, for example, to gelatins of ~5 kDa (lane 2, SEQ ID NO:18), ~10 kDa (lane 3, SEQ ID NO:19), ~16 kDa (lane 4, SEQ ID NO:24), ~18 kDa (lane 5, SEQ ID NO:20), ~20 kDa (lane 6, SEQ ID NO:28) (also having a calculated molecular weight of 17,914 Da, not set forth in Table 1), ~33 kDa (lane 7, SEQ ID NO:27) (also having a calculated molecular weight of 29,625 Da, not set forth in Table 1), ~41 kDa (lane 8, SEQ ID NO:25), and ~50 kDa (lane 9, SEQ ID NO:22), as indicated in FIG. 1 (lane 10 represents hydrolyzed recombinant human collagen type I, prepared as described in Example 10).

Example 2

Human Recombinant Gelatins Support Cell Attachment Activity

The recombinant human gelatin fragments of the present invention demonstrated in vitro cell attachment activity. In the following assay, 96-well Maxisorp plates (Nunc) were coated with the following recombinant human gelatin domains from the α1 chain of human type I collagen, as described in Example 1 and listed in Table 2: SEQ ID NO:19, SEQ ID NO:20, SEQ ID NO:21, and SEQ ID NO:22. VITROGEN bovine collagen (Cohesion Technologies; Palo Alto Calif.) and bovine serum albumin served as positive and negative controls, respectively. Each of the proteins was diluted to 0.1 mg/ml in 0.1 M NaHCO$_3$, pH 10.0, and the plates coated overnight at 4° C. Human foreskin fibroblasts (HFF) or human umbilical vein endothelial cells (HUVEC, from Clonetics, passage 5), were seeded onto the coated plates and incubated for 60 minutes at 37° C. Experiments were performed in triplicate.

Figure 2A:
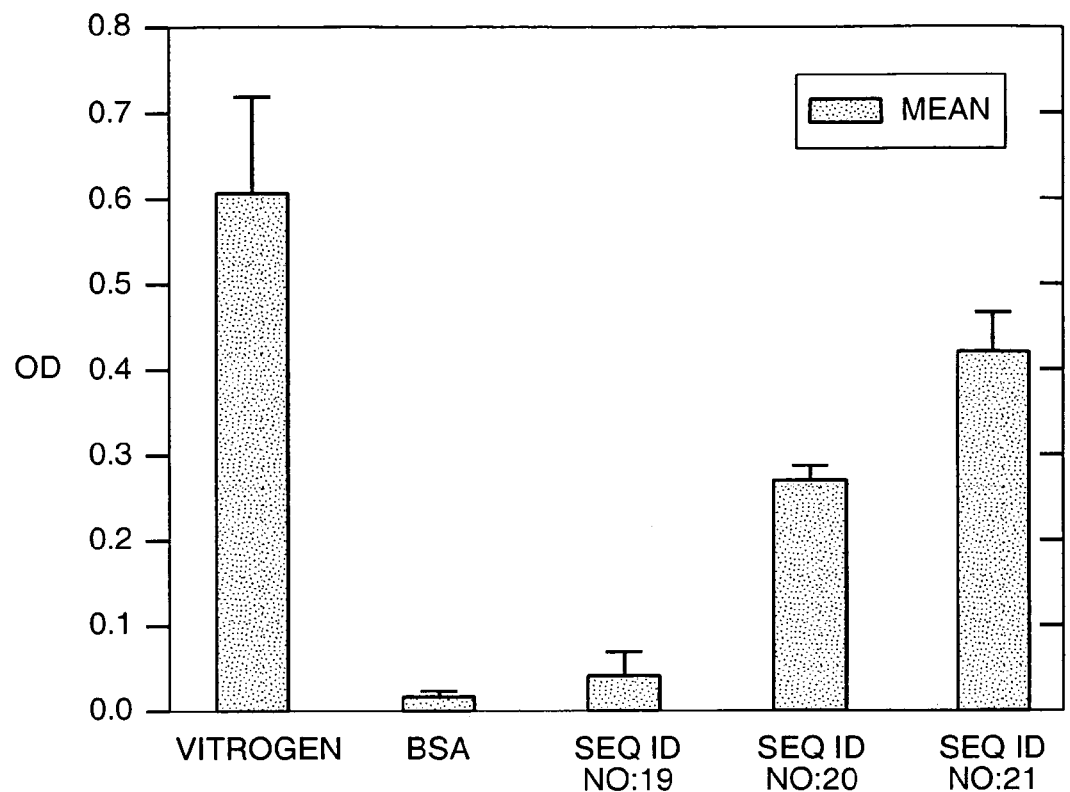
FIGS. 2A and 2B set forth results demonstrating that recombinant gelatins support cell attachment.
Figure 2B:
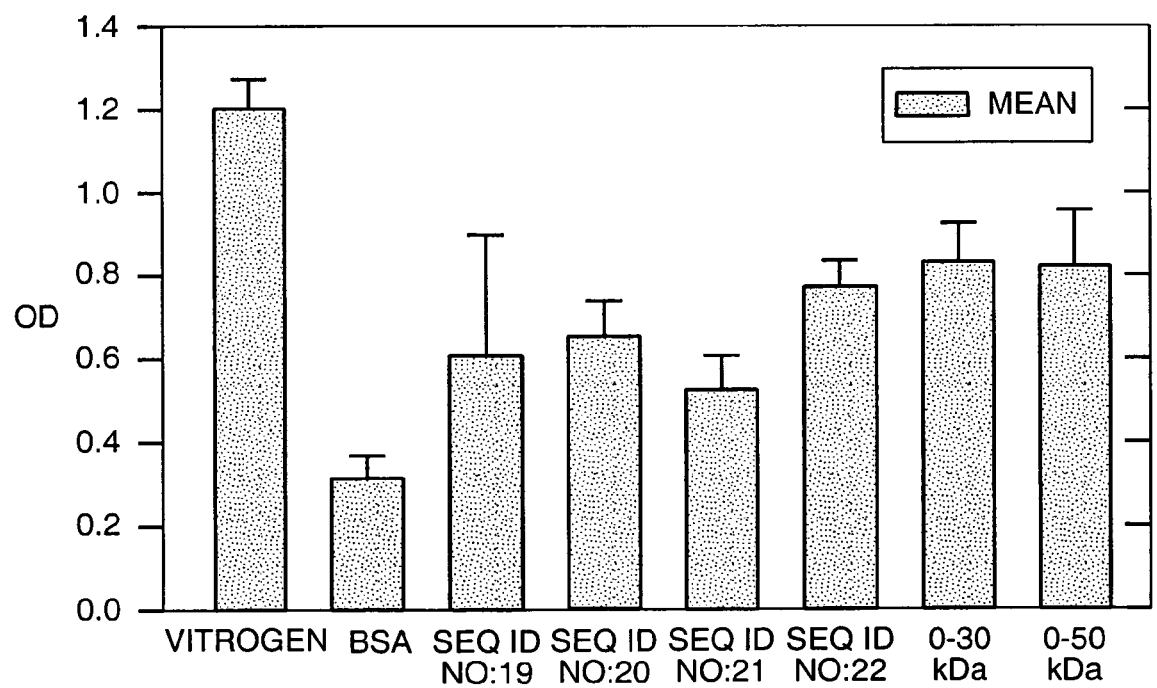

The degree of cell attachment was then measured using Reagent WST-1, the absorbance of which was read at 450 mM in an ELISA reader. FIG. 2A shows that recombinant human gelatins supported HFF attachment to Maxisorp plates, and, for these cells, attachment was directly proportional to the molecular weight of the recombinant human gelatin coated in each well. Specifically, the recombinant gelatins of SEQ ID NO:19, SEQ ID NO:20, and SEQ ID NO:21 supported HFF attachment to a higher extent than that seen with BSA. FIG. 2B shows that the different recombinant human gelatins supported endothelial cell attachment. Cell attachment activity was also demonstrated with recombinant human gelatin prepared by thermal hydrolysis of recombinant human collagen (described below in Example 9), using recombinant gelatins having molecular weight ranges of 0-30 kDa and 0-50 kDa.

Example 3

Identification of a Proteolytically Stable Gelatin Fragment

Recombinant gelatin fragments were found to be proteolytically modified during their expression and accumulation in the media of recombinant *Pichia pastoris* cells. Expression of several different portions of the helical domain of the α1 chain of type I collagen lead to the identification of a recombinant gelatin that had superior stability with respect to proteolysis. Three different gelatin fragments were cloned into plasmid pPICZαA, and their relative stabilities evaluated during recombinant protein expression in *Pichia pastoris* cells.

Figure 3:
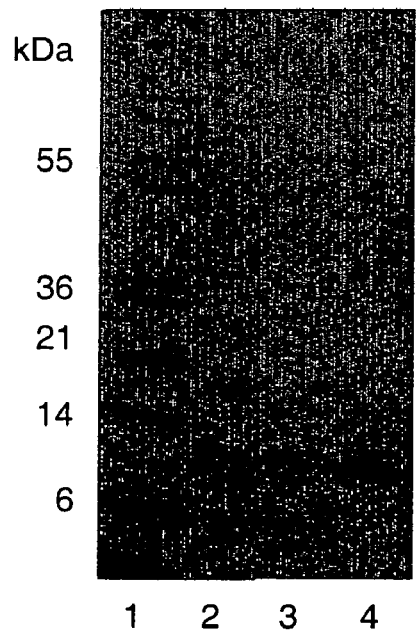
FIG. 3 sets forth results demonstrating the production of proteolytically stable recombinant gelatins.

The first strain used is described above in Example 2, corresponding to SEQ ID NO:19. Additional strains were created using plasmids encoding human α1(I) helical domain amino acid residues 179-280 (SEQ ID NO:15) and 615-715 (SEQ ID NO:23). These recombinant gelatins were constructed as described in Example 1, using primers SEQ ID NO:5 and SEQ ID NO:6, and SEQ ID NO:3 and SEQ ID NO:7. The PCR products were digested with XhoI and XbaI, cloned, and prepared for electroporation as described above. The strains were grown, protein expression induced, and the expressed gelatin fragments compared by SDS-PAGE. FIG. 3 shows that the recombinant gelatin of SEQ ID NO:15 (lane 2) and the recombinant gelatin of SEQ ID NO:19 (lane 3) underwent proteolysis, while the recombinant gelatin of SEQ ID NO:23 (lane 4) remained completely intact. This result demonstrated that recombinant gelatin fragments of the present invention could be produced which have superior stability.

Example 4

Expression of Hydroxylated Recombinant Human Gelatin

Prolyl 4-hydroxylase activity has not been detected in yeast. A *Pichia pastoris* strain has been engineered to express active prolyl 4-hydroxylase and has been used previously to produce hydroxylated collagen. (See U.S. Pat. No. 5,593,859.) To express hydroxylated recombinant human gelatin, this strain was transformed with a gelatin expression cassette encoding 100 amino acids of a recombinant of human α1(I) collagen (SEQ ID NO:19, Table 2), generated by PCR using the primers SEQ ID NO:1 and SEQ ID NO:2. The PCR DNA product (~330 bp) was digested with XhoI-XbaI and ligated into the XhoI-XbaI sites of pPICZαA (Invitrogen), creating plasmid pDO7.

Figure 4A:
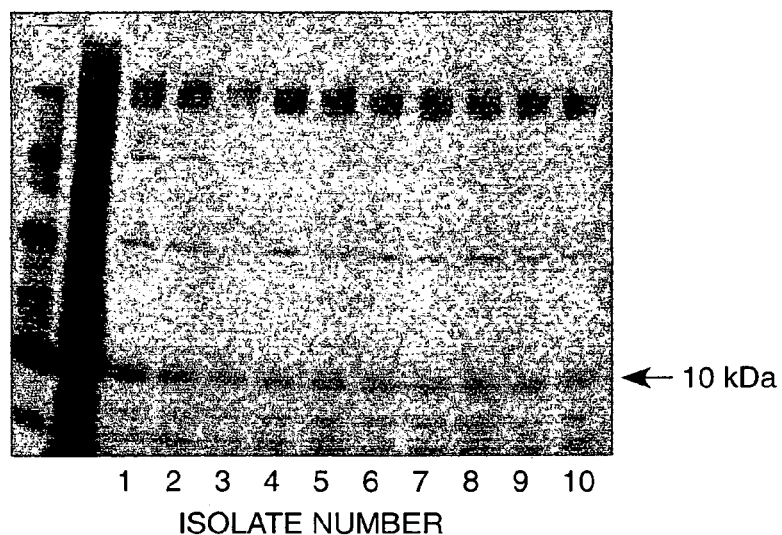
FIGS. 4A and 4B set forth results demonstrating the production of hydroxylated recombinant gelatins.
Figure 4B:
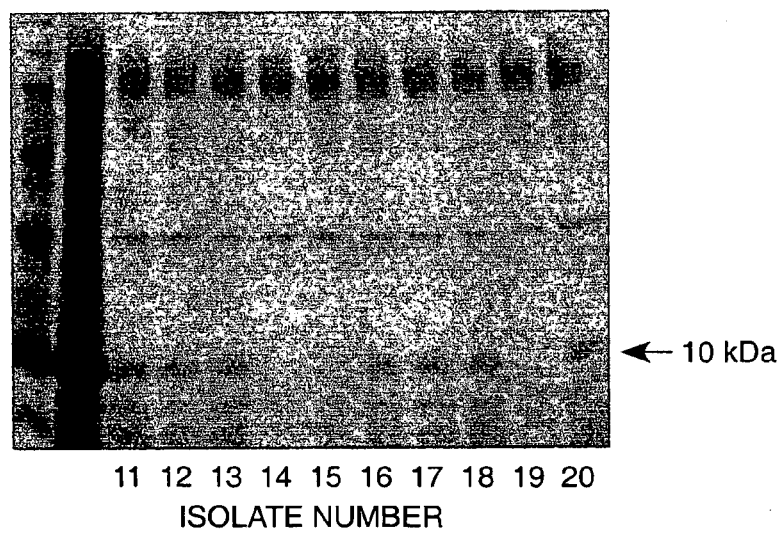

A 1048 bp Cel II-AgeI fragment was isolated from pDO7 which contained the 3' portion of the AOX1 promoter region, the mating factor alpha secretion signal, the recombinant gelatin of SEQ ID NO:19, the polylinker sequence from pPICZαA, and 56 base pairs of the AOX1 transcription terminator. This fragment was ligated into the Cel II-AgeI sites of pPIC9K (Invitrogen) to create pDO41. *Pichia pastoris* strain αβ8 (his4) was transformed with StuI-linearized plasmid pDO41 by electroporation, plated on minimal dextrose plates, and transformants were selected that complemented the his4 auxotrophy. Approximately 20 his$^+$ transformants were grown and induced with methanol as described in Example 1. Strains that expressed SEQ ID NO:19 were identified by SDS-PAGE analysis of the conditioned media. (FIGS. 4A and 4B.)

Recombinant gelatin fragments from positive strains were purified from the media by acetone precipitation, and analyzed further by amino acid analysis, as described, e.g., in Hare, P E. (1977) Methods in Enzymology 47:3-18. Amino acid analysis of the gelatin product from one of the strains demonstrated the presence of hydroxyproline in the secreted recombinant gelatins. The ratio of hydroxyproline to proline was determined to be 0.29 in gelatin isolated from the strain shown in shown in FIGS. 4A and 4B, isolate #2, indicating co-expression of gelatin and prolyl 4-hydroxylase.

Non-hydroxylated recombinant gelatins were expressed and purified from a *Pichia pastoris* strain that does not express prolyl 4-hydroxylase. Proline residues within this recombinant gelatin were subsequently converted to hydroxyproline residues in vitro using prolyl 4-hydroxylase enzyme activity. A gelatin expression plasmid was created by PCR using primers SEQ ID NO:3 and SEQ ID NO:4, leading to the expression of recombinant gelatin of SEQ ID NO:24. The 525 base pair PCR product was purified and digested with XhoI-XbaI and ligated to XhoI-XbaI digested pPICZαA. The plasmid was linearized with PmeI and electroporated into *Pichia pastoris* strain X-33 (Invitrogen). Transformants were selected by growth on YPD plates containing 500 µg/ml zeocin. Strains were tested for gelatin expression as described above and recombinant non-hydroxylated gelatin was purified from the media of a positive isolate. Conditioned media was concentrated 10-fold by pressure dialysis using a 10 kDa molecular weight cut-off membrane, and the sample was dialyzed against Buffer A (50 mM Tris-HCl pH 9.0, 50 mM NaCl). The dialyzed material was chromatographed on a Q-sepharose column equilibrated in Buffer A. Gelatin does not bind to this column under these conditions, and therefore, was present in the flow-through fraction. The majority of the contaminating yeast proteins bound to the column and eluted with Buffer B (Buffer A+0.5 M NaCl).

The flow-through fraction was dialyzed against 50 mM sodium acetate, pH 4.5, and the recombinant gelatin further purified on a SP-sepharose column equilibrated in the same buffer. The recombinant gelatin bound to the column, and was step-eluted with 0.2 M NaCl. The purified gelatin, at 1 mg/ml, was heat denatured (100° C. for 10 minutes) and mixed with purified P4H at a enzyme to substrate ratio of 1:30 in the presence of the following components: 50 mM Tris-HCl pH 7.8, 2 mM ascorbate, 2 mM α-ketoglutarate, 0.1 mM $FeSO_4$, 10 µM DTT, 10 mg/ml bovine serum albumin, and 100 units of catalase (Sigma Chemical Co., St Louis, Mo.). (See, e.g., Kivirikko, K. I. and Myllyla, R. (1982) Methods in Enzymology 82:245-304; and Vuori, K., et. al. (1992) Proc. Natl. Acad. Sci. 89:7467-7470.) The reaction was allowed to proceed at 37° C. for 16 hours.

Figure 5:
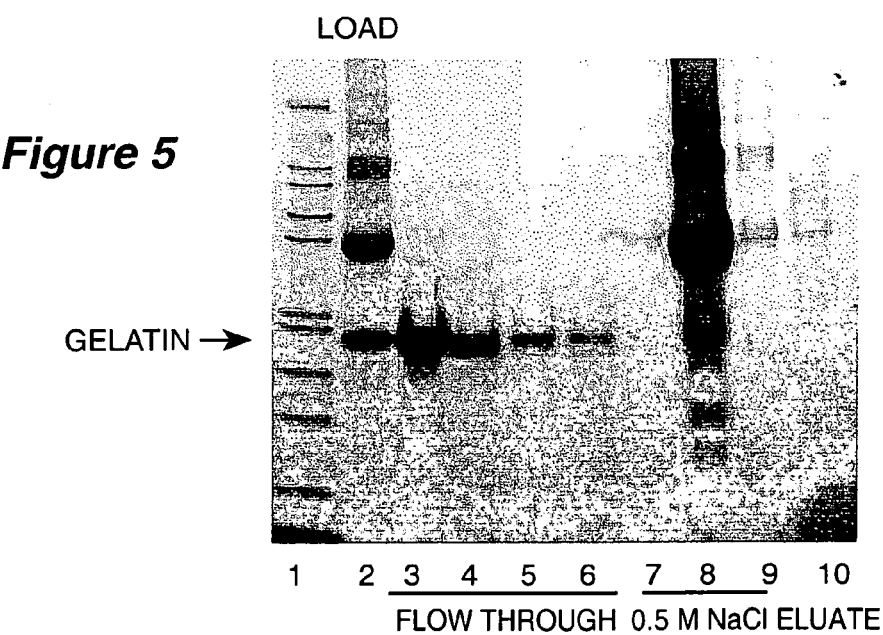
FIG. 5 sets forth results showing the purification of recombinant gelatin following in vitro hydroxylation.

The recombinant gelatin was then purified by chromatography on Q-sepharose as described above. The bound proteins were eluted from the column with 0.5 M NaCl and collected. (FIG. 5, lanes 7, 8, and 9.) The flow-through and eluate fractions were analyzed by SDS-PAGE to demonstrate the purity of the recovered gelatin. (FIG. 5.) Amino acid analysis of the gelatin was performed following dialysis of the flow-through fractions. (FIG. 5; lanes 3 through 6.) The amino acid analysis showed that the gelatin was 87% hydroxylated. Hydroxylation of 100% is achieved when the number of moles of hydroxyproline/moles of proline+moles of hydroxyproline in gelatin equals 0.5.

Example 5

Stability of Gelatins in the Presence or Absence of Prolyl 4-hydroxylase

An 18 kDa recombinant gelatin (SEQ ID NO:20) was expressed according to the methods described above. The expressed fragments were analyzed by gel electrophoresis. Recombinant gelatin expressed in the presence of prolyl 4-hydroxylase had markedly greater stability than the gelatin expressed in the absence of prolyl 4-hydroxylase. (See FIGS. 6A, 6B, and 6C.)

A role of proline hydroxylation on recombinant human gelatin stability and an enhancement of stability was explored in prolyl 4-hydroxylase-expressing *Pichia pastoris* strains. A plasmid encoding SEQ ID NO:20 (pDO32) was constructed by PCR using primers SEQ ID NO:1 and SEQ ID NO:7. The PCR product was purified, digested, and cloned as described above. The same α1(I) cDNA fragment was expressed in host cells lacking prolyl hydroxylase, and in host cells containing the α and β prolyl 4-hydroxylase subunits. Three *Pichia pastoris* strains were electroporated with PmeI-linearized pDO32: strain X-33 (wild-type *Pichia pastoris*), two prolyl 4-hydroxylase-expression strains: strain P4H-2, and strain αβ8, as described in the U.S. Pat. No. 5,593,859 and in Vourela et al. (1997) EMBO J 16:6702-6712.

Figure 6A:
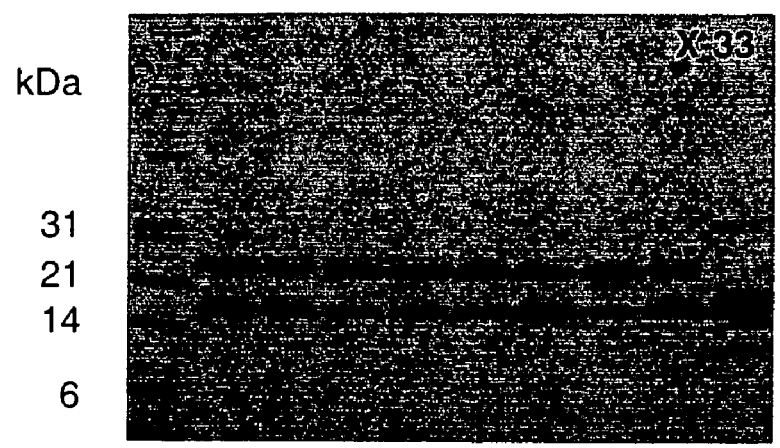
FIGS. 6A, 6B, and 6C set forth results showing the stability of recombinant gelatins expressed in the presence or absence of prolyl 4-hydroxylase.
Figure 6B:
Figure 6C:

Transformants were selected by resistance to 500 µg/ml zeocin. Eight isolates from each transformation were grown and induced as described, and the stability of the expressed recombinant human gelatin was analyzed by SDS-PAGE. (See FIGS. 6A, 6B, 6C.) In wild-type *Pichia pastoris* strain X-33, approximately equimolar amounts of intact recombinant gelatin and a proteolytic fragment (which migrated just below the recombinant gelatin on the gel, indicated by the arrow at the right of the figure) were observed. (FIG. 6A, strain X-33.) In both strains that co-express prolyl 4-hydroxylase, the amount of the proteolytic fragment was significantly reduced, demonstrating that co-expression of prolyl 4-hydroxylase along with recombinant human gelatin enhanced gelatin stability by substantially reducing proteolysis of the gelatin. (FIGS. 6B and 6C, strain P4H-2 and strain αβ8, respectively.)

Example 6

Figure 7A:
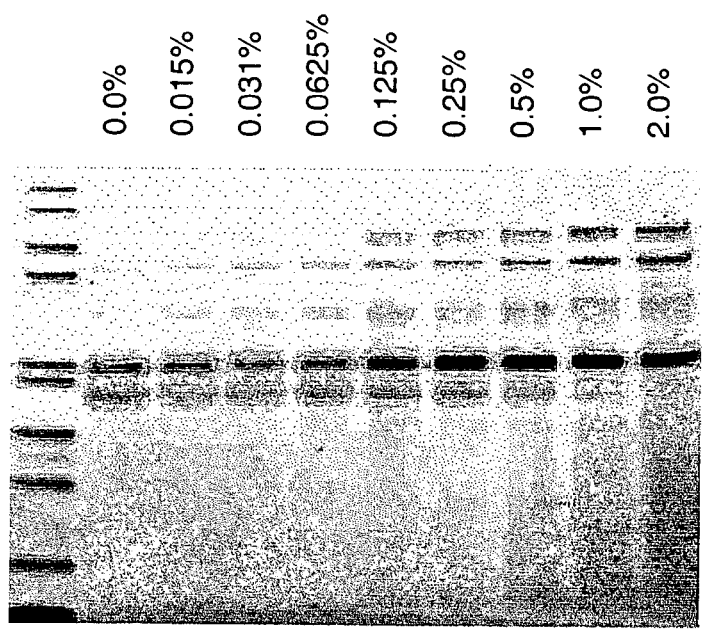
FIGS. 7A and 7B set forth results demonstrating enhanced recombinant gelatin expression by supplementation of expression media FIG. 8 sets forth results comparing commercially available gelatins to cross-linked recombinant gelatin.
Figure 7B:
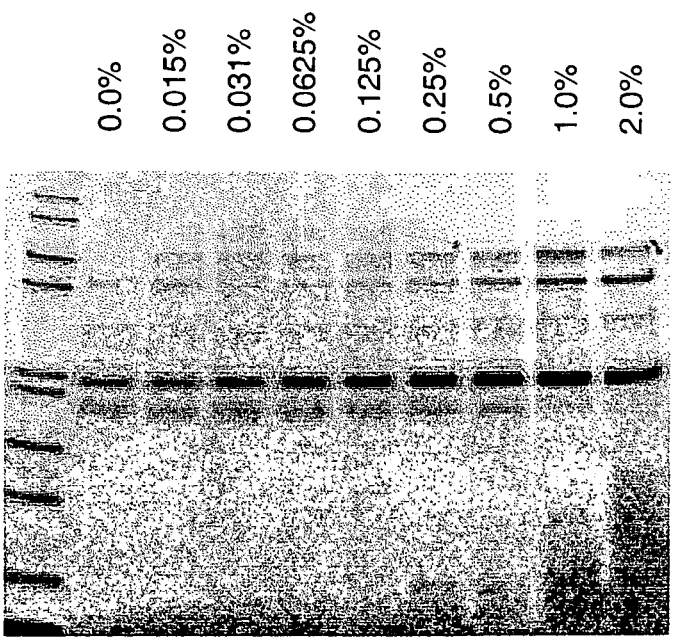

Enhanced Recombinant Human Gelatin Expression by Supplementation of Expression Media Previous reports have indicated that casamino acid-supplemented media decreased the amount of proteolysis seen during expression of certain proteins in *Pichia pastoris*. (Clare, J. J. et al. (1991) Gene 105:202-215.) The breakdown of the present recombinant human gelatin expressed in *Pichia pastoris* was measured following enrichment of the expression media with various supplements. In this particular study, the *Pichia pastoris* strain αβ8 described in Example 5, which expressed recombinant human gelatin fragment SEQ ID NO:20 was employed. (Example 5 and Table 2.) Recombinant gelatin was induced in media supplemented with a range of concentrations (0-2%) of various supplemental components, including casamino acids, casitone, yeast extract, peptone, peptamin, tryptone, Gelatone, lactalbumin, and soytone. Several formulations, including lactalbumin hydrolysate, soytone, casitone, and peptamin (Difco Laboratories, Detroit, Mich.) increased recombinant gelatin expression levels. (FIGS. 7A and 7B, lactalbumin and soytone, respectively.)

These results indicate that specific media supplements employed during the expression of recombinant gelatins can lead to increased production. In one aspect, the use of soytone as a media supplement provided a plant-derived (rather than animal-derived) media component that lead to increased expression of recombinant gelatin. This would provide an animal material-free environment for production of recombinant gelatin that could be used in a variety of applications.

Example 7

Cross-linking of Recombinant Human Gelatins

A slurry of recombinant human collagen (obtained as described in U.S. Pat. No. 5,593,859) was prepared by dissolving 10.8 mg of recombinant human collagen type I in 5 ml of water, followed by dialysis against 20 mM sodium phosphate, pH 7.2. The final recombinant human collagen concentration of the slurry was approximately 2 mg/ml. Preparation of cross-linked recombinant human gelatin was performed by adding 10 μl or 5 μl of a 20% solution of 1-ethyl-3-(3-dimethlyaminopropyl) carbodiumide hydrochloride (EDC, Pierce Chemical Co.) to 1 ml of the recombinant human collagen slurry described above. The cross-linking reaction occurred overnight at room temperature. Unreacted EDC was removed by dialysis against water.

Figure 8:
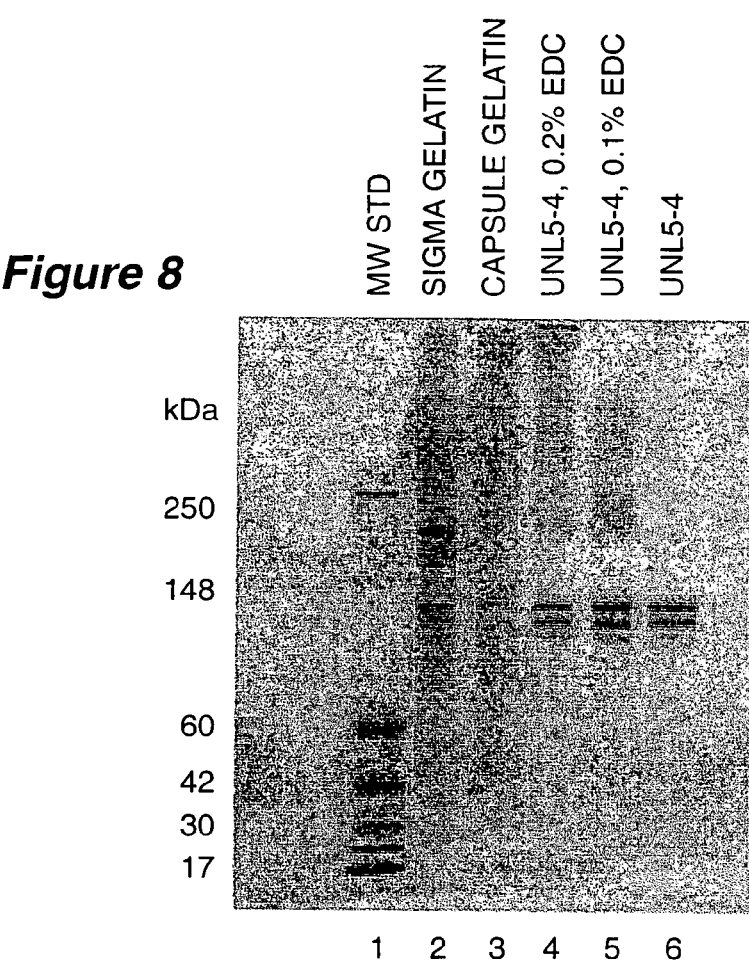

The resulting cross-linked recombinant human gelatins were analyzed by 6% glycine SDS-PAGE analysis. FIG. 8 shows an SDS-PAGE comparison of recombinant human gelatin (lane 6, labeled UNL-5-4), cross-linked recombinant human gelatin (lane 5, labeled UNL 5-4, 0.1% EDC; lane 4, labeled UNL 5-4, 0.2% EDC), commercially available hard capsule gelatin (lane 3), and commercially available gelatin (Type A, from porcine skin, approximately 300 Bloom, lane 2) obtained from Sigma Chemical Co. As shown in the SDS-PAGE analysis of FIG. 8, the commercial capsule gelatin and Sigma gelatin contained α-chain (molecular weight of approximately 110 kDa) as a major component, as well as a smear of higher molecular weight gelatin components (with molecular weight ranging from approximately 200-250 kDa). The recombinant human collagen was composed of α-chain only. Following cross-linking, however, the cross-linked recombinant gelatin was composed of α-chain as well as a smear of higher molecular weight gelatins, similar to that observed in commercial gelatin and commercial capsule gelatin. This indicated that recombinant human gelatins displaying a molecular weight distribution similar to that of commercial capsule gelatins could be produced by cross-linking recombinant human collagen. Cross-linked recombinant gelatins would have use in applications in which increased gel strength and increased viscosity would be desirable.

Example 8

Endotoxin Levels of Commercially Available Gelatin and Soluble Recombinant Human Gelatin Endotoxin levels of soluble gelatin obtained commercially from Kind & Knox (K&K) and the recombinant human gelatins of the present invention (made as described in Example 9) were determined using the Limulus Ameobocyte Lysate test, as known in the art. (See, e.g., Friberger, P. et al. (1987) Prog. Clin. Biol. Res. 231:149-169.) Three different gelatin concentrations were examined. As shown in Table 3, the recombinant human gelatins generated by thermal hydrolysis of recombinant human collagen type I (rhcI) of the present invention were virtually endotoxin-free. The endotoxin levels of commercially available materials were about 1 to 1.5 EU/mg of protein. The methods for producing gelatin as described in the present invention resulted in gelatins having substantially lower endotoxin levels, by two to three orders of magnitude, than those of the commercial preparations. Such low endotoxin levels make the recombinant gelatins of the present invention especially attractive for use in certain applications, such as use in pharmaceutical stabilization.

TABLE 3

| Gelatin Concentration (mg/ml) | K&K Gelatin (EU/mg) | Recombinant Human Gelatin (EU/mg) |
|---|---|---|
| 3 | 1.03 | <0.005 |
| 1.5 | 1.41 | <0.005 |
| 0.75 | 1.29 | <0.006 |

Example 9

Derivation of Gelatins by Thermal and Acid Hydrolysis

Hydrolysis procedures (acid, thermal, and enzymatic) were developed to produce soluble recombinant human gelatins with molecular weight distributions similar to those of currently available soluble animal-derived gelatins, used, for example, as stabilizers in the formulation of vaccines. For these experiments, intact recombinant human collagen type I and type III were used as starting materials. By varying the hydrolysis conditions, it was possible to vary the molecular weights of the final materials, producing materials of defined molecular weights.

Figure 9:
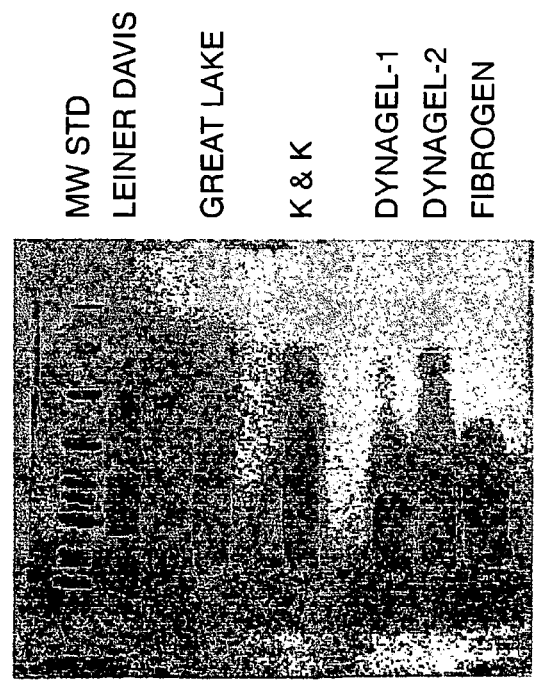
FIG. 9 sets forth results comparing the molecular weight distribution of commercially available gelatins.
Figure 10A:
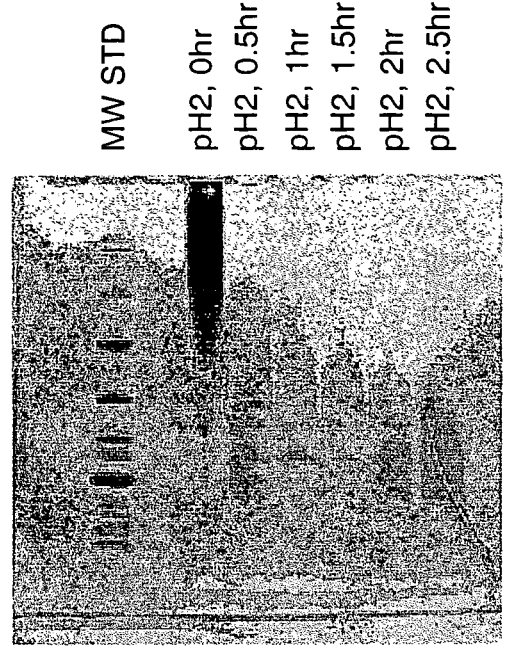
FIGS. 10A, 10B, 10C, 10D, 10E, and 10F set forth results showing the hydrolysis of commercially available gelatins performed at 120° C.
Figure 10B:
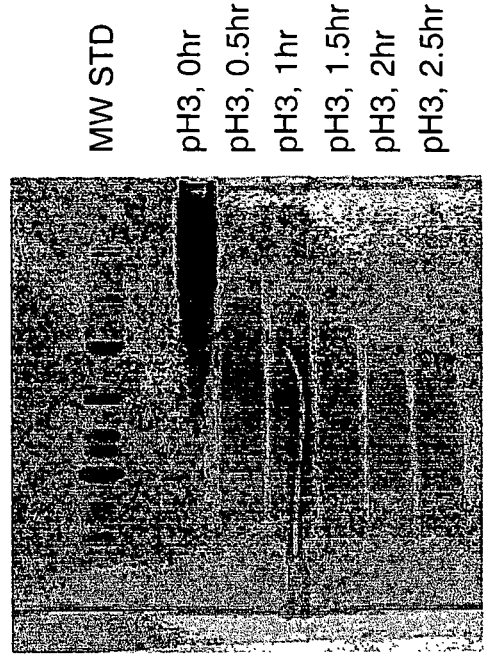
Figure 10C:
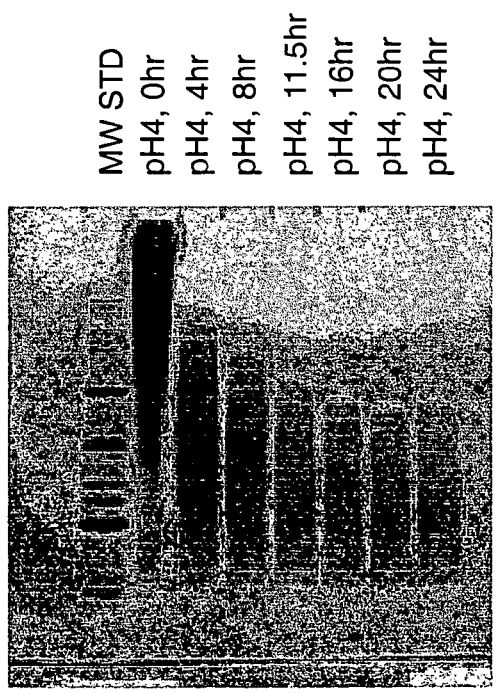
Figure 10D:
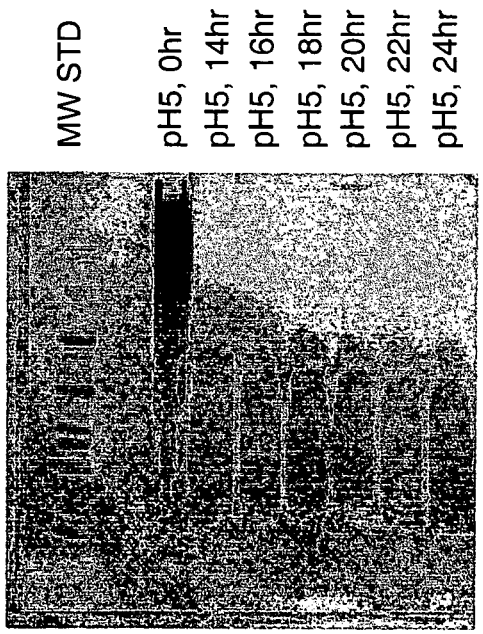
Figure 10E:
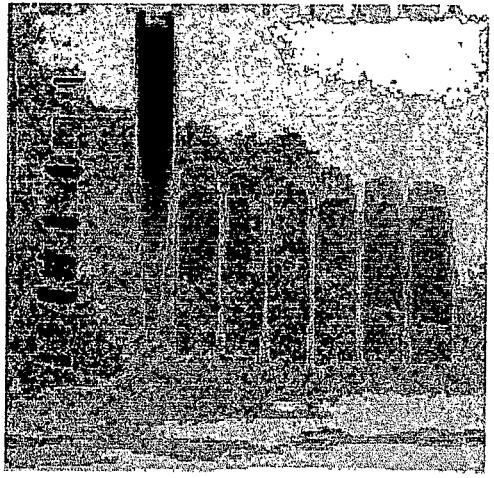
Figure 10F:
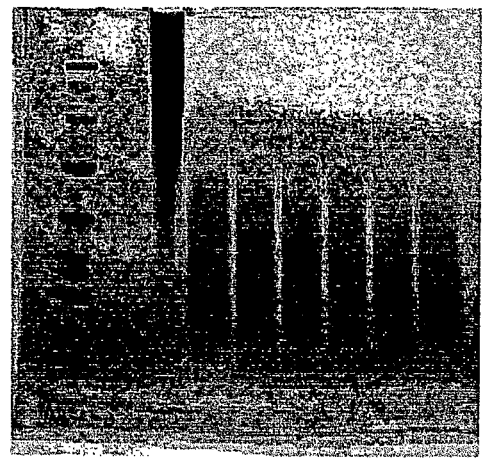
Figure 11A:
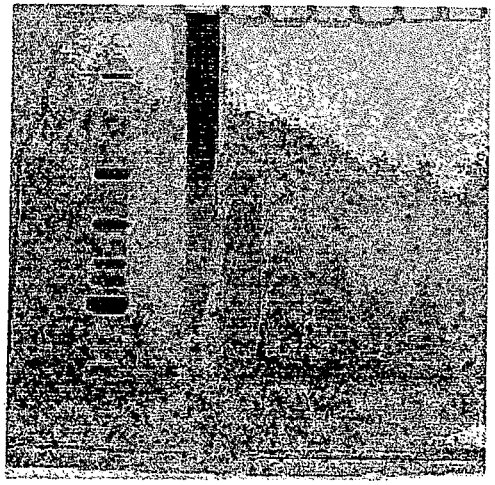
FIGS. 11A, 11B, 11C, and 11D set forth results showing the hydrolysis of commercially available gelatins performed at 150° C.
Figure 11B:
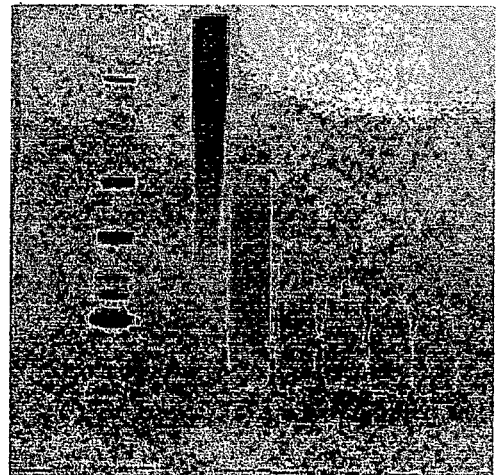
Figure 11C:
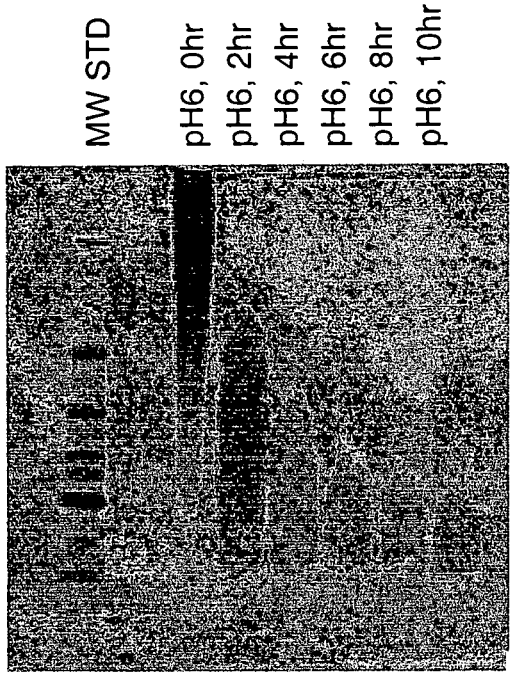
Figure 11D:
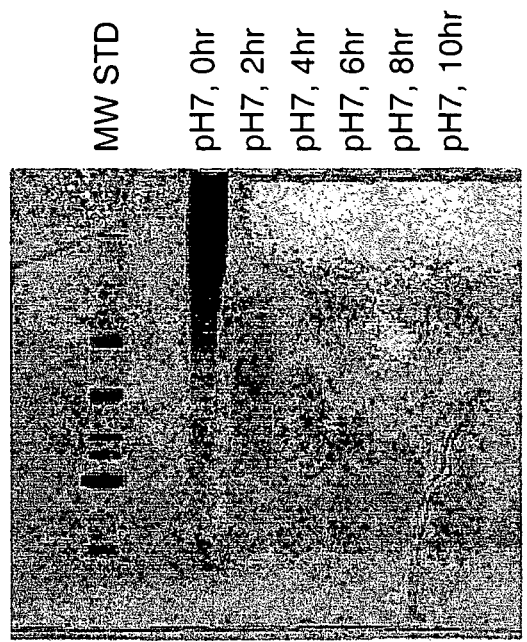

Molecular Weight Distribution of Commercially Available Gelatins:

These recombinant human gelatins were compared against commercially available gelatins. Four low molecular weight gelatin samples produced by Leiner Davis, Great Lake, Kind & Knox, and Dynagel, were obtained for characterization. All gelatins examined were soluble at room temperature. The molecular weight distributions of the gelatins on a Tricine SDS-PAGE gel are shown on FIG. 9 and listed in Table 4. The gel profiles indicated the molecular weight distributions of commercially available gelatins were approximately 0-55 kDa, with the exception of the Dynagel-1 sample, which had a molecular weight distribution of 0-30 kDa. The gel profiles also revealed two patterns of molecular weight distribution. In one example, derived from the samples from Leiner Davis and Great Lakes, several discrete molecular bands were observed by SDS-PAGE. The pattern in the second example, derived from the Dynagel and Kind & Knox samples, showed a continuous distribution of material on the gel, with no discrete banding. The molecular weight distributions of Dynagel-1 and Dynagel-2 were quite different, despite being produced by the same manufacturer for the same application. This result indicated that batch-to-batch variation could be quite significant in currently available gelatins.

TABLE 4

| Company | Relative Mobility | Maximum Apparent Molecular Weight (Da) | Molecular Weight* Distribution (Da) |
|---|---|---|---|
| K & K | 0.3410 | 70,000 | 0-55,500 |
| Leiner Davis | 0.3410 | 70,000 | 0-55,500 |
| Great Lake | 0.3693 | 60,000 | 0-47,600 |
| Sol-U-Por, #1 | 0.3483 | 65,000 | 0-51,600 |
| Sol-U-Por, #2 | 0.4972 | 37,000 | 0-29,400 |

*The molecular weight was adjusted by a factor of 1.26, which is the ratio of the mean residue weight of the standard proteins (115) over the mean residue weight of the collagenous proteins (91.6).

Heat hydrolysis of gelatins was performed as follows. The commercially available dry gelatins were dissolved in 40°-50° C. water to make a 5% gelatin solution. The pH of the solution was adjusted with either 0.1N NaOH or 0.1N HCl in preparation for heat hydrolysis. Both type I and type III recombinant human collagens were expressed in Pichia pastoris and purified, as described in U.S. Pat. No. 5,593,859. The final recombinant human collagen was dissolved in 10 mM HCl, dialyzed against water, and lyophilized. The lyophilized recombinant human collagen was dissolved in 40°-50° C. water to make a 3% solution. The pH of the solution was adjusted as indicated below prior to heat hydrolysis.

Heat hydrolysis was performed in 1 ml Reacti-Vials (Pierce). The hydrolysis temperature varied from 100° C. to 150° C., depending on the experiment. The pH of the hydrolysis solution varied from pH 2 to pH 7, as indicated. The hydrolysis time was also varied from one to thirty-two hours, depending on the temperature and pH of the solution. The gelatin hydrolysates were sampled at various time intervals and analyzed by SDS-PAGE.

Hydrolysis of Commercially Available Gelatins at 120° C.:

Samples of high molecular weight gelatin from Sigma (Type A from porcine skin, 250 kDa) were dissolved in six different pH solutions (5% gelatin) and hydrolyzed at 120° C. The pH 2 and pH 3 solutions were hydrolyzed for two and a half hours and sampled every half hour. The pH 4 solutions were hydrolyzed for five hours and sampled every hour. The pH 5, pH 6, and pH 7 solutions were hydrolyzed for 24 hours and sampled every two hours after 14 hours of hydrolysis.

The hydrolysis patterns were analyzed on Tricine 10-20% SDS-gels as shown in FIGS. 10A, 10B, 10C, 10D, 10E, and 10F. The gel profiles show that the lower the pH of the solution, the more quickly the hydrolysis of the gelatin occurred. The gel profiles also revealed two hydrolysis patterns among the hydrolysates. One pattern showed several discrete molecular bands on the gel (see the acid hydrolysis results of the pH 2 and pH 3 solutions, FIGS. 10A and 10B), while the other pattern showed a continuous distribution of material on the gel (see the hydrolysis results of the pH 4, pH 5, pH 6, and pH 7 solutions, FIGS. 10C, 10D, 10E, and 10F).

These results showed that the process outlined above, or variations thereof, produced two different types of material, as seen in the analysis of the commercially available gelatins (discrete bands vs. a continuous distribution of material on SDS-PAGE). These experimental results also indicated that heat degradation of high molecular weight gelatin generated various sizes of soluble gelatins. Table 5 shows the molecular weight distributions obtained using Sigma Gelatin, following hydrolysis at 120° C. in pH 6.0 solution.

TABLE 5

| Hydrolysis Time (hr) | Relative Mobility | Max. App. Mol. Weight (Da) | Molecular Weight Distribution (Da) |
| --- | --- | --- | --- |
| 4 | 0.2356 | 140,000 | 0-111,000 |
| 8 | 0.2890 | 90,000 | 0-71,400 |
| 11.5 | 0.3372 | 75,000 | 0-59,500 |
| 16 | 0.3837 | 47,000 | 0-37,300 |
| 20 | 0.4186 | 40,000 | 0-31,700 |
| 24 | 0.4525 | 33,000 | 0-26,200 |

Hydrolysis of Commercially Available Gelatins at 150° C.:

Samples of high molecular weight gelatin from Sigma (Type A from porcine skin, 250 kDa) were dissolved in four different pH solutions (5% gelatin) and hydrolyzed at 150° C. for up to ten hours. The hydrolysates were sampled every two hours for analysis. The hydrolysis patterns were analyzed by Tricine 10-20% SDS-PAGE gels as shown in FIGS. 11A, 11B, 11C, and 11D. The gel profiles indicated that the degradation of gelatin occurred much more rapidly at 150° C. than at 120° C. Additionally, hydrolysis of gelatins performed at 150° C. produced gelatin fragments of lower molecular weights. Table 6 shows the molecular weight distributions of Sigma Gelatin, following hydrolysis at 150° C. in pH 6.0 solution.

TABLE 6

| Hydrolysis Time (hr) | Relative Mobility | Max. App. Mol. Weight (Da) | Molecular Weight Distribution (Da) |
| --- | --- | --- | --- |
| 2.5 | 0.2833 | 95,000 | 0-75,400 |
| 4.5 | 0.4555 | 41,000 | 0-32,500 |
| 6 | 0.5277 | 32,000 | 0-25,400 |
| 8 | 0.5833 | 24,000 | 0-19,000 |
| 10 | 0.6611 | 15,000 | 0-11,900 |

Example 10

Acid and Thermal Hydrolysis of Recombinant Human Collagen I and III

Figure 12A:
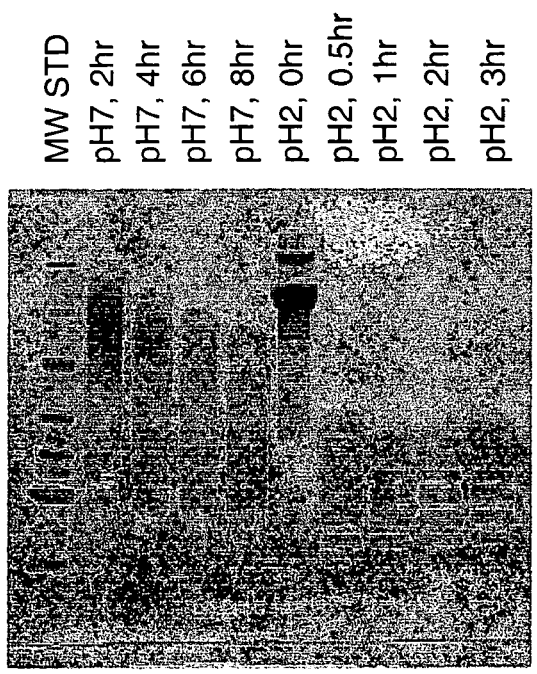
FIGS. 12A and 12B set forth results showing the acid and thermal hydrolysis of recombinant human collagen type I and type III.
Figure 12B:
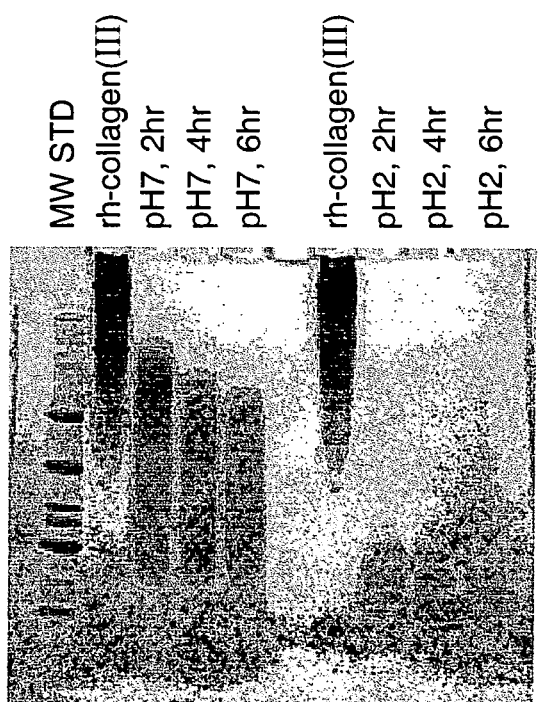

Recombinant human collagen type I was hydrolyzed at 120° C. for up to 8 hours under neutral pH conditions (pH 7), or up to 3 hours in acidic pH conditions (pH 2). Recombinant human collagen type III was also hydrolyzed at 120° C. for up to six hours in both neutral and acidic conditions. Hydrolysis was performed as described in Example 9. The human recombinant type I and type III hydrolysates were analyzed by Tricine 10-20% SDS-PAGE gels, shown in FIGS. 12A and 12B. The SDS-PAGE gel patterns indicated that the heat hydrolysis of recombinant human collagen was identical to the hydrolysis patterns of high molecular weight gelatins derived from natural sources. (FIG. 9, FIGS. 10A through 10F, and FIGS. 11A through 11D, to FIGS. 12A and 12B.) Similar to the hydrolysis of natural gelatins (pH 7), the acid hydrolysates of recombinant human collagen showed several discrete molecular weight bands, while the neutral hydrolysates showed a more continuous molecular weight distribution. The molecular weight distribution of the neutral hydrolysates of recombinant human gelatin was around 0-70 kDa after six to eight hours of heat degradation. The hydrolysis under acidic conditions occurred much faster. The molecular weight distributions of the acidic hydrolysates of recombinant human gelatin were much narrower, around 0-10 kDa, after two to three hours of heat treatment.

As a further refinement of the heat hydrolyzed recombinant human gelatins discussed, we have demonstrated the utility of a yeast multi-gene recombinant expression methodology for the production of human gelatins with discrete fragments of the α1(I) chain of human type I collagen. This technology allowed us to produce well-defined, highly homogeneous gelatin fragments ranging in size from 6-65 kDa. This presents unsurpassed flexibility in terms of the size and biophysical properties of the gelatin that can be used for specific applications.

Example 11

Enzymatic Hydrolysis of Recombinant Human Collagen Type I

Figure 13:
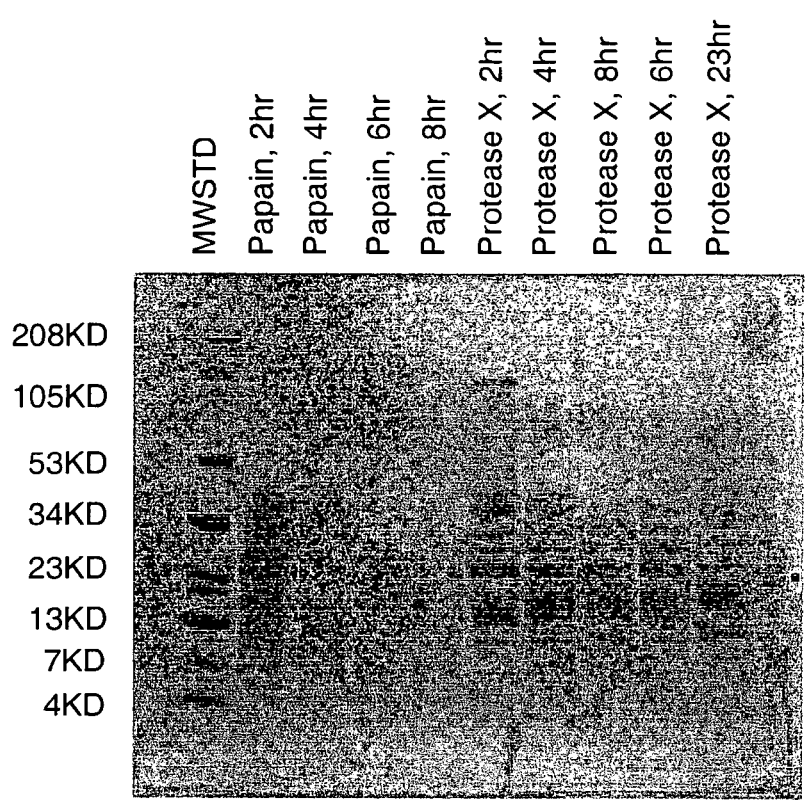
FIG. 13 sets forth results showing the enzymatic hydrolysis of recombinant human collagen type I.

Recombinant human collagen type I was hydrolyzed enzymatically, using the proteases set forth in Table 7. Recombinant human collagen type I was incubated with each enzyme at 37° C., using a substrate to enzyme ratio (w/w) as indicated in Table 7. The human recombinant type I hydrolysates obtained by treatment were analyzed by Tricine 10-20% SDS-PAGE gels. The results obtained from papain and protease X treatment are shown in FIG. 13. The SDS-PAGE gel patterns indicated that the enzymatic hydrolysis of recombinant human collagen lead to different molecular weight distributions of the gelatins. Enzymatic hydrolysis using papain resulted in a continuous hydrolysis pattern, as indicated in FIG. 13 and in Table 7, while hydrolysis using protease X resulted in several discrete molecular weight bands. As indicated in Table 7, the recombinant gelatins produced by this method had different hydrolysis patterns as a result of the particular enzymatic hydrolysis treatment. This presents great flexibility in producing sizes and biophysical properties of the gelatin that can be used for specific applications.

TABLE 7

| Enzyme | Enzyme Activity/mg Protein | Substrate to Enzyme Ratio | Hydrolysis Pattern |
|---|---|---|---|
| Chymo-papain | 1 U @ 37° C., pH 6.5 | 500:1 | Continuous |
| Bromelain | 8 U @ 37° C., pH 4.6 | 5,000:1 | Banding & Continuous |
| Protease VIII | 12 U @ 37° C., pH 8.5 | 7,000:1 | Banding |
| Papain | 17 U @ 37° C., pH 6.5 | 10,000:1 | Continuous |
| Protease X | 42 U @ 37° C., pH 8.5 | 20,000:1 | Banding |

Example 12

Antibodies to Recombinant Human Collagen Type I Directed Against Different Recombinant Gelatins Human recombinant type I collagen produced in the yeast *Pichia pastoris* was tested for its potential allergic reaction as a contact sensitizer on guinea pig, known as Maximization Study. After the duration of the study, the sera were collected to investigate the immunogenecity of recombinant human type I collagen in guinea pig. One gram of rhC I was immersed in 10 ml of either 0.9% Sodium Chloride Injection (SCI) or sesame oil, and incubated for 72 hours at 37° C. The extract was then centrifuge at 3000 rpm for 15 minutes and the supernatant collected for dosing.

Hartley pigs were exposed to the test article and control solution by an induction phase. This phase involved three pairs of intradermal (ID) injections on clipped areas. The first pair of ID injections (cranial) consisted of an emulsion of Freud's Complete Adjuvant (FCA) in an equal volume of SCI. The second pair of ID injections (middle) consisted of the test extract (recombinant human type I collagen). The third pair (caudal) consisted of an emulsion of the test extract article and equal volume of FCA. Positive and negative control animals were treated in a similar manner as the test animals, except that the test extract was not included in the second and third pair of injections.

On the sixth day after ID injections, the test sites were evaluated for evidence of irritation. The test sites were then pretreated with 10% SLS in petroleum and massaged into the skin using a glass rod, and then left uncovered for 24 hours. On the seventh day, a topical application was administered on the shaved areas of each test animals with 4.25 cm diameter disk of Whatman #3 filter paper soaked with 0.4 ml the test article extract. Thirteen days after the topical induction application, the animals were challenged. An area on the right side of each animal was clipped. On the next day, Hill Top chambers containing 0.3 ml of test extract, vehicle control extract, or positive control solutions were applied to clipped areas and remained on the animals for 24 hours. The dosing sites were scored for erythema and edema 24, 48, and 72 hours after removal of the chambers.

After 72 hours, the blood was collected and allowed to clot, then centrifuged at 2800 rpm for 15 minutes. The serum was removed from each tube and serum samples were stored at −70° C. until use.

Figure 14:
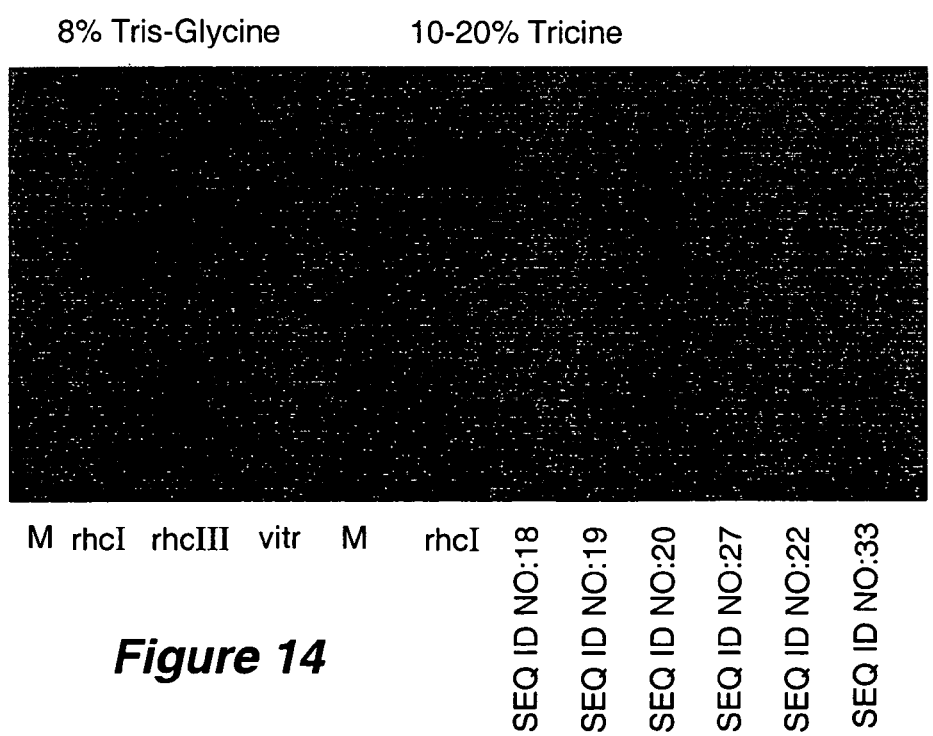
FIG. 14 sets forth a Western blot analysis of recombinant human collagens and recombinant human gelatins using antisera from Guinea pigs immunized with recombinant human collagen type I.

Sera from the immunized Guinea pigs were then analyzed for the presence of antibodies directed against recombinant human collagen type I (rhcI), recombinant human collagen type III (rhcIII), VITROGEN bovine collagen (Cohesion Technologies; Palo Alto, Calif.), and various fragments of recombinant human gelatins of the present invention, including 6 kDa (SEQ ID NO:18), 10 kDa (SEQ ID NO:19), 18 kDa (SEQ ID NO:20), 33 kDa (SEQ ID NO:27), 50 kDa (SEQ ID NO:22), and 65 kDa (SEQ ID NO:33) fragments. (See Table 2 and Example 1.) Recombinant collagen and recombinant gelatin were electrophoresed on 8% Tris-Glycine or 10-20% Tricine SDS-PAGE gels. Western blot analysis was performed using anti-serum from each of the Guinea pigs used in the study. FIG. 14 shows that recombinant human type I collagen-specific antibodies were present in the sera of Guinea pigs immunized with recombinant human type I collagen. No antibody reactivity to any of the recombinant gelatins analyzed by Western blot analysis was observed in any of the sera of examined. FIG. 14 shows Western blot results using the antisera from one Guinea pig in the study. The sera from at least 4 different Guinea pigs were analyzed, each of which showed identical results to that disclosed in FIG. 14.

Figure 15A:
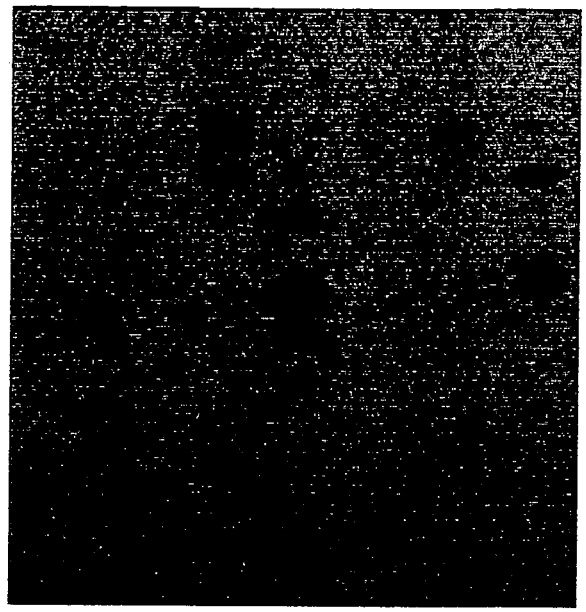
FIGS. 15A and 15B set forth results showing antisera from Guinea pigs immunized with recombinant human collagen type I is reactive to specific cyanogen bromide fragments of collagen type I.
Figure 15B:
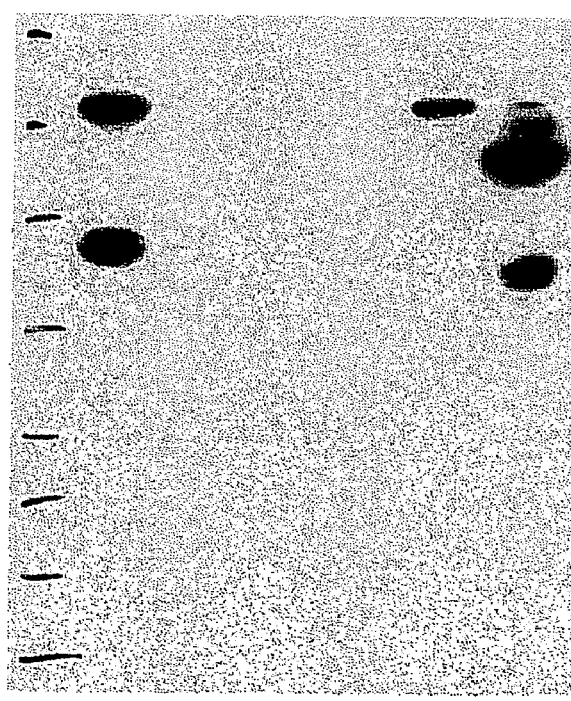

It was desirable to elucidate possible epitopes of the type I collagen responsible for the antigenic response observed following injection of rhcI into Guinea pigs. Recombinant human collagen type I was separated into its α1(I) and α2(I) components following denaturation and column chromatography. Cyanogen bromide (CNBr) cleavage of the α1(I) chain of recombinant type I collagen and the α2(I) chain of recombinant type I collagen was performed as described in Bornstein and Piez (1966) Biochemistry 5:3460. The intact a chains and the resulting peptide fragments were separated by SDS-PAGE and analyzed by Western blot analysis for reactivity to the Guinea pig sera described above. FIG. 15A shows a coomassie-stained SDS-PAGE of intact and CNBr-cleaved α1(I) and α2(I) chains of recombinant human type I collagen. Western blot analysis showed that the Guinea pig antisera reactive to rhcI were directed against the α2 chain of type I collagen and specific CNBr fragments thereof. No reactivity against the α1 chain of type I collagen was detected. (FIG. 15B.)

Figure 16:
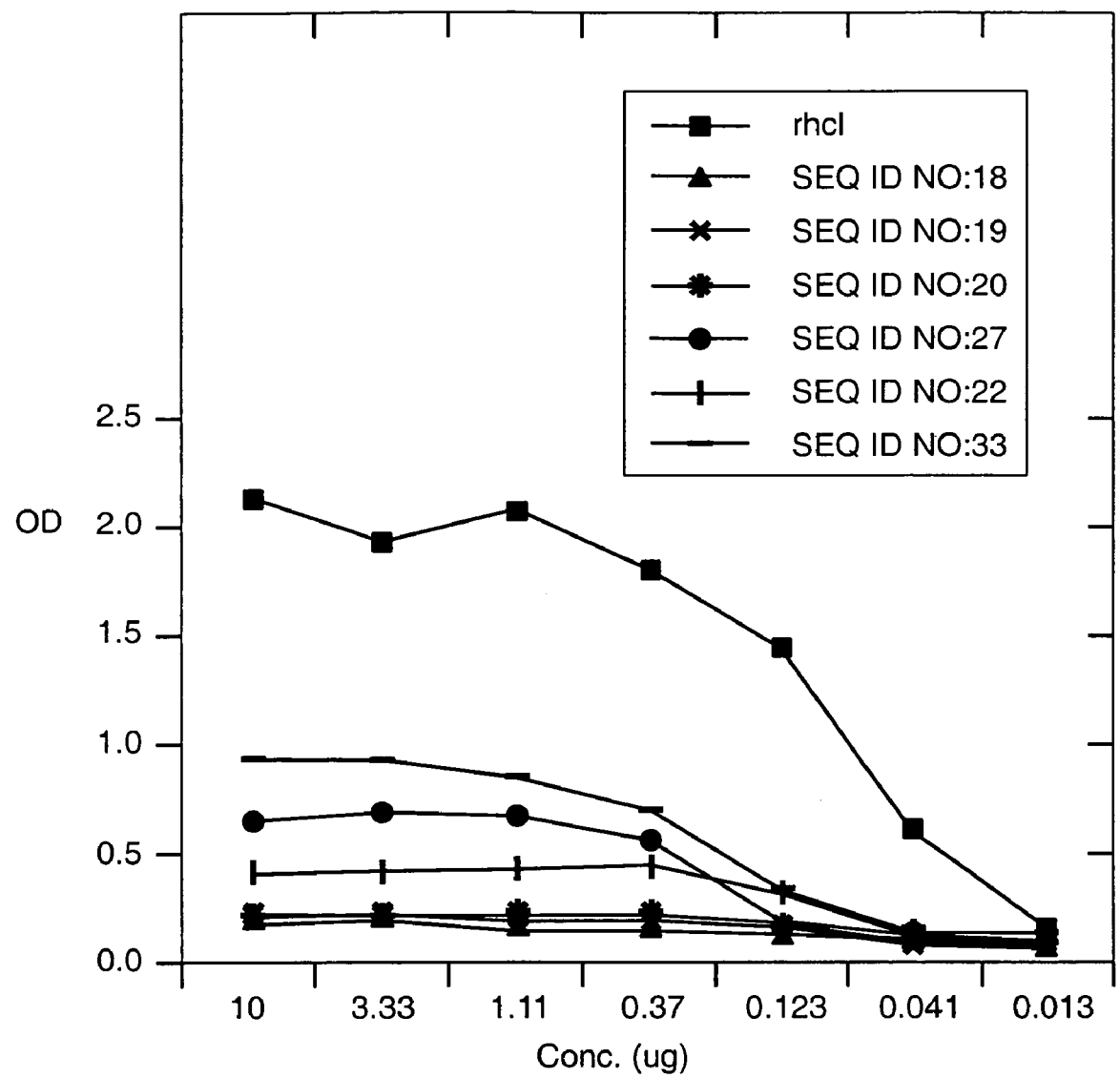
FIG. 16 sets forth ELISA results showing antisera from Guinea pigs immunized with recombinant human collagen type I is not reactive to recombinant human gelatins.

The Western blot analyses described above examined the reactivity of the Guinea pig sera to recombinant human type I collagen, CNBr fragments, and recombinant human gelatins by virtue of electrophoretic separation on SDS-PAGE. To examine the reactivity of the Guinea pig antisera to these polypeptides under non-denatured conditions, a direct ELISA analysis was performed. (FIG. 16.) The data showed that the Guinea pig antisera recognized the native conformation of rhcI. None of the recombinant gelatins of the present invention reacted with the Guinea pig antisera by ELISA, regardless of whether the gelatin fragments were presented before or after thermal denaturation. The rhcI was even more reactive in the ELISA if heat-denatured prior to analysis (data not shown). This indicated the polyclonal antibodies in the sera recognized primarily sequenced epitopes, rather than helical structures. Together, these results indicated that the concerns associated with having an antigenic site(s) present on human collagen type I, specifically to the α2 chain as shown in the current example, could be avoided by the methods of the present invention. The present invention thus provides methods for generating recombinant gelatins lacking antigenic sites, which would be useful for specific applications in which gelatin of low antigenicity is desired.

Various modifications and variations of the described methods and systems of the invention will be apparent to those skilled in the art without departing from the spirit and scope of the invention. Although the invention has been described in connection with specific preferred embodiments, it should be understood that the invention as claimed should not be unduly limited to such specific embodiments. Various modifications of the described modes for carrying out the invention which are obvious to those skilled in the present art and related fields are intended to be within the scope of the following claims. All references cited herein are incorporated by reference herein in their entirety.

What is claimed is:

1. A recombinant gelatin comprising the amino acid sequence of SEQ ID NO:30.
2. An encapsulant comprising the recombinant gelatin of claim 1.
3. A stabilizing agent comprising the recombinant gelatin of claim 1.
4. A film-forming agent comprising the recombinant gelatin of claim 1.
5. An emulsifier comprising the recombinant gelatin of claim 1.
6. A thickening agent comprising the recombinant gelatin of claim 1.
7. A colloidal agent comprising the recombinant gelatin of claim 1.
8. A hard gel capsule comprising the recombinant gelatin of claim 1.
9. A soft gel capsule comprising the recombinant gelatin of claim 1.
10. A plasma expander comprising the recombinant gelatin of claim 1.
11. A colloidal volume replacement material comprising the recombinant gelatin of claim 1.
12. A medical sponge comprising the recombinant gelatin of claim 1.
13. A pharmaceutical stabilizer comprising the recombinant gelatin of claim 1.
14. The pharmaceutical stabilizer of claim 13, wherein the pharmaceutical stabilizer is a vaccine stabilizer.
15. A microcarrier comprising the recombinant gelatin of claim 1.
16. An edible composition comprising the recombinant gelatin of claim 1.
17. A protein supplement comprising the recombinant gelatin of claim 1.
18. A fat substitute comprising the recombinant gelatin of claim 1.
19. A nutritional supplement comprising the recombinant gelatin of claim 1.
20. An edible coating comprising the recombinant gelatin of claim 1.
21. A photographic composition comprising the recombinant gelatin of claim 1.
22. A cosmetic composition comprising the recombinant gelatin of claim 1.
23. An industrial composition comprising the recombinant gelatin of claim 1.
24. A cell culture composition comprising the recombinant gelatin of claim 1.

* * * * *

SEQUENCE LISTING

<160> NUMBER OF SEQ ID NOS: 33

<210> SEQ ID NO 1
<211> LENGTH: 51
<212> TYPE: DNA
<213> ORGANISM: human

<400> SEQUENCE: 1
gtatctctcg agaagagaga ggctgaagct ggtctgcctg gtgccaaggg t            51

<210> SEQ ID NO 2
<211> LENGTH: 34
<212> TYPE: DNA
<213> ORGANISM: human

<400> SEQUENCE: 2
tagactatta tctctcgcca gcgggaccag cagg                              34

<210> SEQ ID NO 3
<211> LENGTH: 51
<212> TYPE: DNA
<213> ORGANISM: human

<400> SEQUENCE: 3
gtatctctcg agaagagaga ggctgaggct ggagctcagg gaccccctgg c            51

<210> SEQ ID NO 4
<211> LENGTH: 40
<212> TYPE: DNA
<213> ORGANISM: human

<400> SEQUENCE: 4
atgctctaga ttattacttg tcaccagggg caccagcagg                        40

<210> SEQ ID NO 5
<211> LENGTH: 54
<212> TYPE: DNA
<213> ORGANISM: human

<400> SEQUENCE: 5
gtatctctcg agaagagaga ggctgaagct ggccccatgg gtccctctgg tcct         54

<210> SEQ ID NO 6
<211> LENGTH: 39
<212> TYPE: DNA
<213> ORGANISM: human

<400> SEQUENCE: 6
tgctctagat cattaagcat ctcccttggc accatccaa                         39

<210> SEQ ID NO 7
<211> LENGTH: 45
<212> TYPE: DNA
<213> ORGANISM: human

<400> SEQUENCE: 7
tgctctagac tattaaggcg cgccagcatc acccttagca ccatc         45

<210> SEQ ID NO 8
<211> LENGTH: 48
<212> TYPE: DNA
<213> ORGANISM: human

<400> SEQUENCE: 8
tgctctagat cattaaggcg cgccaggttc accgctgtta cccttggg      48

<210> SEQ ID NO 9
<211> LENGTH: 39
<212> TYPE: DNA
<213> ORGANISM: human

<400> SEQUENCE: 9
tgctctagat cattatctct cgcctcttgc tccagaggg                39

<210> SEQ ID NO 10
<211> LENGTH: 57
<212> TYPE: DNA
<213> ORGANISM: human

<400> SEQUENCE: 10
gtgcccgtgg tcaggctggt gtgatgggat tccctggacc taaaggtgct gcttaat    57

<210> SEQ ID NO 11
<211> LENGTH: 64
<212> TYPE: DNA
<213> ORGANISM: human

<400> SEQUENCE: 11
ctagattaag cagcacctt aggtccaggg aatcccatca caccagcctg accacgggca  60
ccag                                                              64

<210> SEQ ID NO 12
<211> LENGTH: 40
<212> TYPE: DNA
<213> ORGANISM: human

<400> SEQUENCE: 12
atgctctaga ttattaagga gaaccgtctc gtccagggga              40

<210> SEQ ID NO 13
<211> LENGTH: 37
<212> TYPE: DNA
<213> ORGANISM: human

<400> SEQUENCE: 13
ctagtctaga ttatcttgct ccagaggggc caggggc                 37

<210> SEQ ID NO 14
<211> LENGTH: 37
<212> TYPE: DNA
<213> ORGANISM: human

<400> SEQUENCE: 14
ctagtctaga ttagcgagca cctttggctc caggagc                 37

<210> SEQ ID NO 15

<211> LENGTH: 102
<212> TYPE: PRT
<213> ORGANISM: human

<400> SEQUENCE: 15

Gly Pro Met Gly Pro Ser Gly Pro Arg Gly Leu Pro Gly Pro Pro Gly
1               5                   10                  15

Ala Pro Gly Pro Gln Gly Phe Gln Gly Pro Gly Glu Pro Gly Glu
            20                  25                  30

Pro Gly Ala Ser Gly Pro Met Gly Pro Arg Gly Pro Pro Gly Pro Pro
        35                  40                  45

Gly Lys Asn Gly Asp Asp Gly Glu Ala Gly Lys Pro Gly Arg Pro Gly
50                  55                  60

Glu Arg Gly Pro Pro Gly Pro Gln Gly Ala Arg Gly Leu Pro Gly Thr
65                  70                  75                  80

Ala Gly Leu Pro Gly Met Lys Gly His Arg Gly Phe Ser Gly Leu Asp
                85                  90                  95

Gly Ala Lys Gly Asp Ala
            100

<210> SEQ ID NO 16
<211> LENGTH: 261
<212> TYPE: PRT
<213> ORGANISM: human

<400> SEQUENCE: 16

Gly Pro Met Gly Pro Ser Gly Pro Arg Gly Leu Pro Gly Pro Pro Gly
1               5                   10                  15

Ala Pro Gly Pro Gln Gly Phe Gln Gly Pro Gly Glu Pro Gly Glu
            20                  25                  30

Pro Gly Ala Ser Gly Pro Met Gly Pro Arg Gly Pro Pro Gly Pro Pro
        35                  40                  45

Gly Lys Asn Gly Asp Asp Gly Glu Ala Gly Lys Pro Gly Arg Pro Gly
50                  55                  60

Glu Arg Gly Pro Pro Gly Pro Gln Gly Ala Arg Gly Leu Pro Gly Thr
65                  70                  75                  80

Ala Gly Leu Pro Gly Met Lys Gly His Arg Gly Phe Ser Gly Leu Asp
                85                  90                  95

Gly Ala Lys Gly Asp Ala Gly Pro Ala Gly Pro Lys Gly Glu Pro Gly
            100                 105                 110

Ser Pro Gly Glu Asn Gly Ala Pro Gly Gln Met Gly Pro Arg Gly Leu
        115                 120                 125

Pro Gly Glu Arg Gly Arg Pro Gly Ala Pro Gly Pro Ala Gly Ala Arg
130                 135                 140

Gly Asn Asp Gly Ala Thr Gly Ala Ala Gly Pro Pro Gly Pro Thr Gly
145                 150                 155                 160

Pro Ala Gly Pro Pro Gly Phe Pro Gly Ala Val Gly Ala Lys Gly Glu
                165                 170                 175

Ala Gly Pro Gln Gly Pro Arg Gly Ser Glu Gly Pro Gln Gly Val Arg
            180                 185                 190

Gly Glu Pro Gly Pro Pro Gly Pro Ala Gly Ala Ala Gly Pro Ala Gly
        195                 200                 205

Asn Pro Gly Ala Asp Gly Gln Pro Gly Ala Lys Gly Ala Asn Gly Ala
210                 215                 220

Pro Gly Ile Ala Gly Ala Pro Gly Phe Pro Gly Ala Arg Gly Pro Ser
225                 230                 235                 240

Gly Pro Gln Gly Pro Gly Gly Pro Pro Gly Pro Lys Gly Asn Ser Gly
            245                 250                 255

Glu Pro Gly Ala Pro
            260

<210> SEQ ID NO 17
<211> LENGTH: 501
<212> TYPE: PRT
<213> ORGANISM: human

<400> SEQUENCE: 17

Gly Pro Met Gly Pro Ser Gly Pro Arg Gly Leu Pro Gly Pro Pro Gly
 1               5                  10                  15

Ala Pro Gly Pro Gln Gly Phe Gln Gly Pro Pro Gly Glu Pro Gly Glu
            20                  25                  30

Pro Gly Ala Ser Gly Pro Met Gly Pro Arg Gly Pro Pro Gly Pro Pro
        35                  40                  45

Gly Lys Asn Gly Asp Asp Gly Glu Ala Gly Lys Pro Gly Arg Pro Gly
    50                  55                  60

Glu Arg Gly Pro Pro Gly Pro Gln Gly Ala Arg Gly Leu Pro Gly Thr
65                  70                  75                  80

Ala Gly Leu Pro Gly Met Lys Gly His Arg Gly Phe Ser Gly Leu Asp
                85                  90                  95

Gly Ala Lys Gly Asp Ala Gly Pro Ala Gly Pro Lys Gly Glu Pro Gly
            100                 105                 110

Ser Pro Gly Glu Asn Gly Ala Pro Gly Gln Met Gly Pro Arg Gly Leu
        115                 120                 125

Pro Gly Glu Arg Gly Arg Pro Gly Ala Pro Gly Pro Ala Gly Ala Arg
    130                 135                 140

Gly Asn Asp Gly Ala Thr Gly Ala Ala Gly Pro Pro Gly Pro Thr Gly
145                 150                 155                 160

Pro Ala Gly Pro Pro Gly Phe Pro Gly Ala Val Gly Ala Lys Gly Glu
                165                 170                 175

Ala Gly Pro Gln Gly Pro Arg Gly Ser Glu Gly Pro Gln Gly Val Arg
            180                 185                 190

Gly Glu Pro Gly Pro Pro Gly Pro Ala Gly Ala Ala Gly Pro Ala Gly
        195                 200                 205

Asn Pro Gly Ala Asp Gly Gln Pro Gly Ala Lys Gly Ala Asn Gly Ala
    210                 215                 220

Pro Gly Ile Ala Gly Ala Pro Gly Phe Pro Gly Ala Arg Gly Pro Ser
225                 230                 235                 240

Gly Pro Gln Gly Pro Gly Gly Pro Pro Gly Pro Lys Gly Asn Ser Gly
                245                 250                 255

Glu Pro Gly Ala Pro Gly Ser Lys Gly Asp Thr Gly Ala Lys Gly Glu
            260                 265                 270

Pro Gly Pro Val Gly Val Gln Gly Pro Pro Gly Pro Ala Gly Glu Glu
        275                 280                 285

Gly Lys Arg Gly Ala Arg Gly Glu Pro Gly Pro Thr Gly Leu Pro Gly
    290                 295                 300

Pro Pro Gly Glu Arg Gly Gly Pro Gly Ser Arg Gly Phe Pro Gly Ala
305                 310                 315                 320

Asp Gly Val Ala Gly Pro Lys Gly Pro Ala Gly Glu Arg Gly Ser Pro
                325                 330                 335

Gly Pro Ala Gly Pro Lys Gly Ser Pro Gly Glu Ala Gly Arg Pro Gly

```
                340                 345                 350
Glu Ala Gly Leu Pro Gly Ala Lys Gly Leu Thr Gly Ser Pro Gly Ser
            355                 360                 365
Pro Gly Pro Asp Gly Lys Thr Gly Pro Pro Gly Pro Ala Gly Gln Asp
        370                 375                 380
Gly Arg Pro Gly Pro Pro Gly Pro Gly Ala Arg Gly Gln Ala Gly
385                 390                 395                 400
Val Met Gly Phe Pro Gly Pro Lys Gly Ala Ala Gly Glu Pro Gly Lys
                405                 410                 415
Ala Gly Glu Arg Gly Val Pro Gly Pro Pro Gly Ala Val Gly Pro Ala
            420                 425                 430
Gly Lys Asp Gly Glu Ala Gly Ala Gln Gly Pro Pro Gly Pro Ala Gly
        435                 440                 445
Pro Ala Gly Glu Arg Gly Glu Gln Gly Pro Ala Gly Ser Pro Gly Phe
    450                 455                 460
Gln Gly Leu Pro Gly Pro Ala Gly Pro Pro Gly Glu Ala Gly Lys Pro
465                 470                 475                 480
Gly Glu Gln Gly Val Pro Gly Asp Leu Gly Ala Pro Gly Pro Ser Gly
                485                 490                 495
Ala Arg Gly Glu Arg
            500

<210> SEQ ID NO 18
<211> LENGTH: 59
<212> TYPE: PRT
<213> ORGANISM: human

<400> SEQUENCE: 18

Glu Ala Gly Leu Pro Gly Ala Lys Gly Leu Thr Gly Ser Pro Gly Ser
 1               5                  10                  15
Pro Gly Pro Asp Gly Lys Thr Gly Pro Pro Gly Pro Ala Gly Gln Asp
            20                  25                  30
Gly Arg Pro Gly Pro Pro Gly Pro Gly Ala Arg Gly Gln Ala Gly
        35                  40                  45
Val Met Gly Phe Pro Gly Pro Lys Gly Ala Ala
    50                  55

<210> SEQ ID NO 19
<211> LENGTH: 101
<212> TYPE: PRT
<213> ORGANISM: human

<400> SEQUENCE: 19

Glu Ala Gly Leu Pro Gly Ala Lys Gly Leu Thr Gly Ser Pro Gly Ser
 1               5                  10                  15
Pro Gly Pro Asp Gly Lys Thr Gly Pro Pro Gly Pro Ala Gly Gln Asp
            20                  25                  30
Gly Arg Pro Gly Pro Pro Gly Pro Gly Ala Arg Gly Gln Ala Gly
        35                  40                  45
Val Met Gly Phe Pro Gly Pro Lys Gly Ala Ala Gly Glu Pro Gly Lys
    50                  55                  60
Ala Gly Glu Arg Gly Val Pro Gly Pro Pro Gly Ala Val Gly Pro Ala
65                  70                  75                  80
Gly Lys Asp Gly Glu Ala Gly Ala Gln Gly Pro Pro Gly Pro Ala Gly
                85                  90                  95
Pro Ala Gly Glu Arg
```

```
<210> SEQ ID NO 20
<211> LENGTH: 185
<212> TYPE: PRT
<213> ORGANISM: human

<400> SEQUENCE: 20

Glu Ala Gly Leu Pro Gly Ala Lys Gly Leu Thr Gly Ser Pro Gly Ser
 1               5                  10                  15

Pro Gly Pro Asp Gly Lys Thr Gly Pro Pro Gly Pro Ala Gly Gln Asp
                20                  25                  30

Gly Arg Pro Gly Pro Pro Gly Pro Pro Gly Ala Arg Gly Gln Ala Gly
            35                  40                  45

Val Met Gly Phe Pro Gly Pro Lys Gly Ala Ala Gly Glu Pro Gly Lys
 50                  55                  60

Ala Gly Glu Arg Gly Val Pro Gly Pro Pro Gly Ala Val Gly Pro Ala
 65                  70                  75                  80

Gly Lys Asp Gly Glu Ala Gly Ala Gln Gly Pro Pro Gly Pro Ala Gly
                85                  90                  95

Pro Ala Gly Glu Arg Gly Glu Gln Gly Pro Ala Gly Ser Pro Gly Phe
                100                 105                 110

Gln Gly Leu Pro Gly Pro Ala Gly Pro Pro Gly Glu Ala Gly Lys Pro
            115                 120                 125

Gly Glu Gln Gly Val Pro Gly Asp Leu Gly Ala Pro Gly Pro Ser Gly
        130                 135                 140

Ala Arg Gly Glu Arg Gly Phe Pro Gly Glu Arg Gly Val Gln Gly Pro
145                 150                 155                 160

Pro Gly Pro Ala Gly Pro Arg Gly Ala Asn Gly Ala Pro Gly Asn Asp
                165                 170                 175

Gly Ala Lys Gly Asp Ala Gly Ala Pro
            180                 185

<210> SEQ ID NO 21
<211> LENGTH: 251
<212> TYPE: PRT
<213> ORGANISM: human

<400> SEQUENCE: 21

Glu Ala Gly Leu Pro Gly Ala Lys Gly Leu Thr Gly Ser Pro Gly Ser
 1               5                  10                  15

Pro Gly Pro Asp Gly Lys Thr Gly Pro Pro Gly Pro Ala Gly Gln Asp
                20                  25                  30

Gly Arg Pro Gly Pro Pro Gly Pro Pro Gly Ala Arg Gly Gln Ala Gly
            35                  40                  45

Val Met Gly Phe Pro Gly Pro Lys Gly Ala Ala Gly Glu Pro Gly Lys
 50                  55                  60

Ala Gly Glu Arg Gly Val Pro Gly Pro Pro Gly Ala Val Gly Pro Ala
 65                  70                  75                  80

Gly Lys Asp Gly Glu Ala Gly Ala Gln Gly Pro Pro Gly Pro Ala Gly
                85                  90                  95

Pro Ala Gly Glu Arg Gly Glu Gln Gly Pro Ala Gly Ser Pro Gly Phe
                100                 105                 110

Gln Gly Leu Pro Gly Pro Ala Gly Pro Pro Gly Glu Ala Gly Lys Pro
            115                 120                 125

Gly Glu Gln Gly Val Pro Gly Asp Leu Gly Ala Pro Gly Pro Ser Gly
```

```
                130                 135                 140
Ala Arg Gly Glu Arg Gly Phe Pro Gly Glu Arg Gly Val Gln Gly Pro
145                 150                 155                 160

Pro Gly Pro Ala Gly Pro Arg Gly Ala Asn Gly Ala Pro Gly Asn Asp
                165                 170                 175

Gly Ala Lys Gly Asp Ala Gly Ala Pro Gly Ala Pro Gly Ser Gln Gly
            180                 185                 190

Ala Pro Gly Leu Gln Gly Met Pro Gly Glu Arg Gly Ala Ala Gly Leu
        195                 200                 205

Pro Gly Pro Lys Gly Asp Arg Gly Asp Ala Gly Pro Lys Gly Ala Asp
210                 215                 220

Gly Ser Pro Gly Lys Asp Gly Val Arg Gly Leu Thr Gly Pro Ile Gly
225                 230                 235                 240

Pro Pro Gly Pro Ala Gly Ala Pro Gly Asp Lys
                245                 250

<210> SEQ ID NO 22
<211> LENGTH: 500
<212> TYPE: PRT
<213> ORGANISM: human

<400> SEQUENCE: 22

Glu Ala Gly Leu Pro Gly Ala Lys Gly Leu Thr Gly Ser Pro Gly Ser
1               5                   10                  15

Pro Gly Pro Asp Gly Lys Thr Gly Pro Pro Gly Pro Ala Gly Gln Asp
            20                  25                  30

Gly Arg Pro Gly Pro Pro Gly Pro Pro Gly Ala Arg Gly Gln Ala Gly
        35                  40                  45

Val Met Gly Phe Pro Gly Pro Lys Gly Ala Ala Gly Glu Pro Gly Lys
    50                  55                  60

Ala Gly Glu Arg Gly Val Pro Gly Pro Pro Gly Ala Val Gly Pro Ala
65                  70                  75                  80

Gly Lys Asp Gly Glu Ala Gly Ala Gln Gly Pro Pro Gly Pro Ala Gly
                85                  90                  95

Pro Ala Gly Glu Arg Gly Glu Gln Gly Pro Ala Gly Ser Pro Gly Phe
            100                 105                 110

Gln Gly Leu Pro Gly Pro Ala Gly Pro Pro Gly Glu Ala Gly Lys Pro
        115                 120                 125

Gly Glu Gln Gly Val Pro Gly Asp Leu Gly Ala Pro Gly Pro Ser Gly
    130                 135                 140

Ala Arg Gly Glu Arg Gly Phe Pro Gly Glu Arg Gly Val Gln Gly Pro
145                 150                 155                 160

Pro Gly Pro Ala Gly Pro Arg Gly Ala Asn Gly Ala Pro Gly Asn Asp
                165                 170                 175

Gly Ala Lys Gly Asp Ala Gly Ala Pro Gly Ala Pro Gly Ser Gln Gly
            180                 185                 190

Ala Pro Gly Leu Gln Gly Met Pro Gly Glu Arg Gly Ala Ala Gly Leu
        195                 200                 205

Pro Gly Pro Lys Gly Asp Arg Gly Asp Ala Gly Pro Lys Gly Ala Asp
    210                 215                 220

Gly Ser Pro Gly Lys Asp Gly Val Arg Gly Leu Thr Gly Pro Ile Gly
225                 230                 235                 240

Pro Pro Gly Pro Ala Gly Ala Pro Gly Asp Lys Gly Glu Ser Gly Pro
                245                 250                 255
```

-continued

```
Ser Gly Pro Ala Gly Pro Thr Gly Ala Arg Gly Ala Pro Gly Asp Arg
            260                 265                 270

Gly Glu Pro Gly Pro Gly Pro Ala Gly Phe Ala Gly Pro Pro Gly
        275                 280                 285

Ala Asp Gly Gln Pro Gly Ala Lys Gly Glu Pro Gly Asp Ala Gly Ala
            290                 295                 300

Lys Gly Asp Ala Gly Pro Pro Gly Pro Ala Gly Pro Ala Gly Pro Pro
305                 310                 315                 320

Gly Pro Ile Gly Asn Val Gly Ala Pro Gly Ala Lys Gly Ala Arg Gly
                325                 330                 335

Ser Ala Gly Pro Pro Gly Ala Thr Gly Phe Pro Gly Ala Ala Gly Arg
            340                 345                 350

Val Gly Pro Pro Gly Pro Ser Gly Asn Ala Gly Pro Pro Gly Pro Pro
            355                 360                 365

Gly Pro Ala Gly Lys Glu Gly Gly Lys Gly Pro Arg Gly Glu Thr Gly
            370                 375                 380

Pro Ala Gly Arg Pro Gly Glu Val Gly Pro Pro Gly Pro Pro Gly Pro
385                 390                 395                 400

Ala Gly Glu Lys Gly Ser Pro Gly Ala Asp Gly Pro Ala Gly Ala Pro
                405                 410                 415

Gly Thr Pro Gly Pro Gln Gly Ile Ala Gly Gln Arg Gly Val Val Gly
            420                 425                 430

Leu Pro Gly Gln Arg Gly Glu Arg Gly Phe Pro Gly Leu Pro Gly Pro
            435                 440                 445

Ser Gly Glu Pro Gly Lys Gln Gly Pro Ser Gly Ala Ser Gly Glu Arg
            450                 455                 460

Gly Pro Pro Gly Pro Met Gly Pro Pro Gly Leu Ala Gly Pro Pro Gly
465                 470                 475                 480

Glu Ser Gly Arg Glu Gly Ala Pro Ala Ala Glu Gly Ser Pro Gly Arg
                485                 490                 495

Asp Gly Ser Pro
            500

<210> SEQ ID NO 23
<211> LENGTH: 91
<212> TYPE: PRT
<213> ORGANISM: human

<400> SEQUENCE: 23

Glu Ala Gly Ala Gln Gly Pro Pro Gly Pro Ala Gly Pro Ala Gly Glu
  1               5                  10                  15

Arg Gly Glu Gln Gly Pro Ala Gly Ser Pro Gly Phe Gln Gly Leu Pro
             20                  25                  30

Gly Pro Ala Gly Pro Pro Gly Glu Ala Gly Lys Pro Gly Glu Gln Gly
         35                  40                  45

Val Pro Gly Asp Leu Gly Ala Pro Gly Pro Ser Gly Ala Arg Gly Glu
     50                  55                  60

Arg Gly Phe Pro Gly Glu Arg Gly Val Gln Gly Pro Pro Gly Pro Ala
 65                  70                  75                  80

Gly Pro Arg Gly Ala Asn Gly Ala Pro Gly Asn
                 85                  90

<210> SEQ ID NO 24
<211> LENGTH: 167
<212> TYPE: PRT
<213> ORGANISM: human
```

```
<400> SEQUENCE: 24

Glu Ala Gly Ala Gln Gly Pro Pro Gly Pro Ala Gly Pro Ala Gly Glu
 1               5                  10                  15

Arg Gly Glu Gln Gly Pro Ala Gly Ser Pro Gly Phe Gln Gly Leu Pro
            20                  25                  30

Gly Pro Ala Gly Pro Pro Gly Glu Ala Gly Lys Pro Gly Glu Gln Gly
        35                  40                  45

Val Pro Gly Asp Leu Gly Ala Pro Gly Pro Ser Gly Ala Arg Gly Glu
    50                  55                  60

Arg Gly Phe Pro Gly Glu Arg Gly Val Gln Gly Pro Pro Gly Pro Ala
 65                  70                  75                  80

Gly Pro Arg Gly Ala Asn Gly Ala Pro Gly Asn Asp Gly Ala Lys Gly
                85                  90                  95

Asp Ala Gly Ala Pro Gly Ala Pro Gly Ser Gln Gly Ala Pro Gly Leu
            100                 105                 110

Gln Gly Met Pro Gly Glu Arg Gly Ala Ala Gly Leu Pro Gly Pro Lys
        115                 120                 125

Gly Asp Arg Gly Asp Ala Gly Pro Lys Gly Ala Asp Gly Ser Pro Gly
    130                 135                 140

Lys Asp Gly Val Arg Gly Leu Thr Gly Pro Ile Gly Pro Pro Gly Pro
145                 150                 155                 160

Ala Gly Ala Pro Gly Asp Lys
                165

<210> SEQ ID NO 25
<211> LENGTH: 416
<212> TYPE: PRT
<213> ORGANISM: human

<400> SEQUENCE: 25

Glu Ala Gly Ala Gln Gly Pro Pro Gly Pro Ala Gly Pro Ala Gly Glu
 1               5                  10                  15

Arg Gly Glu Gln Gly Pro Ala Gly Ser Pro Gly Phe Gln Gly Leu Pro
            20                  25                  30

Gly Pro Ala Gly Pro Pro Gly Glu Ala Gly Lys Pro Gly Glu Gln Gly
        35                  40                  45

Val Pro Gly Asp Leu Gly Ala Pro Gly Pro Ser Gly Ala Arg Gly Glu
    50                  55                  60

Arg Gly Phe Pro Gly Glu Arg Gly Val Gln Gly Pro Pro Gly Pro Ala
 65                  70                  75                  80

Gly Pro Arg Gly Ala Asn Gly Ala Pro Gly Asn Asp Gly Ala Lys Gly
                85                  90                  95

Asp Ala Gly Ala Pro Gly Ala Pro Gly Ser Gln Gly Ala Pro Gly Leu
            100                 105                 110

Gln Gly Met Pro Gly Glu Arg Gly Ala Ala Gly Leu Pro Gly Pro Lys
        115                 120                 125

Gly Asp Arg Gly Asp Ala Gly Pro Lys Gly Ala Asp Gly Ser Pro Gly
    130                 135                 140

Lys Asp Gly Val Arg Gly Leu Thr Gly Pro Ile Gly Pro Pro Gly Pro
145                 150                 155                 160

Ala Gly Ala Pro Gly Asp Lys Gly Glu Ser Gly Pro Ser Gly Pro Ala
                165                 170                 175

Gly Pro Thr Gly Ala Arg Gly Ala Pro Gly Asp Arg Gly Glu Pro Gly
            180                 185                 190
```

-continued

Pro Pro Gly Pro Ala Gly Phe Ala Gly Pro Gly Ala Asp Gly Gln
            195                 200                 205

Pro Gly Ala Lys Gly Glu Pro Gly Asp Ala Gly Ala Lys Gly Asp Ala
210                 215                 220

Gly Pro Pro Gly Pro Ala Gly Pro Ala Gly Pro Pro Gly Pro Ile Gly
225                 230                 235                 240

Asn Val Gly Ala Pro Gly Ala Lys Gly Ala Arg Gly Ser Ala Gly Pro
            245                 250                 255

Pro Gly Ala Thr Gly Phe Pro Gly Ala Ala Gly Arg Val Gly Pro Pro
            260                 265                 270

Gly Pro Ser Gly Asn Ala Gly Pro Pro Gly Pro Pro Gly Pro Ala Gly
            275                 280                 285

Lys Glu Gly Gly Lys Gly Pro Arg Gly Glu Thr Gly Pro Ala Gly Arg
            290                 295                 300

Pro Gly Glu Val Gly Pro Pro Gly Pro Pro Gly Pro Ala Gly Glu Lys
305                 310                 315                 320

Gly Ser Pro Gly Ala Asp Gly Pro Ala Gly Ala Pro Gly Thr Pro Gly
            325                 330                 335

Pro Gln Gly Ile Ala Gly Gln Arg Gly Val Val Gly Leu Pro Gly Gln
            340                 345                 350

Arg Gly Glu Arg Gly Phe Pro Gly Leu Pro Gly Pro Ser Gly Glu Pro
            355                 360                 365

Gly Lys Gln Gly Pro Ser Gly Ala Ser Gly Glu Arg Gly Pro Pro Gly
            370                 375                 380

Pro Met Gly Pro Pro Gly Leu Ala Gly Pro Pro Gly Glu Ser Gly Arg
385                 390                 395                 400

Glu Gly Ala Pro Ala Ala Glu Gly Ser Pro Gly Arg Asp Gly Ser Pro
            405                 410                 415

<210> SEQ ID NO 26
<211> LENGTH: 510
<212> TYPE: PRT
<213> ORGANISM: human

<400> SEQUENCE: 26

Gly Glu Arg Gly Val Gln Gly Pro Pro Gly Pro Ala Gly Pro Arg Gly
1               5                   10                  15

Ala Asn Gly Ala Pro Gly Asn Asp Gly Ala Lys Gly Asp Ala Gly Ala
                20                  25                  30

Pro Gly Ala Pro Gly Ser Gln Gly Ala Pro Gly Leu Gln Gly Met Pro
            35                  40                  45

Gly Glu Arg Gly Ala Ala Gly Leu Pro Gly Pro Lys Gly Asp Arg Gly
        50                  55                  60

Asp Ala Gly Pro Lys Gly Ala Asp Gly Ser Pro Gly Lys Asp Gly Val
65                  70                  75                  80

Arg Gly Leu Thr Gly Pro Ile Gly Pro Pro Gly Pro Ala Gly Ala Pro
                85                  90                  95

Gly Asp Lys Gly Glu Ser Gly Pro Ser Gly Pro Ala Gly Pro Thr Gly
            100                 105                 110

Ala Arg Gly Ala Pro Gly Asp Arg Gly Glu Pro Gly Pro Pro Gly Pro
        115                 120                 125

Ala Gly Phe Ala Gly Pro Pro Gly Ala Asp Gly Gln Pro Gly Ala Lys
    130                 135                 140

Gly Glu Pro Gly Asp Ala Gly Ala Lys Gly Asp Ala Gly Pro Pro Gly

```
                145                 150                 155                 160
Pro Ala Gly Pro Ala Gly Pro Gly Pro Ile Gly Asn Val Gly Ala
                165                 170                 175
Pro Gly Ala Lys Gly Ala Arg Gly Ser Ala Gly Pro Pro Gly Ala Thr
                180                 185                 190
Gly Phe Pro Gly Ala Ala Gly Arg Val Gly Pro Pro Gly Pro Ser Gly
                195                 200                 205
Asn Ala Gly Pro Pro Gly Pro Pro Gly Pro Ala Gly Lys Glu Gly Gly
                210                 215                 220
Lys Gly Pro Arg Gly Glu Thr Gly Pro Ala Gly Arg Pro Gly Glu Val
225                 230                 235                 240
Gly Pro Pro Gly Pro Pro Gly Pro Ala Gly Glu Lys Gly Ser Pro Gly
                245                 250                 255
Ala Asp Gly Pro Ala Gly Ala Pro Gly Thr Pro Gly Pro Gln Gly Ile
                260                 265                 270
Ala Gly Gln Arg Gly Val Val Gly Leu Pro Gly Gln Arg Gly Glu Arg
                275                 280                 285
Gly Phe Pro Gly Leu Pro Gly Pro Ser Gly Glu Pro Gly Lys Gln Gly
                290                 295                 300
Pro Ser Gly Ala Ser Gly Glu Arg Gly Pro Pro Gly Pro Met Gly Pro
305                 310                 315                 320
Pro Gly Leu Ala Gly Pro Pro Gly Glu Ser Gly Arg Glu Gly Ala Pro
                325                 330                 335
Ala Ala Glu Gly Ser Pro Gly Arg Asp Gly Ser Pro Gly Ala Lys Gly
                340                 345                 350
Asp Arg Gly Glu Thr Gly Pro Ala Gly Pro Pro Gly Ala Pro Gly Ala
                355                 360                 365
Pro Gly Ala Pro Gly Pro Val Gly Pro Ala Gly Lys Ser Gly Asp Arg
                370                 375                 380
Gly Glu Thr Gly Pro Ala Gly Pro Ala Gly Pro Val Gly Pro Val Gly
385                 390                 395                 400
Ala Arg Gly Pro Ala Gly Pro Gln Gly Pro Arg Gly Asp Lys Gly Glu
                405                 410                 415
Thr Gly Glu Gln Gly Asp Arg Gly Ile Lys Gly His Arg Gly Phe Ser
                420                 425                 430
Gly Leu Gln Gly Pro Pro Gly Pro Pro Gly Ser Pro Gly Glu Gln Gly
                435                 440                 445
Pro Ser Gly Ala Ser Gly Pro Ala Gly Pro Arg Gly Pro Pro Gly Ser
                450                 455                 460
Ala Gly Ala Pro Gly Lys Asp Gly Leu Asn Gly Leu Pro Gly Pro Ile
465                 470                 475                 480
Gly Pro Pro Gly Pro Arg Gly Arg Thr Gly Asp Ala Gly Pro Val Gly
                485                 490                 495
Pro Pro Gly Pro Pro Gly Pro Pro Gly Pro Pro Gly Pro Pro
                500                 505                 510

<210> SEQ ID NO 27
<211> LENGTH: 333
<212> TYPE: PRT
<213> ORGANISM: human

<400> SEQUENCE: 27

Gly Ala Lys Gly Ala Arg Gly Ser Ala Gly Pro Pro Gly Ala Thr Gly
1               5                   10                  15
```

```
Phe Pro Gly Ala Ala Gly Arg Val Gly Pro Gly Pro Ser Gly Asn
            20                  25                  30

Ala Gly Pro Gly Pro Gly Pro Ala Gly Lys Glu Gly Gly Lys
        35                  40                  45

Gly Pro Arg Gly Glu Thr Gly Pro Ala Gly Arg Pro Gly Glu Val Gly
    50                  55                  60

Pro Pro Gly Pro Gly Pro Ala Gly Glu Lys Gly Ser Pro Gly Ala
65                  70                  75                  80

Asp Gly Pro Ala Gly Ala Pro Gly Thr Pro Gly Pro Gln Gly Ile Ala
                85                  90                  95

Gly Gln Arg Gly Val Val Gly Leu Pro Gly Gln Arg Gly Glu Arg Gly
            100                 105                 110

Phe Pro Gly Leu Pro Gly Pro Ser Gly Glu Pro Gly Lys Gln Gly Pro
            115                 120                 125

Ser Gly Ala Ser Gly Glu Arg Gly Pro Pro Gly Pro Met Gly Pro Pro
130                 135                 140

Gly Leu Ala Gly Pro Pro Gly Glu Ser Gly Arg Glu Gly Ala Pro Ala
145                 150                 155                 160

Ala Glu Gly Ser Pro Gly Arg Asp Gly Ser Pro Gly Ala Lys Gly Asp
                165                 170                 175

Arg Gly Glu Thr Gly Pro Ala Gly Pro Pro Gly Ala Pro Gly Ala Pro
            180                 185                 190

Gly Ala Pro Gly Pro Val Gly Pro Ala Gly Lys Ser Gly Asp Arg Gly
        195                 200                 205

Glu Thr Gly Pro Ala Gly Pro Ala Gly Pro Val Gly Pro Val Gly Ala
    210                 215                 220

Arg Gly Pro Ala Gly Pro Gln Gly Pro Arg Gly Asp Lys Gly Glu Thr
225                 230                 235                 240

Gly Glu Gln Gly Asp Arg Gly Ile Lys Gly His Arg Gly Phe Ser Gly
                245                 250                 255

Leu Gln Gly Pro Pro Gly Pro Pro Gly Ser Pro Gly Glu Gln Gly Pro
            260                 265                 270

Ser Gly Ala Ser Gly Pro Ala Gly Pro Arg Gly Pro Pro Gly Ser Ala
        275                 280                 285

Gly Ala Pro Gly Lys Asp Gly Leu Asn Gly Leu Pro Gly Pro Ile Gly
    290                 295                 300

Pro Pro Gly Pro Arg Gly Arg Thr Gly Asp Ala Gly Pro Val Gly Pro
305                 310                 315                 320

Pro Gly Pro Pro Gly Pro Pro Gly Pro Pro Gly Pro Pro
                325                 330

<210> SEQ ID NO 28
<211> LENGTH: 200
<212> TYPE: PRT
<213> ORGANISM: human

<400> SEQUENCE: 28

Glu Arg Gly Pro Pro Gly Pro Met Gly Pro Pro Gly Leu Ala Gly Pro
1               5                   10                  15

Pro Gly Glu Ser Gly Arg Glu Gly Ala Pro Ala Ala Glu Gly Ser Pro
            20                  25                  30

Gly Arg Asp Gly Ser Pro Gly Ala Lys Gly Asp Arg Gly Glu Thr Gly
        35                  40                  45

Pro Ala Gly Pro Pro Gly Ala Pro Gly Ala Pro Gly Ala Pro Gly Pro
    50                  55                  60
```

```
Val Gly Pro Ala Gly Lys Ser Gly Asp Arg Gly Glu Thr Gly Pro Ala
 65                  70                  75                  80

Gly Pro Ala Gly Pro Val Gly Pro Val Gly Ala Arg Gly Pro Ala Gly
             85                  90                  95

Pro Gln Gly Pro Arg Gly Asp Lys Gly Glu Thr Gly Glu Gln Gly Asp
            100                 105                 110

Arg Gly Ile Lys Gly His Arg Gly Phe Ser Gly Leu Gln Gly Pro Pro
        115                 120                 125

Gly Pro Pro Gly Ser Pro Gly Glu Gln Gly Pro Ser Gly Ala Ser Gly
    130                 135                 140

Pro Ala Gly Pro Arg Gly Pro Pro Gly Ser Ala Gly Ala Pro Gly Lys
145                 150                 155                 160

Asp Gly Leu Asn Gly Leu Pro Gly Pro Ile Gly Pro Pro Gly Pro Arg
                165                 170                 175

Gly Arg Thr Gly Asp Ala Gly Pro Val Gly Pro Pro Gly Pro Pro Gly
            180                 185                 190

Pro Pro Gly Pro Pro Gly Pro Pro
        195                 200

<210> SEQ ID NO 29
<211> LENGTH: 100
<212> TYPE: PRT
<213> ORGANISM: human

<400> SEQUENCE: 29

Arg Gly Asp Lys Gly Glu Thr Gly Glu Gln Gly Asp Arg Gly Ile Lys
  1               5                  10                  15

Gly His Arg Gly Phe Ser Gly Leu Gln Gly Pro Pro Gly Pro Pro Gly
             20                  25                  30

Ser Pro Gly Glu Gln Gly Pro Ser Gly Ala Ser Gly Pro Ala Gly Pro
         35                  40                  45

Arg Gly Pro Pro Gly Ser Ala Gly Ala Pro Gly Lys Asp Gly Leu Asn
 50                  55                  60

Gly Leu Pro Gly Pro Ile Gly Pro Pro Gly Pro Arg Gly Arg Thr Gly
 65                  70                  75                  80

Asp Ala Gly Pro Val Gly Pro Pro Gly Pro Pro Gly Pro Pro Gly Pro
                 85                  90                  95

Pro Gly Pro Pro
            100

<210> SEQ ID NO 30
<211> LENGTH: 62
<212> TYPE: PRT
<213> ORGANISM: human

<400> SEQUENCE: 30

Glu Ala Gly Ala Gln Gly Pro Pro Gly Pro Ala Gly Pro Ala Gly Glu
  1               5                  10                  15

Arg Gly Glu Gln Gly Pro Ala Gly Ser Pro Gly Phe Gln Gly Leu Pro
             20                  25                  30

Gly Pro Ala Gly Pro Pro Gly Glu Ala Gly Lys Pro Gly Glu Gln Gly
         35                  40                  45

Val Pro Gly Asp Leu Gly Ala Pro Gly Pro Ser Gly Ala Arg
 50                  55                  60

<210> SEQ ID NO 31
```

<211> LENGTH: 251
<212> TYPE: PRT
<213> ORGANISM: human

<400> SEQUENCE: 31

Glu Ala Gly Ala Gln Gly Pro Pro Gly Pro Ala Gly Pro Ala Gly Glu
1               5                   10                  15

Arg Gly Glu Gln Gly Pro Ala Gly Ser Pro Gly Phe Gln Gly Leu Pro
            20                  25                  30

Gly Pro Ala Gly Pro Pro Gly Glu Ala Gly Lys Pro Gly Glu Gln Gly
        35                  40                  45

Val Pro Gly Asp Leu Gly Ala Pro Gly Pro Ser Gly Ala Arg Gly Glu
    50                  55                  60

Arg Gly Phe Pro Gly Glu Arg Gly Val Gln Gly Pro Pro Gly Pro Ala
65                  70                  75                  80

Gly Pro Arg Gly Ala Asn Gly Ala Pro Gly Asn Asp Gly Ala Lys Gly
                85                  90                  95

Asp Ala Gly Ala Pro Gly Ala Pro Gly Ser Gln Gly Ala Pro Gly Leu
            100                 105                 110

Gln Gly Met Pro Gly Glu Arg Gly Ala Ala Gly Leu Pro Gly Pro Lys
        115                 120                 125

Gly Asp Arg Gly Asp Ala Gly Pro Lys Gly Ala Asp Gly Ser Pro Gly
    130                 135                 140

Lys Asp Gly Val Arg Gly Leu Thr Gly Pro Ile Gly Pro Pro Gly Pro
145                 150                 155                 160

Ala Gly Ala Pro Gly Asp Lys Gly Glu Ser Gly Pro Ser Gly Pro Ala
                165                 170                 175

Gly Pro Thr Gly Ala Arg Gly Ala Pro Gly Asp Arg Gly Glu Pro Gly
            180                 185                 190

Pro Pro Gly Pro Ala Gly Phe Ala Gly Pro Pro Gly Ala Asp Gly Gln
        195                 200                 205

Pro Gly Ala Lys Gly Glu Pro Gly Asp Ala Gly Ala Lys Gly Asp Ala
    210                 215                 220

Gly Pro Pro Gly Pro Ala Gly Pro Ala Gly Pro Pro Gly Pro Ile Gly
225                 230                 235                 240

Asn Val Gly Ala Pro Gly Ala Lys Gly Ala Arg
                245                 250

<210> SEQ ID NO 32
<211> LENGTH: 43
<212> TYPE: DNA
<213> ORGANISM: human

<400> SEQUENCE: 32
agcttctaga ttattaggga ggaccagggg gaccaggagg tcc         43

<210> SEQ ID NO 33
<211> LENGTH: 662
<212> TYPE: PRT
<213> ORGANISM: human

<400> SEQUENCE: 33

Glu Ala Gly Leu Pro Gly Ala Lys Gly Leu Thr Gly Ser Pro Gly Ser
1               5                   10                  15

Pro Gly Pro Asp Gly Lys Thr Gly Pro Pro Gly Pro Ala Gly Gln Asp
            20                  25                  30

Gly Arg Pro Gly Pro Pro Gly Pro Pro Gly Ala Arg Gly Gln Ala Gly

-continued

```
                35                  40                  45
Val Met Gly Phe Pro Gly Pro Lys Gly Ala Ala Gly Glu Pro Gly Lys
         50                  55                  60

Ala Gly Glu Arg Gly Val Pro Gly Pro Pro Gly Ala Val Gly Pro Ala
 65                  70                  75                  80

Gly Lys Asp Gly Glu Ala Gly Ala Gln Gly Pro Pro Gly Pro Ala Gly
                 85                  90                  95

Pro Ala Gly Glu Arg Gly Glu Gln Gly Pro Ala Gly Ser Pro Gly Phe
                100                 105                 110

Gln Gly Leu Pro Gly Pro Ala Gly Pro Gly Glu Ala Gly Lys Pro
            115                 120                 125

Gly Glu Gln Gly Val Pro Gly Asp Leu Gly Ala Pro Gly Pro Ser Gly
        130                 135                 140

Ala Arg Gly Glu Arg Gly Phe Pro Gly Glu Arg Gly Val Gln Gly Pro
145                 150                 155                 160

Pro Gly Pro Ala Gly Pro Arg Gly Ala Asn Gly Ala Pro Gly Asn Asp
                165                 170                 175

Gly Ala Lys Gly Asp Ala Gly Ala Pro Gly Ala Pro Gly Ser Gln Gly
            180                 185                 190

Ala Pro Gly Leu Gln Gly Met Pro Gly Glu Arg Gly Ala Ala Gly Leu
        195                 200                 205

Pro Gly Pro Lys Gly Asp Arg Gly Asp Ala Gly Pro Lys Gly Ala Asp
    210                 215                 220

Gly Ser Pro Gly Lys Asp Gly Val Arg Gly Leu Thr Gly Pro Ile Gly
225                 230                 235                 240

Pro Pro Gly Pro Ala Gly Ala Pro Gly Asp Lys Gly Glu Ser Gly Pro
                245                 250                 255

Ser Gly Pro Ala Gly Pro Thr Gly Ala Arg Gly Ala Pro Gly Asp Arg
            260                 265                 270

Gly Glu Pro Gly Pro Pro Gly Pro Ala Gly Phe Ala Gly Pro Pro Gly
        275                 280                 285

Ala Asp Gly Gln Pro Gly Ala Lys Gly Glu Pro Gly Asp Ala Gly Ala
    290                 295                 300

Lys Gly Asp Ala Gly Pro Pro Gly Pro Ala Gly Pro Ala Gly Pro Pro
305                 310                 315                 320

Gly Pro Ile Gly Asn Val Gly Ala Pro Gly Ala Lys Gly Ala Arg Gly
                325                 330                 335

Ser Ala Gly Pro Pro Gly Ala Thr Gly Phe Pro Gly Ala Ala Gly Arg
            340                 345                 350

Val Gly Pro Pro Gly Pro Ser Gly Asn Ala Gly Pro Pro Gly Pro Pro
        355                 360                 365

Gly Pro Ala Gly Lys Glu Gly Gly Lys Gly Pro Arg Gly Glu Thr Gly
    370                 375                 380

Pro Ala Gly Arg Pro Gly Glu Val Gly Pro Pro Gly Pro Pro Gly Pro
385                 390                 395                 400

Ala Gly Glu Lys Gly Ser Pro Gly Ala Asp Gly Pro Ala Gly Ala Pro
                405                 410                 415

Gly Thr Pro Gly Pro Gln Gly Ile Ala Gly Gln Arg Gly Val Val Gly
            420                 425                 430

Leu Pro Gly Gln Arg Gly Glu Arg Gly Phe Pro Gly Leu Pro Gly Pro
        435                 440                 445

Ser Gly Glu Pro Gly Lys Gln Gly Pro Ser Gly Ala Ser Gly Glu Arg
    450                 455                 460
```

-continued

```
Gly Pro Pro Gly Pro Met Gly Pro Pro Gly Leu Ala Gly Pro Pro Gly
465                 470                 475                 480

Glu Ser Gly Arg Glu Gly Ala Pro Ala Ala Glu Gly Ser Pro Gly Arg
                485                 490                 495

Asp Gly Ser Pro Gly Ala Lys Gly Asp Arg Gly Glu Thr Gly Pro Ala
            500                 505                 510

Gly Pro Pro Gly Ala Pro Gly Ala Pro Gly Ala Pro Gly Pro Val Gly
        515                 520                 525

Pro Ala Gly Lys Ser Gly Asp Arg Gly Glu Thr Gly Pro Ala Gly Pro
        530                 535                 540

Ala Gly Pro Val Gly Pro Val Gly Ala Arg Gly Pro Ala Gly Pro Gln
545                 550                 555                 560

Gly Pro Arg Gly Asp Lys Gly Glu Thr Gly Glu Gln Gly Asp Arg Gly
                565                 570                 575

Ile Lys Gly His Arg Gly Phe Ser Gly Leu Gln Gly Pro Pro Gly Pro
            580                 585                 590

Pro Gly Ser Pro Gly Glu Gln Gly Pro Ser Gly Ala Ser Gly Pro Ala
        595                 600                 605

Gly Pro Arg Gly Pro Pro Gly Ser Ala Gly Ala Pro Gly Lys Asp Gly
    610                 615                 620

Leu Asn Gly Leu Pro Gly Pro Ile Gly Pro Pro Gly Pro Arg Gly Arg
625                 630                 635                 640

Thr Gly Asp Ala Gly Pro Val Gly Pro Pro Gly Pro Pro Gly Pro Pro
            645                 650                 655

Gly Pro Pro Gly Pro Pro
                660
```